(12) United States Patent
Nagai et al.

(10) Patent No.: US 11,268,121 B2
(45) Date of Patent: Mar. 8, 2022

(54) CAROTENOID PRODUCTION METHOD

(71) Applicant: JXTG NIPPON OIL & ENERGY CORPORATION, Tokyo (JP)

(72) Inventors: Hidetada Nagai, Tokyo (JP); Wataru Sato, Tokyo (JP); Toshiyuki Takahashi, Tokyo (JP); Harumi Sato, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 467 days.

(21) Appl. No.: 16/088,058

(22) PCT Filed: Mar. 29, 2017

(86) PCT No.: PCT/JP2017/014162
§ 371 (c)(1),
(2) Date: Sep. 24, 2018

(87) PCT Pub. No.: WO2017/171098
PCT Pub. Date: Oct. 5, 2017

(65) Prior Publication Data
US 2020/0299747 A1    Sep. 24, 2020

(30) Foreign Application Priority Data
Mar. 31, 2016   (JP) .............................. JP2016-071303

(51) Int. Cl.
*C12N 1/20* (2006.01)
*C12N 15/74* (2006.01)
(Continued)

(52) U.S. Cl.
CPC ............... *C12P 23/00* (2013.01); *C12N 1/20* (2013.01); *C12N 5/10* (2013.01); *C12N 15/52* (2013.01);
(Continued)

(58) Field of Classification Search
None
See application file for complete search history.

(56) References Cited

U.S. PATENT DOCUMENTS

| | | |
|---|---|---|
| 5,858,761 A | 1/1999 | Tsubokura et al. |
| 2003/0148416 A1 | 8/2003 | Berry et al. |

(Continued)

FOREIGN PATENT DOCUMENTS

| | | |
|---|---|---|
| EP | 2157168 A1 | 2/2010 |
| JP | H07-079796 A | 3/1995 |

(Continued)

OTHER PUBLICATIONS

Gen Bank Accession No. EEB85694.1, published Mar. 11, 2015 (Year: 2015).*

(Continued)

*Primary Examiner* — Richard C Ekstrom
(74) *Attorney, Agent, or Firm* — McDermott Will & Emery LLP

(57) ABSTRACT

A mutant carotenoidogenic bacterium, comprising any of genes (a)-(c) below: (a) a gene encoding a protein comprising a mutant amino acid sequence in which at least the 225th amino acid residue in the amino acid sequence of 1-deoxy-D-xylulose 5-phosphate synthase of a carotenoidogenic bacterium has been substituted with other amino acid residue; (b) a gene encoding a protein comprising a mutant amino acid sequence in which at least the 305th amino acid residue in the amino acid sequence of decaprenyl diphosphate synthase of a carotenoidogenic bacterium has been substituted with other amino acid residue; and (c) both of the genes (a) and (b) above.

11 Claims, 34 Drawing Sheets

Specification includes a Sequence Listing.

(51) Int. Cl.
  *C12P 23/00* (2006.01)
  *C12N 5/10* (2006.01)
  *C12N 15/52* (2006.01)
(52) U.S. Cl.
  CPC ...... *C12N 15/74* (2013.01); *C12Y 202/01007* (2013.01); *C12Y 205/01086* (2013.01); *C12Y 205/01091* (2013.01)

(56) References Cited

U.S. PATENT DOCUMENTS

| | | |
|---|---|---|
| 2006/0219629 A1 | 10/2006 | Noestheden |
| 2007/0054351 A1 | 3/2007 | Zhang |
| 2007/0202579 A1 | 8/2007 | Berry et al. |
| 2007/0231854 A1 | 10/2007 | Stead et al. |
| 2009/0298146 A1 | 12/2009 | Choi et al. |
| 2011/0262981 A1 | 10/2011 | Hirasawa et al. |
| 2013/0012594 A1 | 1/2013 | Hirasawa et al. |
| 2013/0276166 A1 | 10/2013 | Hugueney et al. |
| 2014/0148622 A1* | 5/2014 | Nair ................ C12N 15/8243 585/16 |
| 2017/0121749 A1 | 5/2017 | Chabot et al. |
| 2020/0299747 A1* | 9/2020 | Nagai .................. C12N 5/10 |

FOREIGN PATENT DOCUMENTS

| | | |
|---|---|---|
| JP | H11-069969 A | 3/1999 |
| JP | 2001-512030 A | 8/2001 |
| JP | 2004-527265 A | 9/2004 |
| JP | 2006-515174 A | 5/2006 |
| JP | 2006-340676 A | 12/2006 |
| JP | 2007-097584 A | 4/2007 |
| JP | 2007-143492 A | 6/2007 |
| JP | 2007-244205 A | 9/2007 |
| JP | 2008-509689 A | 4/2008 |
| JP | 2008-259449 A | 10/2008 |
| JP | 2009-142275 A | 7/2009 |
| JP | 2011-188795 A | 9/2011 |
| JP | 2012-139164 A | 7/2012 |
| KR | 20090074926 A | 7/2009 |
| WO | 88/08025 A1 | 10/1988 |
| WO | 99/06586 A1 | 2/1999 |
| WO | 2004/056974 A2 | 7/2004 |
| WO | 2004/056975 A2 | 7/2004 |
| WO | 2005/118812 A1 | 12/2005 |
| WO | 2006/018211 A1 | 2/2006 |
| WO | 2007/050769 A2 | 5/2007 |
| WO | 2007/126639 A1 | 11/2007 |
| WO | 2010/044469 A1 | 4/2010 |
| WO | 2011/115099 A1 | 9/2011 |
| WO | 2012/052171 A1 | 4/2012 |
| WO | 2015/189428 A1 | 12/2015 |

OTHER PUBLICATIONS

PIR Accession No. A70377, published May 8, 1998 (Year: 1998).*
Chinese Office Acition issued in corresponding Chinese Application No. 201780020844.4, dated Sep. 16, 2019, with English translation.
"UPI0005FA75D6," Jun. 24, 2015, XP55618235, https://www.uniprot.org/uniparc/UPI0005FA75D6?filter=active:no, retrieved on Sep. 4, 2019.
Jung-Kul Lee et al., "Cloning and characterization of the dxs gene, encoding 1-deoxy-D-xylulose 5-phosphate synthase from Agrobacterium tumefaciens, and its overexpression in Agrobacterium tumefaciens," Journal of Biotechnology, Elsevier, Amsterdam, NL, vol. 128, No. 3, Jan. 24, 2007, pp. 555-566.
S. Sanchez et al., "Microbial production of carotenoids," Microbial Production of Food Ingredients, Enzymes and Nutraceuticals, Woodhead Publishing, GB, Jan. 1, 2013, pp. 194-233.
Partial Supplementary European Search Report issued in corresponding European Patent Application No. 17775629.3, dated Sep. 18, 2019.
Database GenBank [online], Accession JYGY01000003, Feb. 23, 2015 uploaded, Karczewska-Golec, J., et al. Difinition: *Paracoccus* sp. 361 scaffold_2, whole genome shotgun sequence.
Ide, T., et al., Enhanced production of astaxanthin in *Paracoccus* sp. strain N-81106 by using random mutagenesis and genetic engineering, Biochem. Eng. J., 2012, vol. 65, p. 37-43, ISSN 1369-703X.
Database GenBank [online], Accession No. KRW96790, Nov. 23, 2015 uploaded, Nisha, K.N. et al., Definition: 1-deoxy-D--xylulose-5-phosphate synthase.
Database GenBank [online], Accession No. ABL68514, Jan. 28, 2014 uploaded, Copeland, A. et al., Definition: 1-deoxy-D-xylulose-5-phosphate synthase.
Database GenBank [online], Accession No. KGJ12376, Oct. 6, 2014 uploaded, Mingle, L.A. et al., Definition: 1-deoxy-D-xylulose-5-phosphate synthase.
Database GenBank [online], Accession No. AGT07340, Feb. 27, 2014 uploaded, Dziewit, L. et al., Definition: 1-deoxy-D-xylulose-5-phosphate synthase.
International Search Report issued in International Application No. PCT/JP2017/014162 dated Jun. 27, 2017 (with English translation).
E. Widmer, "Synthetic advances in the carotenoid field", Pure & Appl. Chem., vol. 57, pp. 741-752, 1985. (cited in specification).
E. Widmer et al., Helvetica Chimca Acta, vol. 64, Fase. 7,(1981), pp. 2436-2446. (cited in specification).
Lee et al., International Journal of Systematic and Eveolutional Microbiology (2004), 54, 1699-1702. (cited in specification).
Berry et al., International Journal of Systematic and Evolutionary Microbiology (2003), 53, 231-238. (cited in specification).
Tsubokura et al., International Journal of Systematic Bacteriology, (1999), 49, 277-282. (cited in specification).
Extended European Search Report issued in corresponding European Patent Application No. 17775629.3, dated Dec. 5, 2019.
Okada, K. et al., "Molecular cloning and mutational analysis of the ddsA gene encoding decaprenyl diphosphate synthase from Gluconobacter suboxydans," European Journal of Biochemistry, Wiley-Blackwell Publishing Ltd, GB, vol. 255, No. 1, Jan. 1, 1998, pp. 52-59.
Korean Office Action issued tri corresponding Korean Patent Application No. 10-2018-7026936, dated Feb. 22, 2021, with English translation.
European Office Action issued in corresponding European Patent Application No. 17775629.3, dated Sep. 2, 2021.

* cited by examiner

| Protein | 1-deoxy-D-xylulose-5-phosphate synthase | | |
|---|---|---|---|
| UniProt | Q9RUB5 (DXS_DEIRA) | | EC:2.2.1.7 |
| Organism | *Deinococcus radiodurans* | | |
| Pfam | PF13292 | DXP_synthase_N | |
| PDB ID | 2O1X | Resolution: 2.90[Å] | dimer |
| Identity | 44.1% | 7-630 | |

2O1X

Fig. 4

Fig. 5
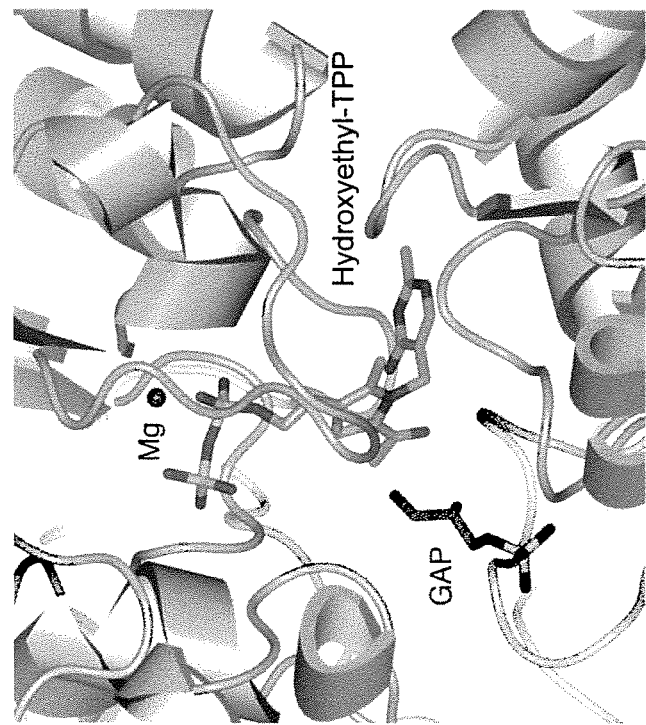
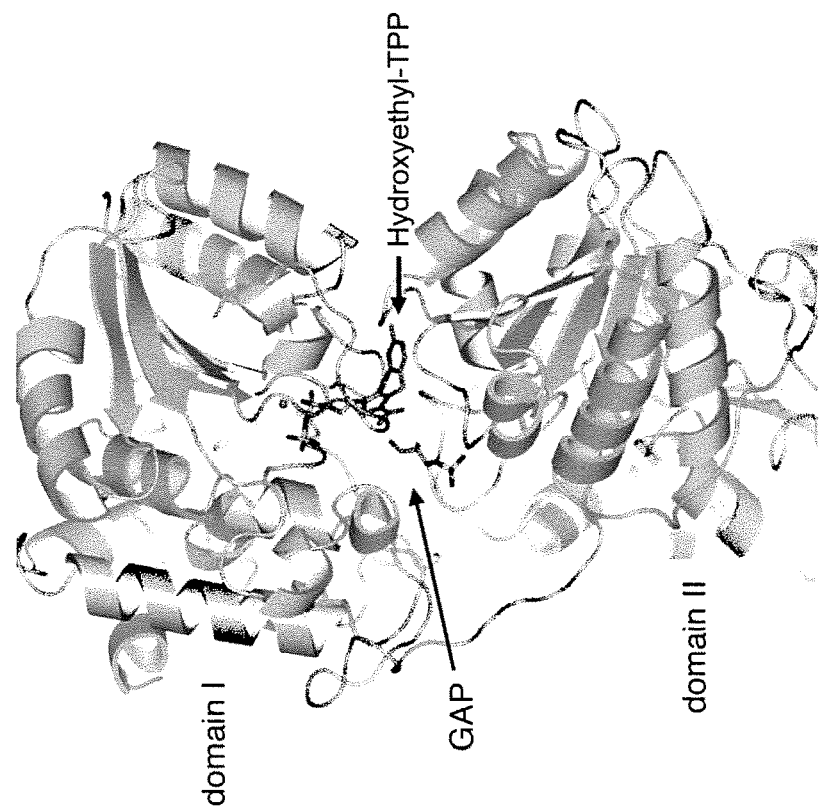

Fig. 7
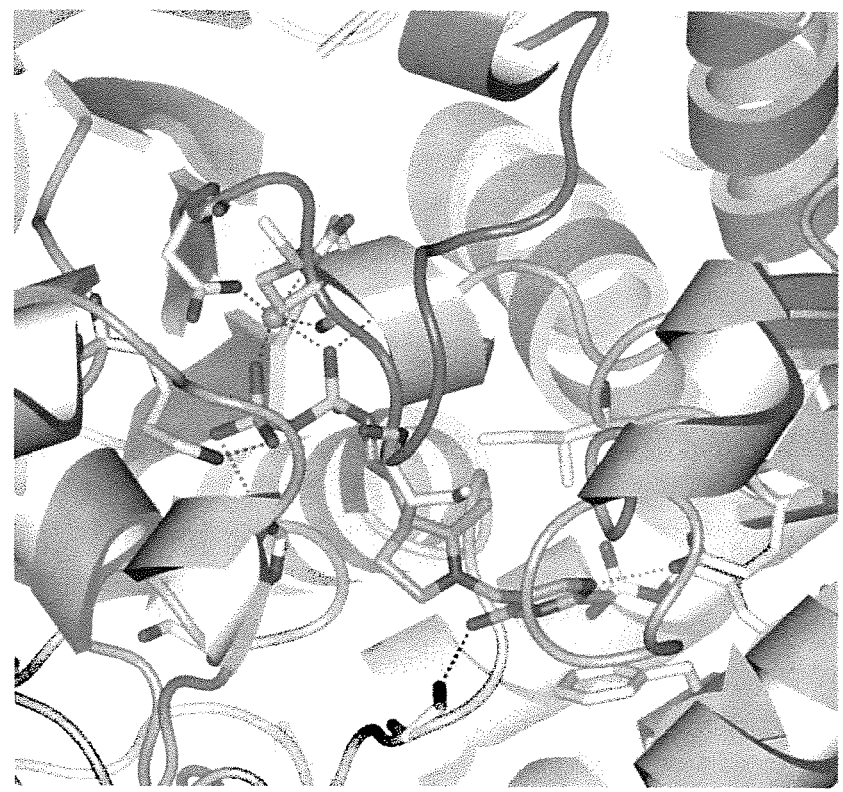
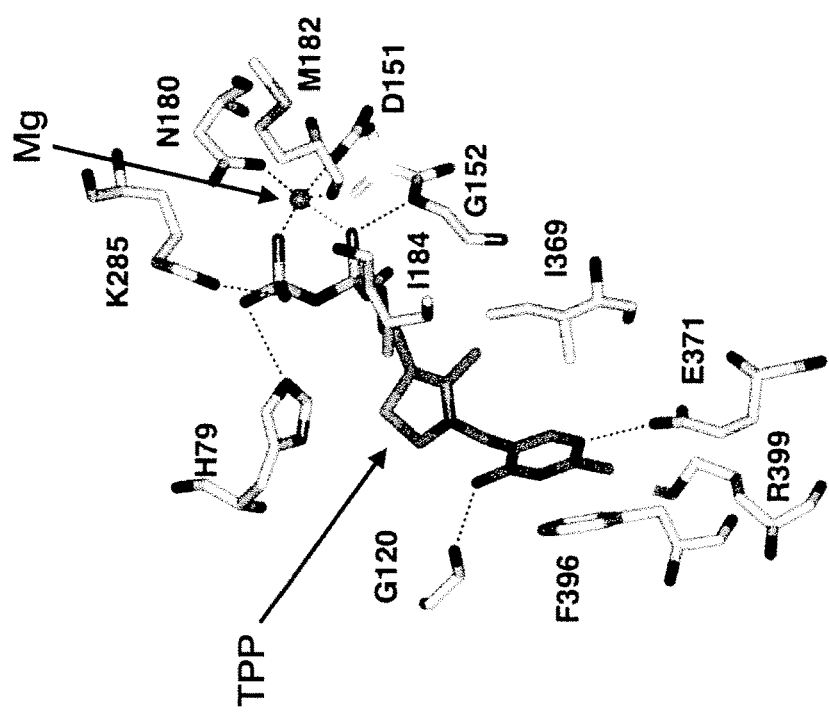

Fig. 8
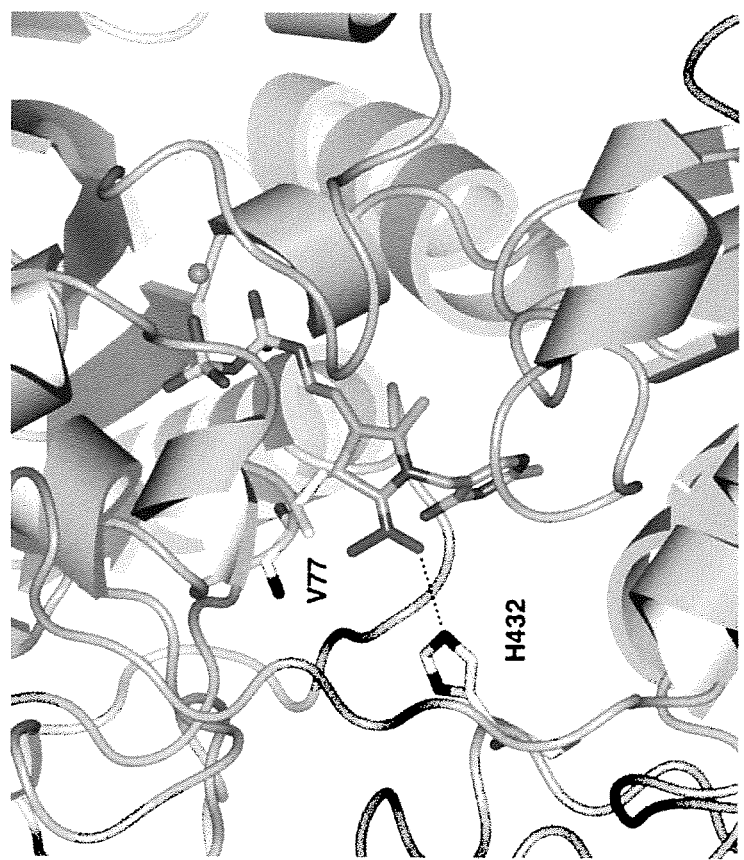
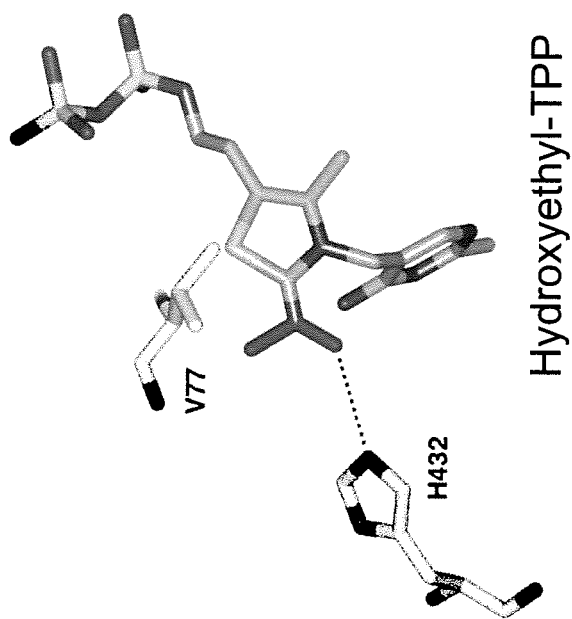

Fig. 9
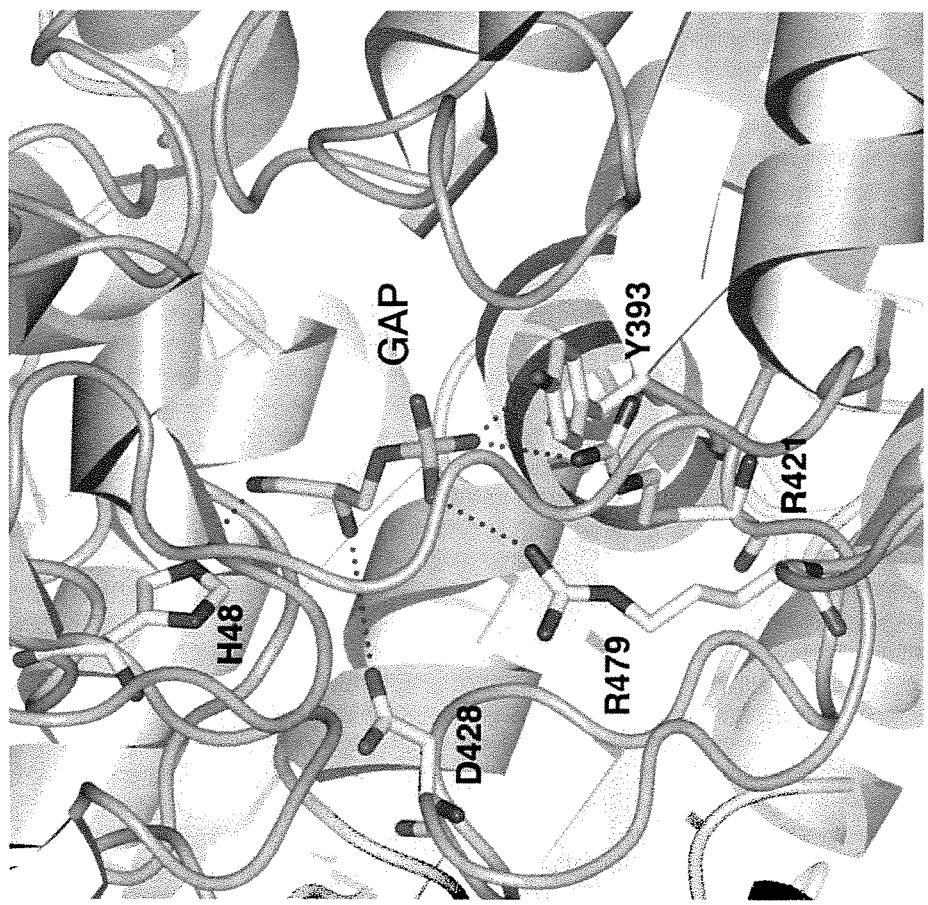
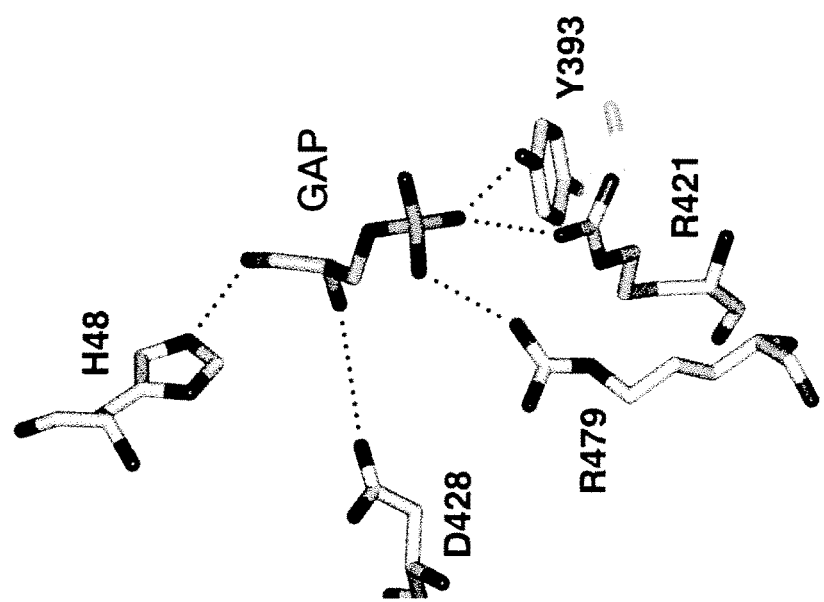

Fig. 12

```
EnzymeA     GAGHSSTSISAALGFAMARELGGDPGDAIAVIGDGAMSAGMAYEALNNAGHEGKRLFVVL 177
DXS_ECOLI   SVGHSSTSISAGIGIAVAAEKEGKNRRTVCVIGDGAITAGMAFEAMNHAGDIRPDMLVIL 178
DXS_VITVI   GTGHSSTTISAGLGMAVGRDLKGKNNNVIAVIGDGAMTAGQAYEAMNNAGYLDSDMIVIL 240
DXS_DEIRA   TVGHASTSLANALGMALARDAQGKDFHVAAVIGDGSLTGGMALAALNTIGDMGRKMLIVL 180
            . **:****:: .::*:*: :.       *    .      *     ::*::*  *
                                                                    ↓G225D
EnzymeA     NDNEMS------HAPPVGAMSSYLTRLYAGGPFQELKAVAKGAVGMLPDALQEGARR  228
DXS_ECOLI   NDNEMS------ISENVGALNNHLAQLLSGKLYSSLREGGKKVFSGVP-PIKELLKR  228
DXS_VITVI   NDNKQVSLPTATLDGPIPPVGALSSALSRLQSNRPLRELREYAKGVTKQIGGPMHELAAK 300
DXS_DEIRA   NDNEMS------ISENVGAMNKFMRGLQVQKWFQEGEGAGKKAVEAVSKPLADEMSR  231
            ***         .        .       ..   ::      *
                                                K213N  K284N EnzymeA     AKEMLKGMA--VGGTLFEELGFSYIGPVDGHDMEQLLPLLRTVR-ARADGPVLIHVVTKK 285
DXS_ECOLI   TEEHIKGMV--VPGTLFEELGFNYIGPVDGHDVLGLITTLKNMR--DLKGPFLHIMTKK 284
DXS_VITVI   VDEYARGMISGSGSTLFEELGLYYIGPVDGHNIDDLVAILKEVKSTKTTGPVLIHVVTEK 360
DXS_DEIRA   AKWSTRHFFDPASVNPFAAMGVRYVGPVDGHNVQELVWLLERLIV--DLDGPTILHIVTTK 289
            .        .         .*   :***** :    : :::..    . .* ::*:.*
            K234C    R306C
```

Fig. 13
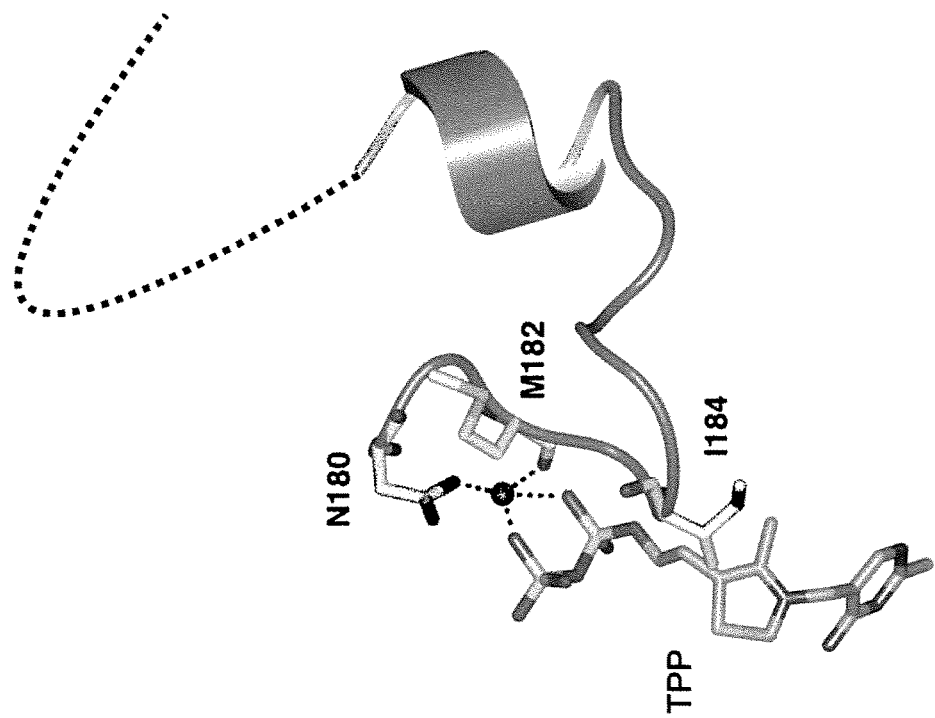
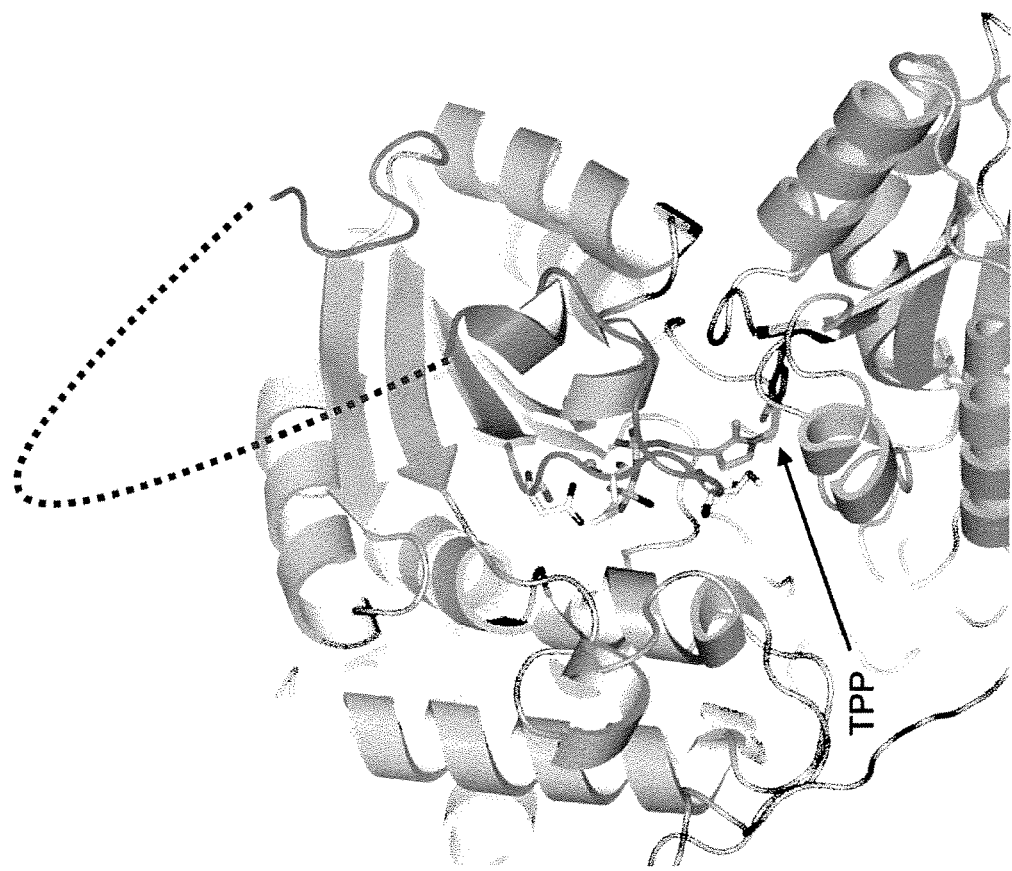

| Protein | Decaprenyl diphosphate synthase | | EC:2.5.1.91 |
|---|---|---|---|
| UniProt | Q07D00 (Q07D00_RHOCA) | | |
| Organism | *Rhodobacter capsulatus* | | |
| Pfam | PF00348 | Polyprenyl synthetase | |
| PDB ID | 3MZV | Resolution: 1.90[Å] | dimer |
| Identity | 76.2% | 10-332 | |

3MZV

Fig. 17

```
EnzymeC  MTVQDNVRKP MDRLSEALTA EMEAVNALIR DRMASRHAPR IPEVTAHLIE AGGKRLRPML  60
3mzv     MSLDDKATKP HDRLAQALAE DMAAVNALIR ERMSSEHAPR IPEVTAHLIE AGGKRLRPML EnzymeC  TLAAAKLLGY PGPWHVHLAA TVEFIHTATL LHDDVVDESA QRRGRPTANL LWDNKSSVLV  120
3mzv     TLAAARLVGY GGPFHVHLAA TVEFIHTATL LHDDVVDESR QRRGRPTANL LWDNKSSVLV EnzymeC  GDYLFARSFQ LMVEPGNLRT LEILANASAT IAEGEVLQLT AAQDLATDES VYLQVVRGKT  180
3mzv     GDYLFARSFQ LMTDTGNMRV MEILANASAV IAEGEVLQLT AAQNLATTED IYLRVIRGKT EnzymeC  AALFSAATEV GGVIAGAPDD QVQALFDYGD ALGISFQIVD DLIDYGGATE TIGKNVGDDF  240
3mzv     AALFSAATEV GGIIGGAPED QVQALFDYGD ALGIAFQIVD DLIDYGGKSA EIGKNTGDDF EnzymeC  RERKLTLPVI KAIAKADAEE RAFWTRTIEA GDQRDGDLEH ALSLLARHGA MEAARADALA  300
3mzv     RERKLTMPVI KAVALADEAE RAFWKRVIEK GDQQDGDLEH AMALMTKHGT LEATRLAAIG EnzymeC  HAARVRAALQ VLPAHPIRDM LADLADFVVS RV  332
3mzv     WTDTARKALA KLPDHPLRQM LDDLADYVVE RV
```

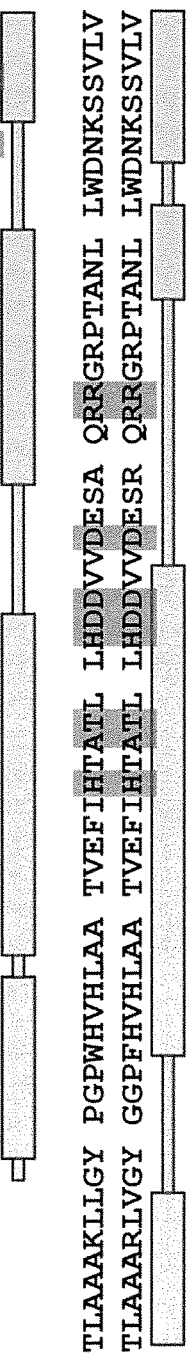

Fig. 18
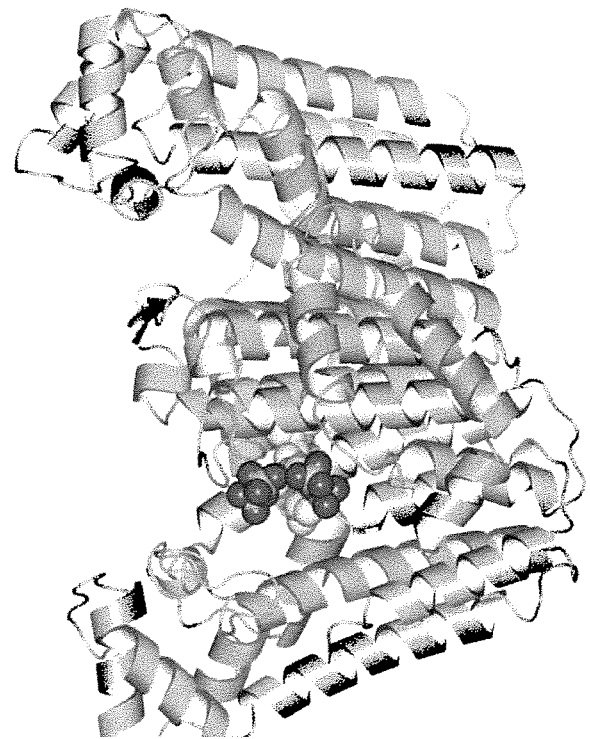
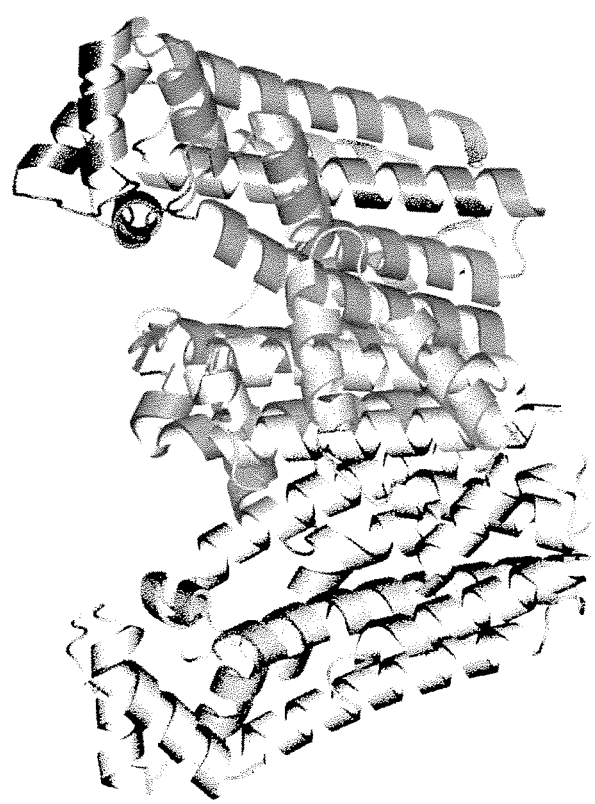

Fig. 19
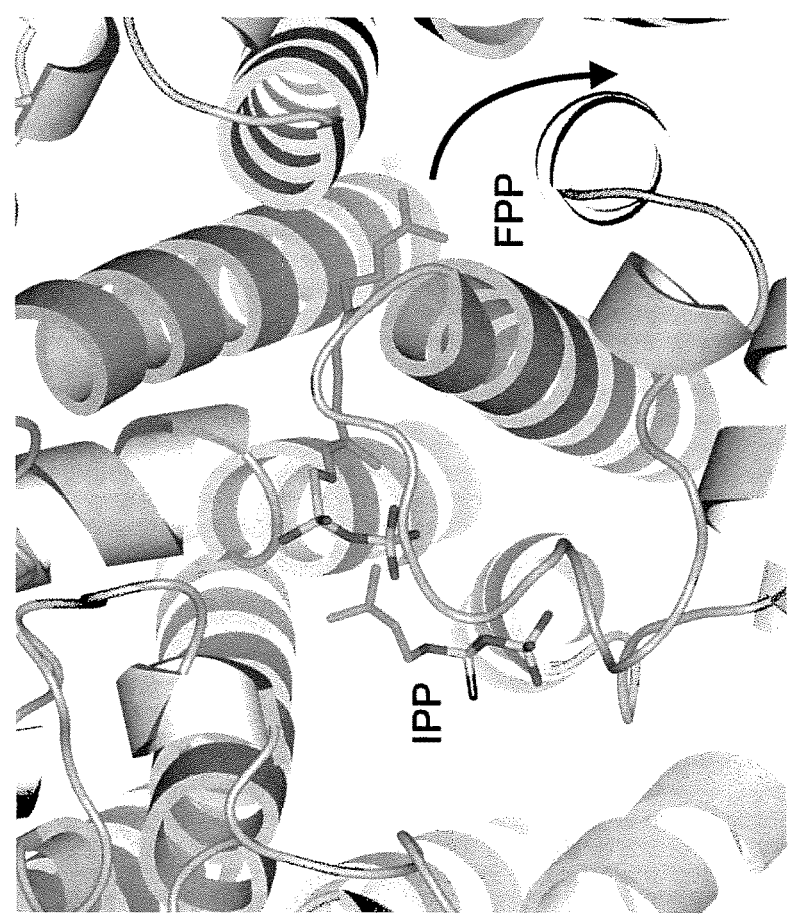
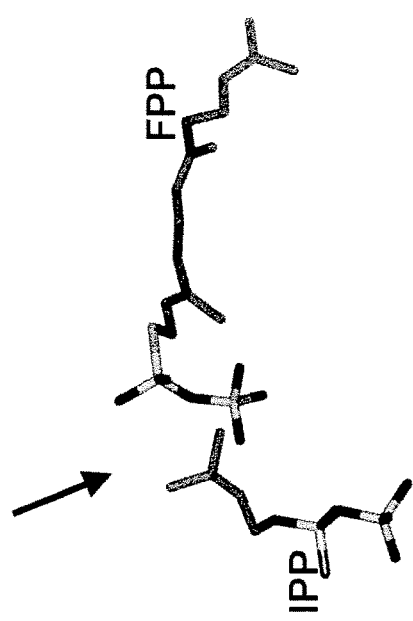

Fig. 20
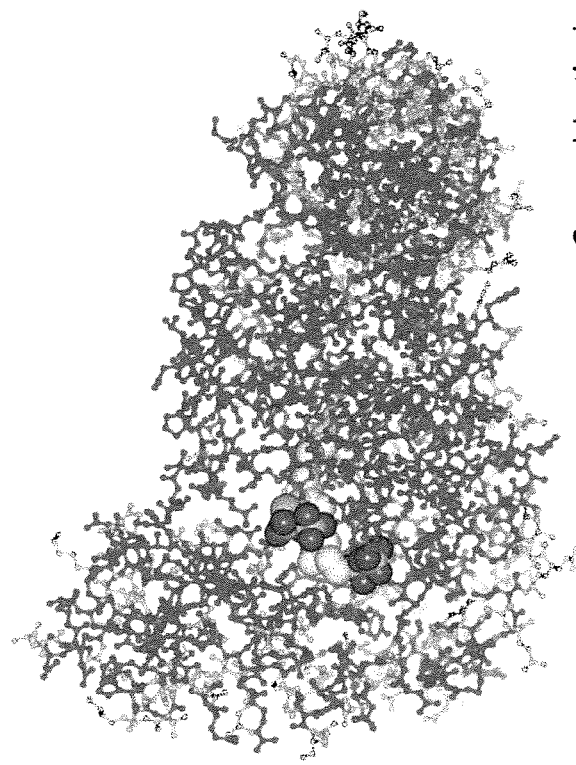
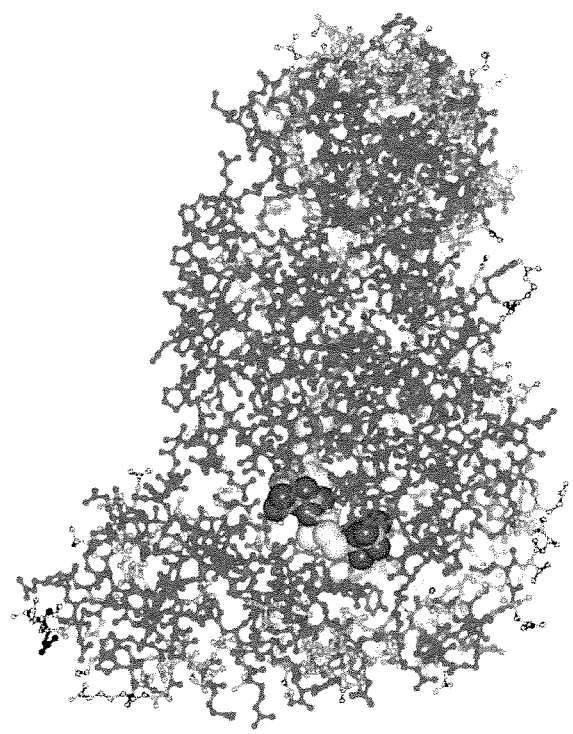
Green: Identical residues

Fig. 21

```
>>tr|Q8LII6|Q8LII6_PARZE                              (333 aa)
 initn: 1887 init1: 1859 opt: 1866  Z-score: 2009.0 bits: 380.1 E(5):  2.1e-109
Smith-Waterman score: 1866; 86.2% identity (95.2% similar) in 333 aa overlap (1-333:1-333)

10        20        30        40        50        60
EnzymC    MTVQDNVRKPMDRLSEALTAEMEAVNALIRDRMASRHAPRIPEVTAHLIEAGGKRLRPML
          :: ::::::::::::: ::::::::::::::::: :::::::::::::::::::::::::
Q8LII6    MNVQEDVRKPLDRLAEALAPEMEAVNALIRERMASRHAPRIPEVTAHLIEAGGKRLRPML
                  70        80        90       100       110       120

130       140       150       160       170       180
EnzymC    TLAAAKLLGYPGPWHVHLAATVEFIHTATLLHDDVVDESAQRRGRPTANLLWDNKSSVLV
          :::::::::: :: ::::::::::::::::::::::: :::::::::::::::::::::
Q8LII6    TLAAAKLLGYGGPYHVHLAATVEFIHTATLLHDDVVDESRQRRGRPTANLLWDNKSSVLV
                 130       140       150       160       170       180

190       200       210       220       230       240
EnzymC    GDYLFARSFQLMVEPGNLRTLEILANASATIAEGEVLQLTAAQDLATDESVYLQVVRGKT
          ::::::::::::::::: ::::::: :: ::::::::::::::::::: :::::::::
Q8LII6    GDYLFARSFQLMVEPGSMRTLEILSNAAATIAEGEVLQLTAAQDLATNEDIYLQVVRGKT
                 190       200       210       220       230       240

250       260       270       280       290       300
EnzymC    AALFSAATEVGGVIAGAPDDQVQALFDYGDALGISFQIVDDLLDYGGATETIGKNVGDDF
          ::::::::::::::::: ::::: ::::::::::: :::::::::::: :::::: ::
Q8LII6    AALFSAATEVGGVIAGVPDAQVRALFDYGDALGIAFQIVDDLLDYGGTAEAIDKNTGDDF
                 250       260       270       280       290       300

310       320       330
EnzymC    RERKLTLPVIKAIAKADAEERAFWTRTIEAGDQRDGDLEHALSLLARHGAMEAARADALA
          ::::::::::: ::: ::::::: ::::: :::::::::: ::::::::::: :::: :
Q8LII6    RERKLTLPVIKAVARATPEERAFWSRTIEKGDQKDGDLEHALELLLARHGAMADARRDALD
                 310       320       330

EnzymC    HAARARAALQVLPAHPIRDMLADLADFVVSRVA
          ::::::::  :: :::::::: :::::: ::
Q8LII6    WAARARASLQILPEHPIRDMLSDLADFVVERIA
```

EnzymC : Enzyme_C
Q8LII6 : Decaprenyl diphosphate synthase (Paracoccus zeaxanthinifaciens)

Fig. 22
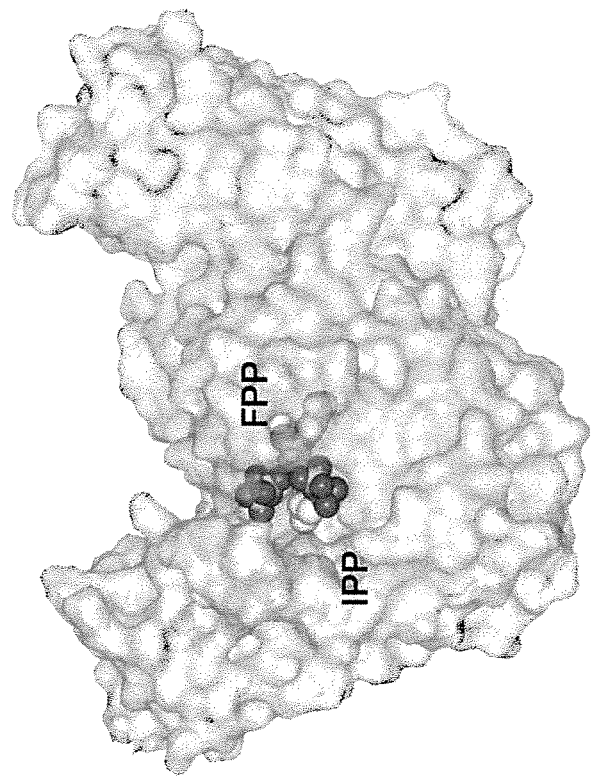
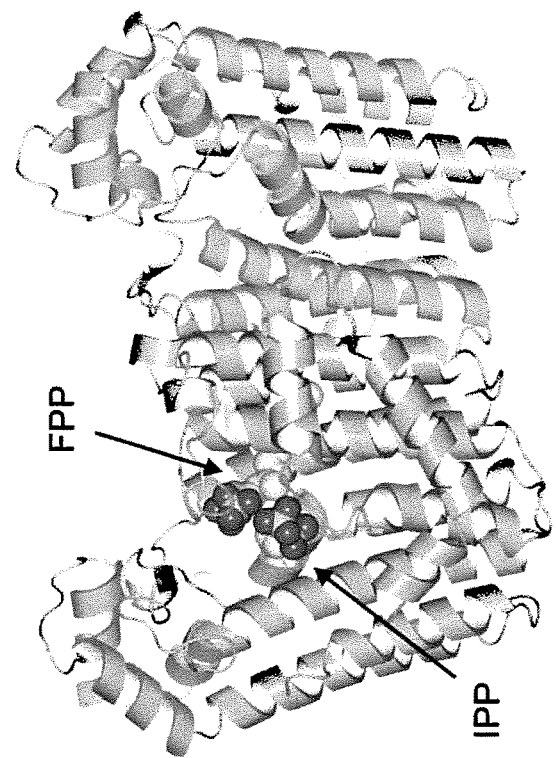

Fig. 26
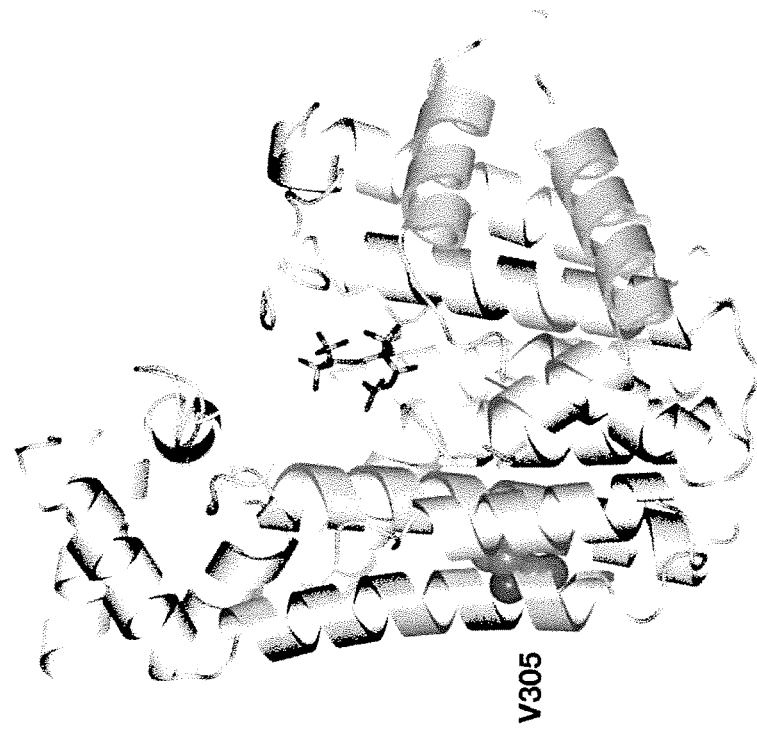
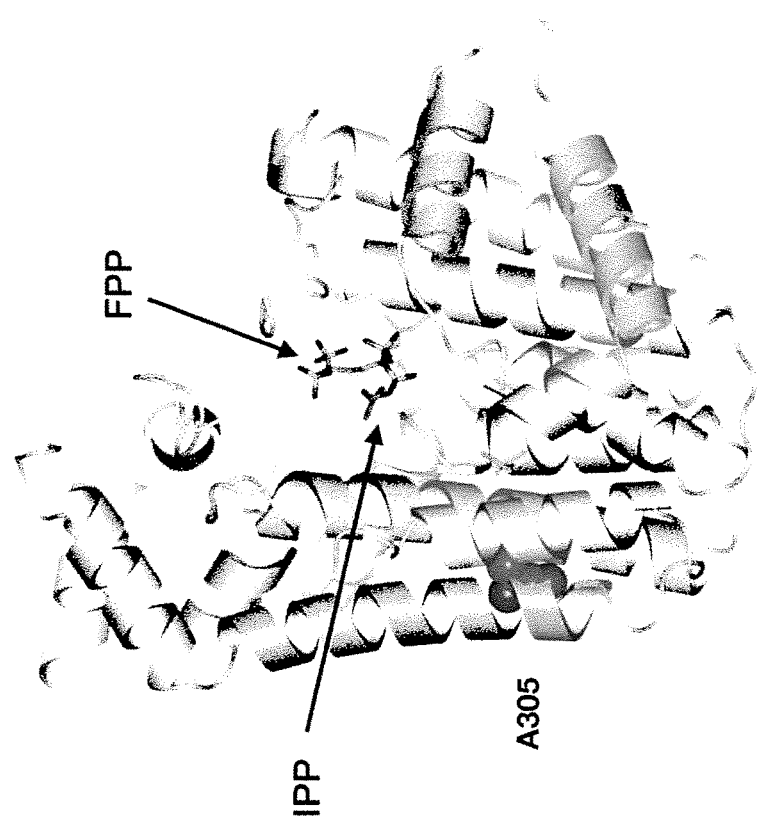

Fig. 29
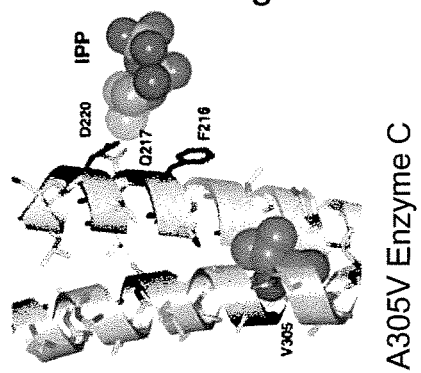
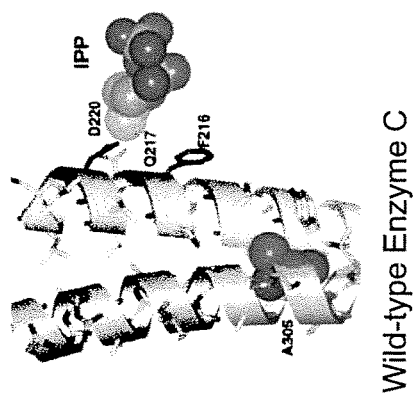
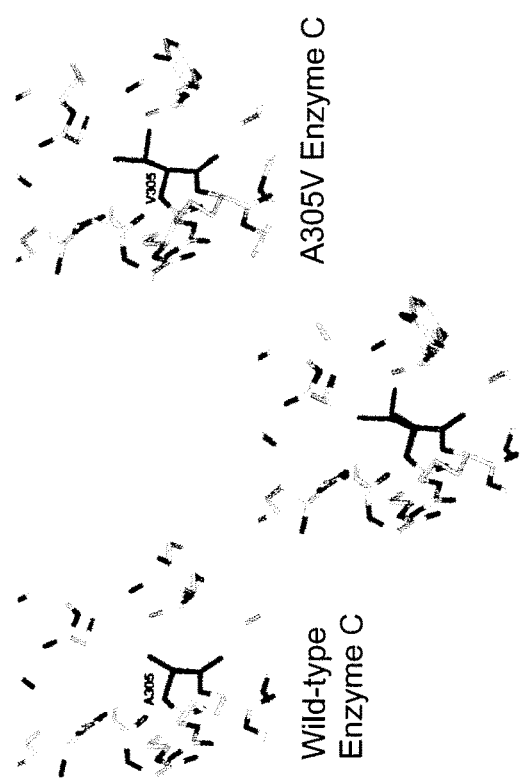

Fig. 32
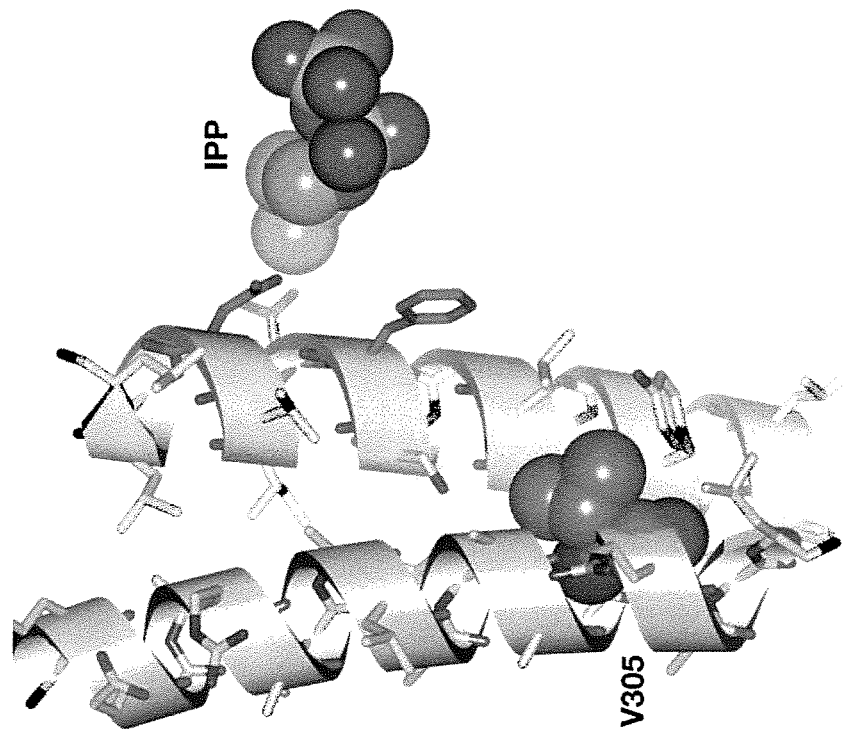
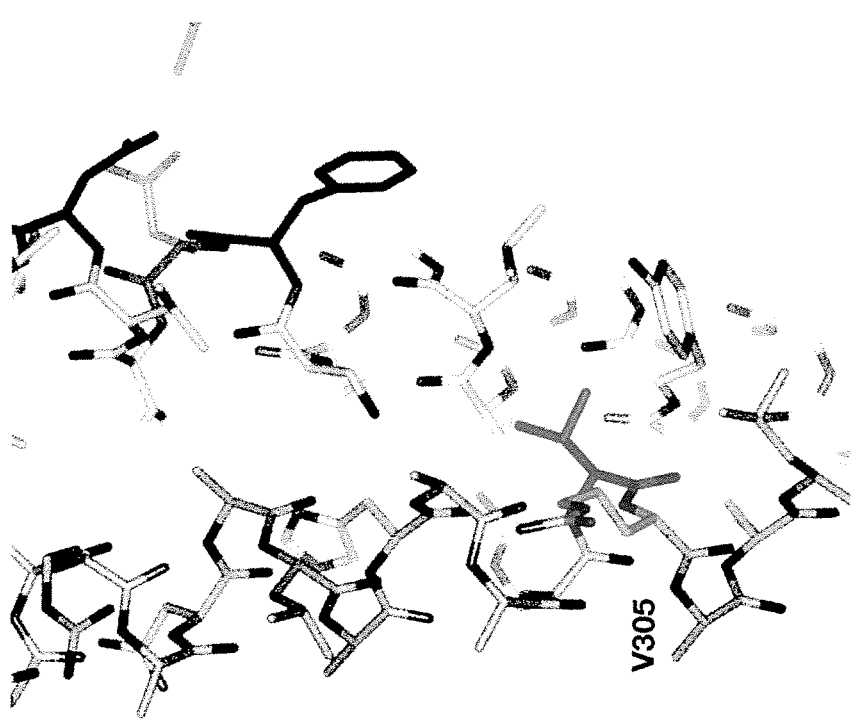

SEQUENCE LISTING

```
<160> NUMBER OF SEQ ID NOS: 9

<210> SEQ ID NO 1
<211> LENGTH: 1926
<212> TYPE: DNA
<213> ORGANISM: Paracoccus carotinifaciens
<220> FEATURE:
<221> NAME/KEY: CDS
<222> LOCATION: (1)..(1923)

<400> SEQUENCE: 1 atg acc gat cga ccc aag acg ccg att ctg gac cgc gtt agc ctg ccg       48
Met Thr Asp Arg Pro Lys Thr Pro Ile Leu Asp Arg Val Ser Leu Pro
1               5                   10                  15 tcg gat ctg aag acc ctg acc gac gcg caa ctg cgc cag ctt gcc gac       96
Ser Asp Leu Lys Thr Leu Thr Asp Ala Gln Leu Arg Gln Leu Ala Asp
                20                  25                  30 gag ttg cgg gcc gag acc atc agc gcc gtc agc gtg acc ggc ggc cat      144
Glu Leu Arg Ala Glu Thr Ile Ser Ala Val Ser Val Thr Gly Gly His
            35                  40                  45 ctg ggc gcg ggc ctg ggc gtg gtc gag ctg acc gta gcc ctg cat gcg      192
Leu Gly Ala Gly Leu Gly Val Val Glu Leu Thr Val Ala Leu His Ala
        50                  55                  60 gtc ttc gac acg ccg cgc gac aag ctg atc tgg gac gtg ggg cac cag      240
Val Phe Asp Thr Pro Arg Asp Lys Leu Ile Trp Asp Val Gly His Gln
65                  70                  75                  80 tgc tat ccg cac aag atc ctg acc ggg cgg cgc gat cgc atc cgc acg      288
Cys Tyr Pro His Lys Ile Leu Thr Gly Arg Arg Asp Arg Ile Arg Thr
                85                  90                  95 ctg cgc atg ggc ggg ggc ctt gcg ggg ttc acc aag cgc gcg gaa agc      336
Leu Arg Met Gly Gly Gly Leu Ala Gly Phe Thr Lys Arg Ala Glu Ser
            100                 105                 110 ccc tat gac ccg ttc ggg gcg ggg cat tcg tcg acc tcg atc agc gcg      384
Pro Tyr Asp Pro Phe Gly Ala Gly His Ser Ser Thr Ser Ile Ser Ala
        115                 120                 125 gcc ctg ggt ttc gcg atg gcg cgg gaa ctg ggc ggc gac ccg ggc gat      432
Ala Leu Gly Phe Ala Met Ala Arg Glu Leu Gly Gly Asp Pro Gly Asp
    130                 135                 140 gcg atc gcg gtc atc ggc gac ggc gcc atg agc gcc ggc atg gct tat      480
Ala Ile Ala Val Ile Gly Asp Gly Ala Met Ser Ala Gly Met Ala Tyr
145                 150                 155                 160 gaa gcg ctg aac aat gcg ggc cat gag ggc aag cgc ctg ttc gtg gtc      528
Glu Ala Leu Asn Asn Ala Gly His Glu Gly Lys Arg Leu Phe Val Val
                165                 170                 175 ctg aat gac aac gag atg tcc att gcg ccc ccg gtc ggc gcc atg tcc      576
Leu Asn Asp Asn Glu Met Ser Ile Ala Pro Pro Val Gly Ala Met Ser
            180                 185                 190
```

| | |
|---|---|
| tcc tat ctg acg cgc ctt tat gca ggc ggg ccg ttc cag gag ctg aag<br>Ser Tyr Leu Thr Arg Leu Tyr Ala Gly Gly Pro Phe Gln Glu Leu Lys<br>               195                            200                    205 | 624 |
| gcg gtg gcc aag ggc gcc gtt ggc atg ctg ccg gac gcc ctg cag gag<br>Ala Val Ala Lys Gly Ala Val Gly Met Leu Pro Asp Ala Leu Gln Glu<br>210                            215                          220 | 672 |
| ggc gcg cgc cgc gcc aag gag atg ctg aag ggc atg gcc gtg ggc ggc<br>Gly Ala Arg Arg Ala Lys Glu Met Leu Lys Gly Met Ala Val Gly Gly<br>225                        230                        235                    240 | 720 |
| acc ctg ttc gag gag ctg ggc ttt tcc tat atc ggg ccg gtc gac ggt<br>Thr Leu Phe Glu Glu Leu Gly Phe Ser Tyr Ile Gly Pro Val Asp Gly<br>                            245                        250                    255 | 768 |
| cac gac atg gaa cag ctg ctg ccc ctg ctg cgc acc gtg cgg gcg cgg<br>His Asp Met Glu Gln Leu Leu Pro Leu Leu Arg Thr Val Arg Ala Arg<br>                    260                        265                        270 | 816 |
| gcc gac ggt ccg gtc ctg atc cac gtc gtg acc aag aag ggc aag ggt<br>Ala Asp Gly Pro Val Leu Ile His Val Val Thr Lys Lys Gly Lys Gly<br>                275                        280                        285 | 864 |
| tat gcc ccg gcc gag gcg gcc gcg gac aag ggc cat gcc acc gcc aag<br>Tyr Ala Pro Ala Glu Ala Ala Ala Asp Lys Gly His Ala Thr Ala Lys<br>                    290                        295                    300 | 912 |
| ttc gac gtg atc acc ggc gtg cag gcc aag gcg aaa tcg aac gcg ccc<br>Phe Asp Val Ile Thr Gly Val Gln Ala Lys Ala Lys Ser Asn Ala Pro<br>305                        310                        315                    320 | 960 |
| agc tat acc gcc gtc ttc gcg cag gcg ctg atc gat cag gcg ggg cgt<br>Ser Tyr Thr Ala Val Phe Ala Gln Ala Leu Ile Asp Gln Ala Gly Arg<br>                        325                        330                    335 | 1008 |
| gac gac cgc atc ctg ggg gtg acc gcc gcg atg ccg gac ggg acc ggc<br>Asp Asp Arg Ile Leu Gly Val Thr Ala Ala Met Pro Asp Gly Thr Gly<br>                    340                        345                    350 | 1056 |
| ctc aag cag ttc gcg cag cgc ttt ccg cgc cgc tgc ttc gac gtg ggc<br>Leu Lys Gln Phe Ala Gln Arg Phe Pro Arg Arg Cys Phe Asp Val Gly<br>                355                        360                    365 | 1104 |
| att gcc gaa cag cat gcc gtg acc ttt gcc gcc ggt ctg gcc gcg gga<br>Ile Ala Glu Gln His Ala Val Thr Phe Ala Ala Gly Leu Ala Ala Gly<br>370                        375                        380 | 1152 |
| ggc atg aag cct ttc gtc gcg atc tat tcg acc ttt ctg cag cgc ggc<br>Gly Met Lys Pro Phe Val Ala Ile Tyr Ser Thr Phe Leu Gln Arg Gly<br>385                        390                        395                    400 | 1200 |
| tat gac cag atc gtg cat gac gtc gcg gtc cag aac ctg ccc gtc cgg<br>Tyr Asp Gln Ile Val His Asp Val Ala Val Gln Asn Leu Pro Val Arg<br>                    405                        410                    415 | 1248 |
| ttc gcc gtc gac cgt gcc ggg ctg gtg ggc cag gac ggt ccg acc cat<br>Phe Ala Val Asp Arg Ala Gly Leu Val Gly Gln Asp Gly Pro Thr His<br>                        420                        425                    430 | 1296 |
| tcc ggc gcc tat gac acc gcc ttc ctg gcc aat ctg ccc ggg ttt gtc<br>Ser Gly Ala Tyr Asp Thr Ala Phe Leu Ala Asn Leu Pro Gly Phe Val<br>                    435                        440                    445 | 1344 |
| gtc atg gcc gcc gcg gac gag gcc gaa ctg gcc cac atg gtc gcc acg<br>Val Met Ala Ala Ala Asp Glu Ala Glu Leu Ala His Met Val Ala Thr<br>450                        455                        460 | 1392 |
| gcc gcc gca cat gac agc ggc ccc atc gcc ttc cgc ttt ccg cgc gga<br>Ala Ala Ala His Asp Ser Gly Pro Ile Ala Phe Arg Phe Pro Arg Gly<br>465                        470                        475                    480 | 1440 |
| gag ggc acc ggg gtc gag atg ccc gag cgc ggg cag gtc ctg ccc atc<br>Glu Gly Thr Gly Val Glu Met Pro Glu Arg Gly Gln Val Leu Pro Ile<br>                        485                        490                    495 | 1488 |
| ggc aag ggc cgc atg atc gcg gag ggc aag ggc gtc gcc atc ctg tcc<br>Gly Lys Gly Arg Met Ile Ala Glu Gly Lys Gly Val Ala Ile Leu Ser | 1536 |

```
                        500                 505                 510
ttc ggc acg cgc ctg tcc gag gtg atg acc gcg cgc gag gcg ctg atg        1584
Phe Gly Thr Arg Leu Ser Glu Val Met Thr Ala Arg Glu Ala Leu Met
            515                 520                 525 gcg cgg ggc atc acg ccc acg gtc gcc gac gcg cgc ttt gcc aag ccg        1632
Ala Arg Gly Ile Thr Pro Thr Val Ala Asp Ala Arg Phe Ala Lys Pro
        530                 535                 540 ctg gat cgt gac ctg atc ctg gca ctg gcc cgc gat cac gag gcg ctg        1680
Leu Asp Arg Asp Leu Ile Leu Ala Leu Ala Arg Asp His Glu Ala Leu
545                 550                 555                 560 atc acc atc gag gag ggc gcc gtg ggc ggt ttc ggc agc cat gtc gcc        1728
Ile Thr Ile Glu Glu Gly Ala Val Gly Gly Phe Gly Ser His Val Ala
                565                 570                 575 cat ctg ctg gcc gag gag ggc gcc ttc gac aag ggg ctg cgc ttc cgg        1776
His Leu Leu Ala Glu Glu Gly Ala Phe Asp Lys Gly Leu Arg Phe Arg
            580                 585                 590 tcg atg gtc ctg ccg gat gcg ttc gtc gac cac gac gcg ccg cgg gcg        1824
Ser Met Val Leu Pro Asp Ala Phe Val Asp His Asp Ala Pro Arg Ala
        595                 600                 605 atg tat gac agc agc tgc ctg aac gcc cag cat atc gag gac aag gtc        1872
Met Tyr Asp Ser Ser Cys Leu Asn Ala Gln His Ile Glu Asp Lys Val
610                 615                 620 ctc tcc gtg atg ggc gtc cag tcg ctc gcg gcg cgg cgc acc gac cgc        1920
Leu Ser Val Met Gly Val Gln Ser Leu Ala Ala Arg Arg Thr Asp Arg
625                 630                 635                 640 gcc tga                                                                 1926
Ala <210> SEQ ID NO 2
<211> LENGTH: 641
<212> TYPE: PRT
<213> ORGANISM: Paracoccus carotinifaciens

<400> SEQUENCE: 2

Met Thr Asp Arg Pro Lys Thr Pro Ile Leu Asp Arg Val Ser Leu Pro
1               5                   10                  15

Ser Asp Leu Lys Thr Leu Thr Asp Ala Gln Leu Arg Gln Leu Ala Asp
            20                  25                  30

Glu Leu Arg Ala Glu Thr Ile Ser Ala Val Ser Val Thr Gly Gly His
        35                  40                  45

Leu Gly Ala Gly Leu Gly Val Val Glu Leu Thr Val Ala Leu His Ala
    50                  55                  60

Val Phe Asp Thr Pro Arg Asp Lys Leu Ile Trp Asp Val Gly His Gln
65                  70                  75                  80

Cys Tyr Pro His Lys Ile Leu Thr Gly Arg Arg Asp Arg Ile Arg Thr
                85                  90                  95

Leu Arg Met Gly Gly Gly Leu Ala Gly Phe Thr Lys Arg Ala Glu Ser
            100                 105                 110

Pro Tyr Asp Pro Phe Gly Ala Gly His Ser Ser Thr Ser Ile Ser Ala
        115                 120                 125

Ala Leu Gly Phe Ala Met Ala Arg Glu Leu Gly Gly Asp Pro Gly Asp
    130                 135                 140

Ala Ile Ala Val Ile Gly Asp Gly Ala Met Ser Ala Gly Met Ala Tyr
145                 150                 155                 160

Glu Ala Leu Asn Asn Ala Gly His Glu Gly Lys Arg Leu Phe Val Val
                165                 170                 175

Leu Asn Asp Asn Glu Met Ser Ile Ala Pro Pro Val Gly Ala Met Ser
```

-continued

```
                180                 185                 190
    Ser Tyr Leu Thr Arg Leu Tyr Ala Gly Gly Pro Phe Gln Glu Leu Lys
                    195                 200                 205

Ala Val Ala Lys Gly Ala Val Gly Met Leu Pro Asp Ala Leu Gln Glu
    210                 215                 220

Gly Ala Arg Arg Ala Lys Glu Met Leu Lys Gly Met Ala Val Gly Gly
    225                 230                 235                 240

Thr Leu Phe Glu Glu Leu Gly Phe Ser Tyr Ile Gly Pro Val Asp Gly
                    245                 250                 255

His Asp Met Glu Gln Leu Leu Pro Leu Leu Arg Thr Val Arg Ala Arg
                    260                 265                 270

Ala Asp Gly Pro Val Leu Ile His Val Val Thr Lys Lys Gly Lys Gly
                275                 280                 285

Tyr Ala Pro Ala Glu Ala Ala Asp Lys Gly His Ala Thr Ala Lys
                290                 295                 300

Phe Asp Val Ile Thr Gly Val Gln Ala Lys Ala Lys Ser Asn Ala Pro
    305                 310                 315                 320

Ser Tyr Thr Ala Val Phe Ala Gln Ala Leu Ile Asp Gln Ala Gly Arg
                    325                 330                 335

Asp Asp Arg Ile Leu Gly Val Thr Ala Ala Met Pro Asp Gly Thr Gly
                    340                 345                 350

Leu Lys Gln Phe Ala Gln Arg Phe Pro Arg Arg Cys Phe Asp Val Gly
                355                 360                 365

Ile Ala Glu Gln His Ala Val Thr Phe Ala Ala Gly Leu Ala Ala Gly
                370                 375                 380

Gly Met Lys Pro Phe Val Ala Ile Tyr Ser Thr Phe Leu Gln Arg Gly
    385                 390                 395                 400

Tyr Asp Gln Ile Val His Asp Val Ala Val Gln Asn Leu Pro Val Arg
                    405                 410                 415

Phe Ala Val Asp Arg Ala Gly Leu Val Gly Gln Asp Gly Pro Thr His
                    420                 425                 430

Ser Gly Ala Tyr Asp Thr Ala Phe Leu Ala Asn Leu Pro Gly Phe Val
                435                 440                 445

Val Met Ala Ala Ala Asp Glu Ala Glu Leu Ala His Met Val Ala Thr
    450                 455                 460

Ala Ala Ala His Asp Ser Gly Pro Ile Ala Phe Arg Phe Pro Arg Gly
    465                 470                 475                 480

Glu Gly Thr Gly Val Glu Met Pro Glu Arg Gly Gln Val Leu Pro Ile
                    485                 490                 495

Gly Lys Gly Arg Met Ile Ala Glu Gly Lys Gly Val Ala Ile Leu Ser
                    500                 505                 510

Phe Gly Thr Arg Leu Ser Glu Val Met Thr Ala Arg Glu Ala Leu Met
                515                 520                 525

Ala Arg Gly Ile Thr Pro Thr Val Ala Asp Ala Arg Phe Ala Lys Pro
                530                 535                 540

Leu Asp Arg Asp Leu Ile Leu Ala Leu Ala Arg Asp His Glu Ala Leu
    545                 550                 555                 560

Ile Thr Ile Glu Glu Gly Ala Val Gly Gly Phe Gly Ser His Val Ala
                    565                 570                 575

His Leu Leu Ala Glu Glu Gly Ala Phe Asp Lys Gly Leu Arg Phe Arg
                    580                 585                 590

Ser Met Val Leu Pro Asp Ala Phe Val Asp His Asp Ala Pro Arg Ala
                595                 600                 605
```

```
Met Tyr Asp Ser Ser Cys Leu Asn Ala Gln His Ile Glu Asp Lys Val
            610                 615                 620

Leu Ser Val Met Gly Val Gln Ser Leu Ala Ala Arg Arg Thr Asp Arg
625                 630                 635                 640

Ala

<210> SEQ ID NO 3
<211> LENGTH: 1002
<212> TYPE: DNA
<213> ORGANISM: Paracoccus carotinifaciens
<220> FEATURE:
<221> NAME/KEY: CDS
<222> LOCATION: (1)..(999)

<400> SEQUENCE: 3 atg act gtg cag gac aac gtc cgc aaa ccg atg gat cgg ctg agc gag        48
Met Thr Val Gln Asp Asn Val Arg Lys Pro Met Asp Arg Leu Ser Glu
1               5                   10                  15 gcc ctg acc gcc gag atg gag gcg gtc aac gcg ctg atc cgc gac cgc        96
Ala Leu Thr Ala Glu Met Glu Ala Val Asn Ala Leu Ile Arg Asp Arg
                20                  25                  30 atg gcc agc cgc cat gcc ccc cgc atc ccc gag gtg acg gcg cat ctg       144
Met Ala Ser Arg His Ala Pro Arg Ile Pro Glu Val Thr Ala His Leu
            35                  40                  45 atc gag gcc ggc ggc aag cgc ctg cgc ccg atg ctg acg ctg gcc gcg       192
Ile Glu Ala Gly Gly Lys Arg Leu Arg Pro Met Leu Thr Leu Ala Ala
        50                  55                  60 gcc aag ctg ctg ggc tat ccc ggc ccg tgg cat gtc cac ctg gcc gcc       240
Ala Lys Leu Leu Gly Tyr Pro Gly Pro Trp His Val His Leu Ala Ala
65                  70                  75                  80 acg gtc gaa ttc atc cat acc gcc acg ctg ctg cat gac gac gtg gtc       288
Thr Val Glu Phe Ile His Thr Ala Thr Leu Leu His Asp Asp Val Val
                85                  90                  95 gac gaa agc gcg cag cgg cgc ggg cgc ccg acg gcg aac ctg ctg tgg       336
Asp Glu Ser Ala Gln Arg Arg Gly Arg Pro Thr Ala Asn Leu Leu Trp
            100                 105                 110 gac aac aag tcc agc gtg ctg gtc gga gat tac ctg ttc gcg cgc agc       384
Asp Asn Lys Ser Ser Val Leu Val Gly Asp Tyr Leu Phe Ala Arg Ser
        115                 120                 125 ttt cag ctg atg gtc gaa ccc ggc aac ctg cga acg ctg gag atc ctg       432
Phe Gln Leu Met Val Glu Pro Gly Asn Leu Arg Thr Leu Glu Ile Leu
    130                 135                 140 gcc aat gcc agc gcc acc atc gcc gag ggc gag gtg ctg cag ctg acc       480
Ala Asn Ala Ser Ala Thr Ile Ala Glu Gly Glu Val Leu Gln Leu Thr
145                 150                 155                 160 gcg gcg cag gac ctg gcg acc gac gaa tcc gtc tat ctg cag gtg gtg       528
Ala Ala Gln Asp Leu Ala Thr Asp Glu Ser Val Tyr Leu Gln Val Val
                165                 170                 175 cgc ggc aag acg gcg gcg ctg ttt tcc gcc gcg acc gag gtg ggc ggc       576
Arg Gly Lys Thr Ala Ala Leu Phe Ser Ala Ala Thr Glu Val Gly Gly
            180                 185                 190 gtc atc gcc ggt gcg ccc gac gat cag gtg cag gcg ctg ttc gat tac       624
Val Ile Ala Gly Ala Pro Asp Asp Gln Val Gln Ala Leu Phe Asp Tyr
        195                 200                 205 ggc gac gcc ctg ggc atc agc ttc cag att gtc gac gac ctg ctg gat       672
Gly Asp Ala Leu Gly Ile Ser Phe Gln Ile Val Asp Asp Leu Leu Asp
    210                 215                 220 tac ggc ggc gcg acc gag acg atc ggc aag aac gtg ggc gac gat ttc       720
Tyr Gly Gly Ala Thr Glu Thr Ile Gly Lys Asn Val Gly Asp Asp Phe
225                 230                 235                 240
```

```
cgc gaa cgc aag ctg acc ctg ccg gtc atc aag gcc atc gcc aag gcc      768
Arg Glu Arg Lys Leu Thr Leu Pro Val Ile Lys Ala Ile Ala Lys Ala
                245                 250                 255 gac gcc gag gaa cgc gcc ttc tgg acc cgc acc atc gag gcg ggc gac      816
Asp Ala Glu Glu Arg Ala Phe Trp Thr Arg Thr Ile Glu Ala Gly Asp
            260                 265                 270 cag cgc gac ggc gac ctg gag cac gcg ctg tcg ctg ctg gcc cgt cac      864
Gln Arg Asp Gly Asp Leu Glu His Ala Leu Ser Leu Leu Ala Arg His
        275                 280                 285 ggt gcg atg gag gcc gcg cgc gcc gat gcg ctg gcc cat gcc gca cgg      912
Gly Ala Met Glu Ala Ala Arg Ala Asp Ala Leu Ala His Ala Ala Arg
    290                 295                 300 gcc cgc gcg gcg ctg cag gtg ctg ccc gcg cat ccg att cgc gac atg      960
Ala Arg Ala Ala Leu Gln Val Leu Pro Ala His Pro Ile Arg Asp Met
305                 310                 315                 320 ctg gcc gac ctc gcg gat ttc gtc gtc agc cgc gtg gcc tga             1002
Leu Ala Asp Leu Ala Asp Phe Val Val Ser Arg Val Ala
                325                 330
```

<210> SEQ ID NO 4
<211> LENGTH: 333
<212> TYPE: PRT
<213> ORGANISM: Paracoccus carotinifaciens

<400> SEQUENCE: 4

```
Met Thr Val Gln Asp Asn Val Arg Lys Pro Met Asp Arg Leu Ser Glu
1               5                   10                  15

Ala Leu Thr Ala Glu Met Glu Ala Val Asn Ala Leu Ile Arg Asp Arg
            20                  25                  30

Met Ala Ser Arg His Ala Pro Arg Ile Pro Glu Val Thr Ala His Leu
        35                  40                  45

Ile Glu Ala Gly Gly Lys Arg Leu Arg Pro Met Leu Thr Leu Ala Ala
    50                  55                  60

Ala Lys Leu Leu Gly Tyr Pro Gly Pro Trp His Val His Leu Ala Ala
65                  70                  75                  80

Thr Val Glu Phe Ile His Thr Ala Thr Leu Leu His Asp Asp Val Val
                85                  90                  95

Asp Glu Ser Ala Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ser
        115                 120                 125

Phe Gln Leu Met Val Glu Pro Gly Asn Leu Arg Thr Leu Glu Ile Leu
    130                 135                 140

Ala Asn Ala Ser Ala Thr Ile Ala Glu Gly Glu Val Leu Gln Leu Thr
145                 150                 155                 160

Ala Ala Gln Asp Leu Ala Thr Asp Glu Ser Val Tyr Leu Gln Val Val
                165                 170                 175

Arg Gly Lys Thr Ala Ala Leu Phe Ser Ala Ala Thr Glu Val Gly Gly
            180                 185                 190

Val Ile Ala Gly Ala Pro Asp Asp Gln Val Gln Ala Leu Phe Asp Tyr
        195                 200                 205

Gly Asp Ala Leu Gly Ile Ser Phe Gln Ile Val Asp Asp Leu Leu Asp
    210                 215                 220

Tyr Gly Gly Ala Thr Glu Thr Ile Gly Lys Asn Val Gly Asp Asp Phe
225                 230                 235                 240

Arg Glu Arg Lys Leu Thr Leu Pro Val Ile Lys Ala Ile Ala Lys Ala
```

```
                    245                 250                 255
Asp Ala Glu Glu Arg Ala Phe Trp Thr Arg Thr Ile Glu Ala Gly Asp
                260                 265                 270

Gln Arg Asp Gly Asp Leu Glu His Ala Leu Ser Leu Leu Ala Arg His
            275                 280                 285

Gly Ala Met Glu Ala Ala Arg Ala Asp Ala Leu Ala His Ala Ala Arg
        290                 295                 300

Ala Arg Ala Ala Leu Gln Val Leu Pro Ala His Pro Ile Arg Asp Met
305                 310                 315                 320

Leu Ala Asp Leu Ala Asp Phe Val Val Ser Arg Val Ala
                325                 330

<210> SEQ ID NO 5
<211> LENGTH: 1926
<212> TYPE: DNA
<213> ORGANISM: Paracoccus carotinifaciens
<220> FEATURE:
<221> NAME/KEY: CDS
<222> LOCATION: (1)..(1923)

<400> SEQUENCE: 5 atg acc gat cga ccc aag acg ccg att ctg gac cgc gtt agc ctg ccg      48
Met Thr Asp Arg Pro Lys Thr Pro Ile Leu Asp Arg Val Ser Leu Pro
1               5                   10                  15 tcg gat ctg aag acc ctg acc gac gcg caa ctg cgc cag ctt gcc gac      96
Ser Asp Leu Lys Thr Leu Thr Asp Ala Gln Leu Arg Gln Leu Ala Asp
            20                  25                  30 gag ttg cgg gcc gag acc atc agc gcc gtc agc gtg acc ggc ggc cat     144
Glu Leu Arg Ala Glu Thr Ile Ser Ala Val Ser Val Thr Gly Gly His
        35                  40                  45 ctg ggc gcg ggc ctg ggc gtg gtc gag ctg acc gta gcc ctg cat gcg     192
Leu Gly Ala Gly Leu Gly Val Val Glu Leu Thr Val Ala Leu His Ala
    50                  55                  60 gtc ttc gac acg ccg cgc gac aag ctg atc tgg gac gtg ggc cac cag     240
Val Phe Asp Thr Pro Arg Asp Lys Leu Ile Trp Asp Val Gly His Gln
65                  70                  75                  80 tgc tat ccg cac aag atc ctg acc ggg cgg cgc gat cgc atc cgc acg     288
Cys Tyr Pro His Lys Ile Leu Thr Gly Arg Arg Asp Arg Ile Arg Thr
                85                  90                  95 ctg cgc atg ggc ggg ggc ctt gcg ggg ttc acc aag cgc gcg gaa agc     336
Leu Arg Met Gly Gly Gly Leu Ala Gly Phe Thr Lys Arg Ala Glu Ser
            100                 105                 110 ccc tat gac ccg ttc ggg gcg ggg cat tcg tcg acc tcg atc agc gcg     384
Pro Tyr Asp Pro Phe Gly Ala Gly His Ser Ser Thr Ser Ile Ser Ala
        115                 120                 125 gcc ctg ggt ttc gcg atg gcg cgg gaa ctg ggc ggc gac ccg ggc gat     432
Ala Leu Gly Phe Ala Met Ala Arg Glu Leu Gly Gly Asp Pro Gly Asp
    130                 135                 140 gcg atc gcg gtc atc ggc gac ggc gcc atg agc gcc ggc atg gct tat     480
Ala Ile Ala Val Ile Gly Asp Gly Ala Met Ser Ala Gly Met Ala Tyr
145                 150                 155                 160 gaa gcg ctg aac aat gcg ggc cat gag ggc aag cgc ctg ttc gtg gtc     528
Glu Ala Leu Asn Asn Ala Gly His Glu Gly Lys Arg Leu Phe Val Val
                165                 170                 175 ctg aat gac aac gag atg tcc att gcg ccc ccg gtc ggc gcc atg tcc     576
Leu Asn Asp Asn Glu Met Ser Ile Ala Pro Pro Val Gly Ala Met Ser
            180                 185                 190 tcc tat ctg acg cgc ctt tat gca ggc ggg ccg ttc cag gag ctg aag     624
Ser Tyr Leu Thr Arg Leu Tyr Ala Gly Gly Pro Phe Gln Glu Leu Lys
        195                 200                 205
```

```
gcg gtg gcc aag ggc gcc gtt ggc atg ctg ccg gac gcc ctg cag gag      672
Ala Val Ala Lys Gly Ala Val Gly Met Leu Pro Asp Ala Leu Gln Glu
    210             215                 220 gac gcg cgc cgc gcc aag gag atg ctg aag ggc atg gcc gtg ggc ggc      720
Asp Ala Arg Arg Ala Lys Glu Met Leu Lys Gly Met Ala Val Gly Gly
225             230                 235                 240 acc ctg ttc gag gag ctg ggc ttt tcc tat atc ggg ccg gtc gac ggt      768
Thr Leu Phe Glu Glu Leu Gly Phe Ser Tyr Ile Gly Pro Val Asp Gly
                245                 250                 255 cac gac atg gaa cag ctg ctg ccc ctg ctg cgc acc gtg cgg gcg cgg      816
His Asp Met Glu Gln Leu Leu Pro Leu Leu Arg Thr Val Arg Ala Arg
            260                 265                 270 gcc gac ggt ccg gtc ctg atc cac gtc gtg acc aag aag ggc aag ggt      864
Ala Asp Gly Pro Val Leu Ile His Val Val Thr Lys Lys Gly Lys Gly
        275                 280                 285 tat gcc ccg gcc gag gcg gcc gcg gac aag ggc cat gcc acc gcc aag      912
Tyr Ala Pro Ala Glu Ala Ala Ala Asp Lys Gly His Ala Thr Ala Lys
    290                 295                 300 ttc gac gtg atc acc ggc gtg cag gcc aag gcg aaa tcg aac gcg ccc      960
Phe Asp Val Ile Thr Gly Val Gln Ala Lys Ala Lys Ser Asn Ala Pro
305             310                 315                 320 agc tat acc gcc gtc ttc gcg cag gcg ctg atc gat cag gcg ggg cgt     1008
Ser Tyr Thr Ala Val Phe Ala Gln Ala Leu Ile Asp Gln Ala Gly Arg
                325                 330                 335 gac gac cgc atc ctg ggg gtg acc gcc gcg atg ccg gac ggg acc ggc     1056
Asp Asp Arg Ile Leu Gly Val Thr Ala Ala Met Pro Asp Gly Thr Gly
            340                 345                 350 ctc aag cag ttc gcg cag cgc ttt ccg cgc cgc tgc ttc gac gtg ggc     1104
Leu Lys Gln Phe Ala Gln Arg Phe Pro Arg Arg Cys Phe Asp Val Gly
        355                 360                 365 att gcc gaa cag cat gcc gtg acc ttt gcc gcc ggt ctg gcc gcg gga     1152
Ile Ala Glu Gln His Ala Val Thr Phe Ala Ala Gly Leu Ala Ala Gly
    370                 375                 380 ggc atg aag cct ttc gtc gcg atc tat tcg acc ttt ctg cag cgc ggc     1200
Gly Met Lys Pro Phe Val Ala Ile Tyr Ser Thr Phe Leu Gln Arg Gly
385             390                 395                 400 tat gac cag atc gtg cat gac gtc gcg gtc cag aac ctg ccc gtc cgg     1248
Tyr Asp Gln Ile Val His Asp Val Ala Val Gln Asn Leu Pro Val Arg
                405                 410                 415 ttc gcc gtc gac cgt gcc ggg ctg gtg ggc cag gac ggt ccg acc cat     1296
Phe Ala Val Asp Arg Ala Gly Leu Val Gly Gln Asp Gly Pro Thr His
            420                 425                 430 tcc ggc gcc tat gac acc gcc ttc ctg gcc aat ctg ccc ggg ttt gtc     1344
Ser Gly Ala Tyr Asp Thr Ala Phe Leu Ala Asn Leu Pro Gly Phe Val
        435                 440                 445 gtc atg gcc gcc gcg gac gag gcc gaa ctg gcc cac atg gtc gcc acg     1392
Val Met Ala Ala Ala Asp Glu Ala Glu Leu Ala His Met Val Ala Thr
    450                 455                 460 gcc gcc gca cat gac agc ggc ccc atc gcc ttc gct ttt ccg cgc gga     1440
Ala Ala Ala His Asp Ser Gly Pro Ile Ala Phe Arg Phe Pro Arg Gly
465             470                 475                 480 gag ggc acc ggg gtc gag atg ccc gag cgc ggg cag gtc ctg ccc atc     1488
Glu Gly Thr Gly Val Glu Met Pro Glu Arg Gly Gln Val Leu Pro Ile
                485                 490                 495 ggc aag ggc cgc atg atc gcg gag ggc aag ggc gtc gcc atc ctg tcc     1536
Gly Lys Gly Arg Met Ile Ala Glu Gly Lys Gly Val Ala Ile Leu Ser
            500                 505                 510 ttc ggc acg cgc ctg tcc gag gtg atg acc gcg cgc gag gcg ctg atg     1584
Phe Gly Thr Arg Leu Ser Glu Val Met Thr Ala Arg Glu Ala Leu Met
```

```
                515                 520                 525
gcg cgg ggc atc acg ccc acg gtc gcc gac gcg cgc ttt gcc aag ccg      1632
Ala Arg Gly Ile Thr Pro Thr Val Ala Asp Ala Arg Phe Ala Lys Pro
    530                 535                 540 ctg gat cgt gac ctg atc ctg gca ctg gcc cgc gat cac gag gcg ctg      1680
Leu Asp Arg Asp Leu Ile Leu Ala Leu Ala Arg Asp His Glu Ala Leu
545                 550                 555                 560 atc acc atc gag gag ggc gcc gtg ggc ggt ttc ggc agc cat gtc gcc      1728
Ile Thr Ile Glu Glu Gly Ala Val Gly Gly Phe Gly Ser His Val Ala
                565                 570                 575 cat ctg ctg gcc gag gag ggc gcc ttc gac aag ggg ctg cgc ttc cgg      1776
His Leu Leu Ala Glu Glu Gly Ala Phe Asp Lys Gly Leu Arg Phe Arg
            580                 585                 590 tcg atg gtc ctg ccg gat gcg ttc gtc gac cac gac gcg ccg cgg gcg      1824
Ser Met Val Leu Pro Asp Ala Phe Val Asp His Asp Ala Pro Arg Ala
        595                 600                 605 atg tat gac agc agc tgc ctg aac gcc cag cat atc gag gac aag gtc      1872
Met Tyr Asp Ser Ser Cys Leu Asn Ala Gln His Ile Glu Asp Lys Val
    610                 615                 620 ctc tcc gtg atg ggc gtc cag tcg ctc gcg gcg cgg cgc acc gac cgc      1920
Leu Ser Val Met Gly Val Gln Ser Leu Ala Ala Arg Arg Thr Asp Arg
625                 630                 635                 640 gcc tga                                                               1926
Ala
```

<210> SEQ ID NO 6
<211> LENGTH: 641
<212> TYPE: PRT
<213> ORGANISM: Paracoccus carotinifaciens

<400> SEQUENCE: 6

```
Met Thr Asp Arg Pro Lys Thr Pro Ile Leu Asp Arg Val Ser Leu Pro
1               5                   10                  15

Ser Asp Leu Lys Thr Leu Thr Asp Ala Gln Leu Arg Gln Leu Ala Asp
            20                  25                  30

Glu Leu Arg Ala Glu Thr Ile Ser Ala Val Ser Val Thr Gly Gly His
        35                  40                  45

Leu Gly Ala Gly Leu Gly Val Val Glu Leu Thr Val Ala Leu His Ala
    50                  55                  60

Val Phe Asp Thr Pro Arg Asp Lys Leu Ile Trp Asp Val Gly His Gln
65                  70                  75                  80

Cys Tyr Pro His Lys Ile Leu Thr Gly Arg Arg Asp Arg Ile Arg Thr
                85                  90                  95

Leu Arg Met Gly Gly Gly Leu Ala Gly Phe Thr Lys Arg Ala Glu Ser
            100                 105                 110

Pro Tyr Asp Pro Phe Gly Ala Gly His Ser Ser Thr Ser Ile Ser Ala
        115                 120                 125

Ala Leu Gly Phe Ala Met Ala Arg Glu Leu Gly Gly Asp Pro Gly Asp
    130                 135                 140

Ala Ile Ala Val Ile Gly Asp Gly Ala Met Ser Ala Gly Met Ala Tyr
145                 150                 155                 160

Glu Ala Leu Asn Asn Ala Gly His Glu Gly Lys Arg Leu Phe Val Val
                165                 170                 175

Leu Asn Asp Asn Glu Met Ser Ile Ala Pro Pro Val Gly Ala Met Ser
            180                 185                 190

Ser Tyr Leu Thr Arg Leu Tyr Ala Gly Gly Pro Phe Gln Glu Leu Lys
        195                 200                 205
```

```
Ala Val Ala Lys Gly Ala Val Gly Met Leu Pro Asp Ala Leu Gln Glu
    210             215                 220
Asp Ala Arg Arg Ala Lys Glu Met Leu Lys Gly Met Ala Val Gly Gly
225                 230                 235                 240
Thr Leu Phe Glu Glu Leu Gly Phe Ser Tyr Ile Gly Pro Val Asp Gly
                245                 250                 255
His Asp Met Glu Gln Leu Leu Pro Leu Leu Arg Thr Val Arg Ala Arg
            260                 265                 270
Ala Asp Gly Pro Val Leu Ile His Val Val Thr Lys Lys Gly Lys Gly
        275                 280                 285
Tyr Ala Pro Ala Glu Ala Ala Asp Lys Gly His Ala Thr Ala Lys
    290                 295                 300
Phe Asp Val Ile Thr Gly Val Gln Ala Lys Ala Lys Ser Asn Ala Pro
305                 310                 315                 320
Ser Tyr Thr Ala Val Phe Ala Gln Ala Leu Ile Asp Gln Ala Gly Arg
                325                 330                 335
Asp Asp Arg Ile Leu Gly Val Thr Ala Ala Met Pro Asp Gly Thr Gly
            340                 345                 350
Leu Lys Gln Phe Ala Gln Arg Phe Pro Arg Arg Cys Phe Asp Val Gly
        355                 360                 365
Ile Ala Glu Gln His Ala Val Thr Phe Ala Ala Gly Leu Ala Ala Gly
    370                 375                 380
Gly Met Lys Pro Phe Val Ala Ile Tyr Ser Thr Phe Leu Gln Arg Gly
385                 390                 395                 400
Tyr Asp Gln Ile Val His Asp Val Ala Val Gln Asn Leu Pro Val Arg
                405                 410                 415
Phe Ala Val Asp Arg Ala Gly Leu Val Gly Gln Asp Gly Pro Thr His
            420                 425                 430
Ser Gly Ala Tyr Asp Thr Ala Phe Leu Ala Asn Leu Pro Gly Phe Val
        435                 440                 445
Val Met Ala Ala Ala Asp Glu Ala Glu Leu Ala His Met Val Ala Thr
    450                 455                 460
Ala Ala Ala His Asp Ser Gly Pro Ile Ala Phe Arg Phe Pro Arg Gly
465                 470                 475                 480
Glu Gly Thr Gly Val Glu Met Pro Glu Arg Gly Gln Val Leu Pro Ile
                485                 490                 495
Gly Lys Gly Arg Met Ile Ala Glu Gly Lys Gly Val Ala Ile Leu Ser
            500                 505                 510
Phe Gly Thr Arg Leu Ser Glu Val Met Thr Ala Arg Glu Ala Leu Met
        515                 520                 525
Ala Arg Gly Ile Thr Pro Thr Val Ala Asp Ala Arg Phe Ala Lys Pro
    530                 535                 540
Leu Asp Arg Asp Leu Ile Leu Ala Leu Ala Arg Asp His Glu Ala Leu
545                 550                 555                 560
Ile Thr Ile Glu Glu Gly Ala Val Gly Gly Phe Gly Ser His Val Ala
                565                 570                 575
His Leu Leu Ala Glu Glu Gly Ala Phe Asp Lys Gly Leu Arg Phe Arg
            580                 585                 590
Ser Met Val Leu Pro Asp Ala Phe Val Asp His Asp Ala Pro Arg Ala
        595                 600                 605
Met Tyr Asp Ser Ser Cys Leu Asn Ala Gln His Ile Glu Asp Lys Val
    610                 615                 620
```

```
Leu Ser Val Met Gly Val Gln Ser Leu Ala Ala Arg Arg Thr Asp Arg
625                 630                 635                 640

Ala

<210> SEQ ID NO 7
<211> LENGTH: 1002
<212> TYPE: DNA
<213> ORGANISM: Paracoccus carotinifaciens
<220> FEATURE:
<221> NAME/KEY: CDS
<222> LOCATION: (1)..(999)

<400> SEQUENCE: 7 atg act gtg cag gac aac gtc cgc aaa ccg atg gat cgg ctg agc gag      48
Met Thr Val Gln Asp Asn Val Arg Lys Pro Met Asp Arg Leu Ser Glu
1               5                   10                  15 gcc ctg acc gcc gag atg gag gcg gtc aac gcg ctg atc cgc gac cgc      96
Ala Leu Thr Ala Glu Met Glu Ala Val Asn Ala Leu Ile Arg Asp Arg
                20                  25                  30 atg gcc agc cgc cat gcc ccc cgc atc ccc gag gtg acg gcg cat ctg     144
Met Ala Ser Arg His Ala Pro Arg Ile Pro Glu Val Thr Ala His Leu
            35                  40                  45 atc gag gcc ggc ggc aag cgc ctg cgc ccg atg ctg acg ctg gcc gcg     192
Ile Glu Ala Gly Gly Lys Arg Leu Arg Pro Met Leu Thr Leu Ala Ala
        50                  55                  60 gcc aag ctg ctg ggc tat ccc ggc ccg tgg cat gtc cac ctg gcc gcc     240
Ala Lys Leu Leu Gly Tyr Pro Gly Pro Trp His Val His Leu Ala Ala
65                  70                  75                  80 acg gtc gaa ttc atc cat acc gcc acg ctg ctg cat gac gac gtg gtc     288
Thr Val Glu Phe Ile His Thr Ala Thr Leu Leu His Asp Asp Val Val
                85                  90                  95 gac gaa agc gcg cag cgg cgc ggg cgc ccg acg gcg aac ctg ctg tgg     336
Asp Glu Ser Ala Gln Arg Arg Gly Arg Pro Thr Ala Asn Leu Leu Trp
            100                 105                 110 gac aac aag tcc agc gtg ctg gtc gga gat tac ctg ttc gcg cgc agc     384
Asp Asn Lys Ser Ser Val Leu Val Gly Asp Tyr Leu Phe Ala Arg Ser
        115                 120                 125 ttt cag ctg atg gtc gaa ccc ggc aac ctg cga acg ctg gag atc ctg     432
Phe Gln Leu Met Val Glu Pro Gly Asn Leu Arg Thr Leu Glu Ile Leu
    130                 135                 140 gcc aat gcc agc gcc acc atc gcc gag ggc gag gtg ctg cag ctg acc     480
Ala Asn Ala Ser Ala Thr Ile Ala Glu Gly Glu Val Leu Gln Leu Thr
145                 150                 155                 160 gcg gcg cag gac ctg gcg acc gac gaa tcc gtc tat ctg cag gtg gtg     528
Ala Ala Gln Asp Leu Ala Thr Asp Glu Ser Val Tyr Leu Gln Val Val
                165                 170                 175 cgc ggc aag acg gcg gcg ctg ttt tcc gcc gcg acc gag gtg ggc ggc     576
Arg Gly Lys Thr Ala Ala Leu Phe Ser Ala Ala Thr Glu Val Gly Gly
            180                 185                 190 gtc atc gcc ggt gcg ccc gac gat cag gtg cag gcg ctg ttc gat tac     624
Val Ile Ala Gly Ala Pro Asp Asp Gln Val Gln Ala Leu Phe Asp Tyr
        195                 200                 205 ggc gac gcc ctg ggc atc agc ttc cag att gtc gac gac ctg ctg gat     672
Gly Asp Ala Leu Gly Ile Ser Phe Gln Ile Val Asp Asp Leu Leu Asp
    210                 215                 220 tac ggc ggc gcg acc gag acg atc ggc aag aac gtg ggc gac gat ttc     720
Tyr Gly Gly Ala Thr Glu Thr Ile Gly Lys Asn Val Gly Asp Asp Phe
225                 230                 235                 240 cgc gaa cgc aag ctg acc ctg ccg gtc atc aag gcc atc gcc aag gcc     768
Arg Glu Arg Lys Leu Thr Leu Pro Val Ile Lys Ala Ile Ala Lys Ala
                245                 250                 255
```

```
gac gcc gag gaa cgc gcc ttc tgg acc cgc acc atc gag gcg ggc gac      816
Asp Ala Glu Glu Arg Ala Phe Trp Thr Arg Thr Ile Glu Ala Gly Asp
        260                 265                 270 cag cgc gac ggc gac ctg gag cac gcg ctg tcg ctg ctg gcc cgt cac      864
Gln Arg Asp Gly Asp Leu Glu His Ala Leu Ser Leu Leu Ala Arg His
    275                 280                 285 ggt gcg atg gag gcc gcg cgc gcc gat gcg ctg gcc cat gcc gca cgg      912
Gly Ala Met Glu Ala Ala Arg Ala Asp Ala Leu Ala His Ala Ala Arg
290                 295                 300 gtc cgc gcg gcg ctg cag gtg ctg ccc gcg cat ccg att cgc gac atg      960
Val Arg Ala Ala Leu Gln Val Leu Pro Ala His Pro Ile Arg Asp Met
305                 310                 315                 320 ctg gcc gac ctc gcg gat ttc gtc gtc agc cgc gtg gcc tga             1002
Leu Ala Asp Leu Ala Asp Phe Val Val Ser Arg Val Ala
                325                 330

<210> SEQ ID NO 8
<211> LENGTH: 333
<212> TYPE: PRT
<213> ORGANISM: Paracoccus carotinifaciens

<400> SEQUENCE: 8

Met Thr Val Gln Asp Asn Val Arg Lys Pro Met Asp Arg Leu Ser Glu
1               5                   10                  15

Ala Leu Thr Ala Glu Met Glu Ala Val Asn Ala Leu Ile Arg Asp Arg
            20                  25                  30

Met Ala Ser Arg His Ala Pro Arg Ile Pro Glu Val Thr Ala His Leu
        35                  40                  45

Ile Glu Ala Gly Gly Lys Arg Leu Arg Pro Met Leu Thr Leu Ala Ala
    50                  55                  60

Ala Lys Leu Leu Gly Tyr Pro Gly Pro Trp His Val His Leu Ala Ala
65                  70                  75                  80

Thr Val Glu Phe Ile His Thr Ala Thr Leu Leu His Asp Asp Val Val
                85                  90                  95

Asp Glu Ser Ala Gln Arg Arg Gly Arg Pro Thr Ala Asn Leu Leu Trp
            100                 105                 110

Asp Asn Lys Ser Ser Val Leu Val Gly Asp Tyr Leu Phe Ala Arg Ser
        115                 120                 125

Phe Gln Leu Met Val Glu Pro Gly Asn Leu Arg Thr Leu Glu Ile Leu
    130                 135                 140

Ala Asn Ala Ser Ala Thr Ile Ala Glu Gly Glu Val Leu Gln Leu Thr
145                 150                 155                 160

Ala Ala Gln Asp Leu Ala Thr Asp Glu Ser Val Tyr Leu Gln Val Val
                165                 170                 175

Arg Gly Lys Thr Ala Ala Leu Phe Ser Ala Ala Thr Glu Val Gly Gly
            180                 185                 190

Val Ile Ala Gly Ala Pro Asp Asp Gln Val Gln Ala Leu Phe Asp Tyr
        195                 200                 205

Gly Asp Ala Leu Gly Ile Ser Phe Gln Ile Val Asp Asp Leu Leu Asp
    210                 215                 220

Tyr Gly Gly Ala Thr Glu Thr Ile Gly Lys Asn Val Gly Asp Asp Phe
225                 230                 235                 240

Arg Glu Arg Lys Leu Thr Leu Pro Val Ile Lys Ala Ile Ala Lys Ala
                245                 250                 255

Asp Ala Glu Glu Arg Ala Phe Trp Thr Arg Thr Ile Glu Ala Gly Asp
            260                 265                 270
```

```
Gln Arg Asp Gly Asp Leu Glu His Ala Leu Ser Leu Leu Ala Arg His
    275                 280                 285

Gly Ala Met Glu Ala Ala Arg Ala Asp Ala Leu Ala His Ala Ala Arg
    290                 295                 300

Val Arg Ala Ala Leu Gln Val Leu Pro Ala His Pro Ile Arg Asp Met
305                 310                 315                 320

Leu Ala Asp Leu Ala Asp Phe Val Val Ser Arg Val Ala
                325                 330

<210> SEQ ID NO 9
<211> LENGTH: 1452
<212> TYPE: DNA
<213> ORGANISM: Paracoccus carotinifaciens
<220> FEATURE:
<221> NAME/KEY: misc_feature
<222> LOCATION: (1350)..(1350)
<223> OTHER INFORMATION: n is a, c, g, or t

<400> SEQUENCE: 9
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg gcccagactc     300
ctacgggagg cagcagtggg gaatcttaga caatggggc aaccctgatc tagccatgcc     360
gcgtgagtga tgaaggcctt agggttgtaa agctctttca gctgggaaga taatgacggt     420
accagcagaa gaagccccgg ctaactccgt gccagcagcc gcggtaatac ggaggggct     480 agcgttgttc ggaattactg ggcgtaaagc gcacgtaggc ggactggaaa gtcagaggtg     540
aaatcccagg gctcaacctt ggaactgcct ttgaaactat cagtctggag ttcgagagag     600
gtgagtggaa ttccgagtgt agaggtgaaa ttcgtagata ttcggaggaa caccagtggc     660
gaaggcggct cactggctcg atactgacgc tgaggtgcga aagcgtgggg agcaaacagg     720
attagatacc ctggtagtcc acgccgtaaa cgatgaatgc cagacgtcgg caagcatgct     780
tgtcggtgtc acacctaacg gattaagcat tccgcctggg gagtacggtc gcaagattaa     840
aactcaaagg aattgacggg ggcccgcaca agcggtggag catgtggttt aattcgaagc     900
aacgcgcaga accttaccaa cccttgacat ggcaggaccg ctggagagat tcagctttct     960
cgtaagagac ctgcacacag gtgctgcatg gctgtcgtca gctcgtgtcg tgagatgttc    1020
ggttaagtcc ggcaacgagc gcaacccacg tccctagttg ccagcaattc agttgggaac    1080
tctatggaaa ctgccgatga taagtcggag gaaggtgtgg atgacgtcaa gtcctcatgg    1140
gccttacggg ttgggctaca cacgtgctac aatggtggtg acagtgggtt aatcccaaa     1200 agccatctca gttcggattg tcctctgcaa ctcgagggca tgaagttgga atcgctagta    1260
atcgcggaac agcatgccgc ggtgaatacg ttcccgggcc ttgtacacac cgcccgtcac    1320
accatgggag ttggttctac ccgacgacgn tgcgctaacc ttcggggggc aggcggccac    1380
ggtaggatca gcgactgggg tgaagtcgta acaaggtagc cgtagggaa cctgcggctg    1440 gatcacctcc tt                                                       1452
```

CAROTENOID PRODUCTION METHOD

CROSS REFERENCE

This application is the U.S. National Phase under 35 U.S.C. § 371 of International Application No. PCT/JP2017/014162 filed on Mar. 29, 2017, which claims the benefit of Japanese Application No. 2016-071303 filed on Mar. 31, 2016, the entire contents of each are hereby incorporated by reference herein.

FIELD OF THE INVENTION

The present invention relates to a method for producing a carotenoid using a mutant strain of a carotenoidogenic bacterium.

BACKGROUND ART

Carotenoids are useful natural pigments that can be used as feed additives, food additives, pharmaceutical products and the like. Examples of carotenoids include astaxanthin, canthaxanthin, zeaxanthin, β-cryptoxanthin, lycopene, β-carotene, adonirubin, adonixanthin, echinenone, asteroidenone and 3-hydroxyechinenone. Among them, astaxanthin is useful as a feed additive such as a body color improving agent for farmed fish such as salmon, trout and red sea bream, and an egg-yolk color improving agent for poultry and the like. Natural astaxanthins are also highly valuable in industries as safe food additives and health food ingredients. Similar to astaxanthin, adonixanthin and adonirubin are expected of their use as feed additives, food additives, pharmaceutical products and the like.

In addition, β-carotene is used as a feed additive, a food additive, a pharmaceutical product and a like, canthaxanthin is used as a feed additive, a food additive, a cosmetic product and the like, and zeaxanthin is used as a food additive, a feed additive and the like. Furthermore, lycopene, echinenone, β-cryptoxanthin, 3-hydroxyechinenone and asteroidenone are also expected of their use as feed additives, food ingredients and the like. As a method for producing such carotenoids, a chemical synthesis method, an extraction method from a natural product, a production method by culturing microorganisms, and the like are known.

As the chemical synthesis method for astaxanthin, a method by β-carotene conversion (Pure Appl. Chem., 57, 741, 1985 (Non-patent document 1)) and a method by synthesizing from a C15 phosphonium salt (Helv. Chim. Acta, 64, 2436, 1981 (Non-patent document 2)) are known. As the extraction method from a natural product, astaxanthin may be extracted and collected from fish like salmon or red sea bream, or a crustacean like shrimp, crab or krill in which astaxanthin is present.

Examples of the method for producing a carotenoid using microorganisms include a culture method using a green alga *Haematococcus pluvialis* (Japanese Patent Application Publication No. 2007-97584 (Patent document 1)), a fermentation method using red yeast *Phaffia rhodozyma* (Japanese Patent Application Publication No. H11(1999)-69969 (Patent document 2)), a fermentation method using a bacterium belonging to the genus *Paracoccus* (hereinafter, also referred to as a "bacterium of the genus *Paracoccus*"), a fermentation method using a bacterium belonging to the genus *Brevundimonas* (Japanese Patent Application Publication No. 2006-340676 (Patent document 3)), and a fermentation method using a bacterium belonging to the genus *Erythrobacter* (Japanese Patent Application Publication No. 2008-259449 (Patent document 4)). Examples of the bacteria of the genus *Paracoccus* that produce carotenoids include strains E-396 and A-581-1 (Japanese Patent Application Publication No. H7 (1995)-79796 (Patent document 5) and International Journal of Systematic Bacteriology (1999), 49, 277-282 (Non-patent document 3)). Examples of other carotenoid-producing bacteria belonging to the genus *Paracoccus* include *Paracoccus marcusii* strain MH1 (Japanese Patent Application Publication No. 2001-512030 (Patent document 6)), *Paracoccus haeundaensis* strain BC74171 (International Journal of Systematic and Evolutionary Microbiology (2004), 54, 1699-1702 (Non-patent document 4)), bacterium *Paracoccus* strain sp. N-81106 (Japanese Patent Application Publication No. 2007-244205 (Patent document 7)), *Paracoccus zeaxanthinifaciens* (International Journal of Systematic and Evolutionary Microbiology (2003), 53, 231-238 (Non-patent document 5)) and *Paracoccus* sp. strain PC-1 (pamphlet of WO2005/118812 (Patent document 8)).

The above-mentioned methods for producing carotenoids, however, have several problems. For example, a carotenoid produced by a chemical synthesis method may be safe but gives unfavorable impression to the consumers. The production cost of carotenoids extracted from natural products are much more expensive than the chemical synthesis method. Among the productions using microorganisms, production by culturing a gree alga or a yeast is low in productivity and difficult in extracting carotenoids from the cultured products since these microorganisms have strong cell walls.

Meanwhile, several culture methods and production methods have been reported for carotenoid productions using bacteria belonging to the genus *Paracoccus* because they are advantageous in terms of fast bacterial growth rate, high carotenoid productivity, and easy carotenoid extraction from the cultured product.

For example, Japanese Patent Application Publication No. 2007-143492 (Patent document 9) discloses a method of adding an iron salt during culturing, pamphlet of WO2010/044469 (Patent document 10) discloses a method of adding amino acids to the medium, Japanese Patent Application Publication No. 2011-188795 (Patent document 11) discloses a method of adding biotin to the medium, and Japanese Patent Application Publication No. 2012-139164 (Patent document 12) discloses a method of adding a calcium compound to the medium to 3.6 mM or more.

However, details as to which gene of the carotenoid-producing bacteria contributes to the increase in the production efficiency have been unclear.

PRIOR ART DOCUMENTS

Patent Documents

Patent document 1: Japanese Patent Application Publication No. 2007-97584
Patent document 2: Japanese Patent Application Publication No. H11(1999)-69969
Patent document 3: Japanese Patent Application Publication No. 2006-340676
Patent document 4: Japanese Patent Application Publication No. 2008-259449
Patent document 5: Japanese Patent Application Publication No. H7(1995)-79796
Patent document 6: Japanese Patent Application Publication No. 2001-512030

Patent document 7: Japanese Patent Application Publication No. 2007-244205
Patent document 8: Pamphlet of WO2005/118812
Patent document 9: Japanese Patent Application Publication No. 2007-143492
Patent document 10: Pamphlet of WO2010/044469
Patent document 11: Japanese Patent Application Publication No. 2011-188795
Patent document 12: Japanese Patent Application Publication No. 2012-139164

Non-Patent Documents

Non-patent document 1: Pure Appl. Chem., 57, 741, 1985
Non-patent document 2: Helv. Chim. Acta, 64, 2436, 1981
Non-patent document 3: International Journal of Systematic Bacteriology (1999), 49, 277-282
Non-patent document 4: International Journal of Systematic and Evolutionary Microbiology (2004), 54, 1699-1702
Non-patent document 5: International Journal of Systematic and Evolutionary Microbiology (2003), 53, 231-238

SUMMARY OF INVENTION

Problem to be Solved by Invention

The present invention has an objective of providing a mutant carotenoidogenic bacterium, and a method for producing a carotenoid using said bacterium.

The present inventors have gone through extensive investigation to solve the above-described problems, and as a result of which succeeded in acquiring a bacterium having high astaxanthin productivity among the bacteria subjected to a mutation treatment, thereby accomplishing the present invention.

Means for Solving Problem (1) A mutant carotenoidogenic bacterium, comprising any of genes (a)-(c) below:
  (a) a gene encoding a protein comprising a mutant amino acid sequence in which at least the 225th amino acid residue in the amino acid sequence of 1-deoxy-D-xylulose 5-phosphate synthase of a carotenoidogenic bacterium has been substituted with other amino acid residue;
  (b) a gene encoding a protein comprising a mutant amino acid sequence in which at least the 305th amino acid residue in the amino acid sequence of decaprenyl diphosphate synthase of a carotenoidogenic bacterium has been substituted with other amino acid residue; and
  (c) both of the genes (a) and (b) above.
(2) The bacterium according to (1), wherein the amino acid sequence of 1-deoxy-D-xylulose 5-phosphate synthase is the sequence represented by SEQ ID NO:2.
(3) The bacterium according to either one of (1) and (2), wherein the 225th amino acid residue has been substituted from glycine to aspartic acid.
(4) The bacterium according to any one of (1)-(3), wherein the amino acid sequence of decaprenyl diphosphate synthase is the sequence represented by SEQ ID NO:4.
(5) The bacterium according to any one of (1)-(4), wherein the 305th amino acid residue has been substituted from alanine to valine.
(6) The bacterium according to any one of (1)-(5), which has acquired carotenogenic capacity that is higher than the carotenogenic capacity of a carotenoidogenic bacterium without the gene encoding the protein comprising the mutant amino acid sequence.
(7) The bacterium according to (6), which has acquired carotenogenic capacity that is at least 5 times or more the carotenoid production amount of a carotenoidogenic bacterium without the gene encoding the protein comprising the mutant amino acid sequence.
(8) The bacterium according to any one of (1)-(7), wherein the carotenoidogenic bacterium belongs to the genus *Paracoccus*.
(9) The bacterium according to (8), wherein the bacterium belonging to the genus *Paracoccus* is strain E-396.
(10) The bacterium according to any one of (1)-(9), wherein the carotenoid is astaxanthin.
(11) A method for producing a carotenoid, comprising culturing the bacterium according to any one of (1)-(10), and collecting the carotenoid from the resulting cultured product.
(12) The method according to (11), wherein the carotenoid production amount is at least 5 times or more the carotenoid production amount of a carotenoidogenic bacterium without the gene encoding the protein comprising the mutant amino acid sequence.
(13) The method according to either one of (11) and (12), wherein the carotenoid is astaxanthin.
(14) A method for screening for a carotenoidogenic bacterium, comprising subjecting a carotenoidogenic bacterium to a mutation treatment, and selecting a bacterium having any of characteristics (a)-(c) below from the bacteria subjected to the mutation treatment:
  (a) a characteristic where the activity of 1-deoxy-D-xylulose 5-phosphate synthase is increased compared to said activity in the bacterium before the mutation treatment;
  (b) a characteristic where the activity of decaprenyl diphosphate synthase is decreased compared to said activity in the bacterium before the mutation treatment; and
  (c) both of the characteristics (a) and (b) above.
(15) A method for producing a carotenoid, comprising culturing the bacterium selected by the method according to (14), and collecting a carotenoid from the resulting cultured product.
(16) A gene encoding a protein comprising a mutant amino acid sequence in which at least the 225th amino acid residue in the amino acid sequence of 1-deoxy-D-xylulose 5-phosphate synthase has been substituted with other amino acid residue.
(17) A gene comprising either of DNA (a) or (b) below:
  (a) DNA comprising the nucleotide sequence represented by SEQ ID NO:5; or
  (b) DNA that hybridizes with DNA having a nucleotide sequence complementary to said DNA (a) under stringent conditions, and that encodes a protein having 1-deoxy-D-xylulose 5-phosphate synthase activity.
(18) A gene encoding a protein comprising a mutant amino acid sequence in which at least the 305th amino acid residue in the amino acid sequence of decaprenyl diphosphate synthase has been substituted with other amino acid residue.
(19) A gene comprising either of DNA (a) or (b) below:
  (a) DNA comprising the nucleotide sequence represented by SEQ ID NO:7; or
  (b) DNA that hybridizes with DNA having a nucleotide sequence complementary to said DNA (a) under stringent conditions, and that encodes a protein with decreased decaprenyl diphosphate synthase activity.

(20) A recombinant vector comprising any of genes (a)-(c) below:
(a) the gene according to (16) or (17);
(b) the gene according to (18) or (19); and
(c) the genes (a) and (b) above.
(21) A transformant comprising the recombinant vector according to (20).
(22) A method for producing a carotenoid, comprising culturing the transformant according to (21), and collecting a carotenoid from the resulting cultured product.

Effect of the Invention

The present invention provides a high carotenoid producing bacterium. Carotenoids can efficiently be produced by using the bacterium of the present invention.

BRIEF DESCRIPTION OF THE DRAWINGS

FIG. 4 Images showing the template structure and a model structure of a complex of Enzyme A with TPP coenzyme. The structure of the complex of *D. radiodurans*-derived 1-deoxy-D-xylulose 5-phosphate synthase (DXS) with TPP (2O1X) as the template (left) and the model structure of constructed Enzyme A (right). In the formed homodimer, each subunit binds TPP and Mg. TPP and Mg are shown in space-filling representation.

FIG. 5 Images showing the model structure of the complex of Enzyme A with a TPP intermediate and a substrate. A complex model in which the constructed Enzyme A is bonded with a hydroxyethyl-TPP intermediate having pyruvic acid attached to TPP coenzyme and glyceraldehyde 3-phosphate (GAP) is shown.

FIG. 7 Images showing the amino acid residues of Enzyme A that were predicted responsible for the interaction with TPP. The residues predicted to be responsible for the interaction with TPP are represented by sticks.

FIG. 8 Images showing the amino acid residues that were predicted responsible for the interaction between Enzyme A and the hydroxyethyl group of the hydroxyethyl-TPP intermediate. The residues predicted to be responsible for the interaction with the hydroxyethyl group are represented by sticks.

FIG. 9 Images showing the amino acid residues that were predicted responsible for the interaction between Enzyme A and glyceraldehyde 3-phosphate (GAP).

FIG. 12 A depiction showing the alignment between Enzyme A and other types of DXS. EnzymeA: Enzyme A, DXS_ECOLI: DXS (*E. coli*), DXS_VITVI: DXS (*Vitis vinifera*), DXS_DEIRA: (*Deinococcus radiodurans*). The disordered region in the template structure (DXS_DEIRA) is represented by a blue bar. The active sites are shown in green boxes while mutations that showed activity enhancement in DXS_ECOLI and DXS_VITVI are marked with red triangles.

FIG. 13 Images showing the location of the disordered region in Enzyme A. Asn180 and Met182 in the loop on the N-terminal side of the disordered region (dotted blue line) bind Mg while Ile184 binds TPP.

FIG. 17 A depiction showing the alignment between Enzyme C and the template structure (3MZV). The deduced active sites are depicted in green.

FIG. 18 Images showing the template structure and a model structure of a complex of Enzyme C with IPP and FPP. *R. capsulatus*-derived decaprenyl diphosphate synthase (3MZV) as the template (left) and the model structure of constructed Enzyme C (right). FPP and IPP are shown in space-filling representation.

FIG. 19 Images showing the template structure, and the model structure of the complex of Enzyme C with IPP and FPP. FPP and IPP bind each other in the head-to-tail direction while the condensation reaction occurs between an isopentenyl group of IPP and a phosphate group of FPP (left image, arrow). In the long-chain prenyl diphosphate synthase, the reaction product further binds IPP and extends deep into the substrate binding site (right image, arrow).

FIG. 20 Images showing comparison between the template structure and the model structure of Enzyme C. The complex models of template *R. capsulatus*-derived decaprenyl diphosphate synthase (left) and Enzyme C (right) with the substrate. The structures with matching amino acid residues are depicted in green. The substrate binding region and its surrounding structure match entirely.

FIG. 21 A depiction showing the alignment between Enzyme C and decaprenyl diphosphate synthase (*Paracoccus zeaxanthinifaciens*).

FIG. 22 Images showing a complex model of Enzyme C with FPP and IPP. The ribbon representation (left) and the surface profile (right). Chain A (light red) and chain B (light blue) are shown. FPP and IPP are shown in space-filling representation.

FIG. 26 Images showing conformational models of wild-type and mutant A305V Enzyme C. Ala305 (green) and Val305 (magenta) are shown in space-filling representation.

FIG. 29 Images showing comparison of the structures between the wild type and mutant A305V. Mutation A305V causes change in the structure of the amino acid residues around Ala305 (green) and Val305 (magenta) (left). This structural change also affects the adjacent α-helix (right).

FIG. 32 Images showing the effect of A305V in Enzyme C.

MODE FOR CARRYING OUT THE INVENTION

Figure 1:
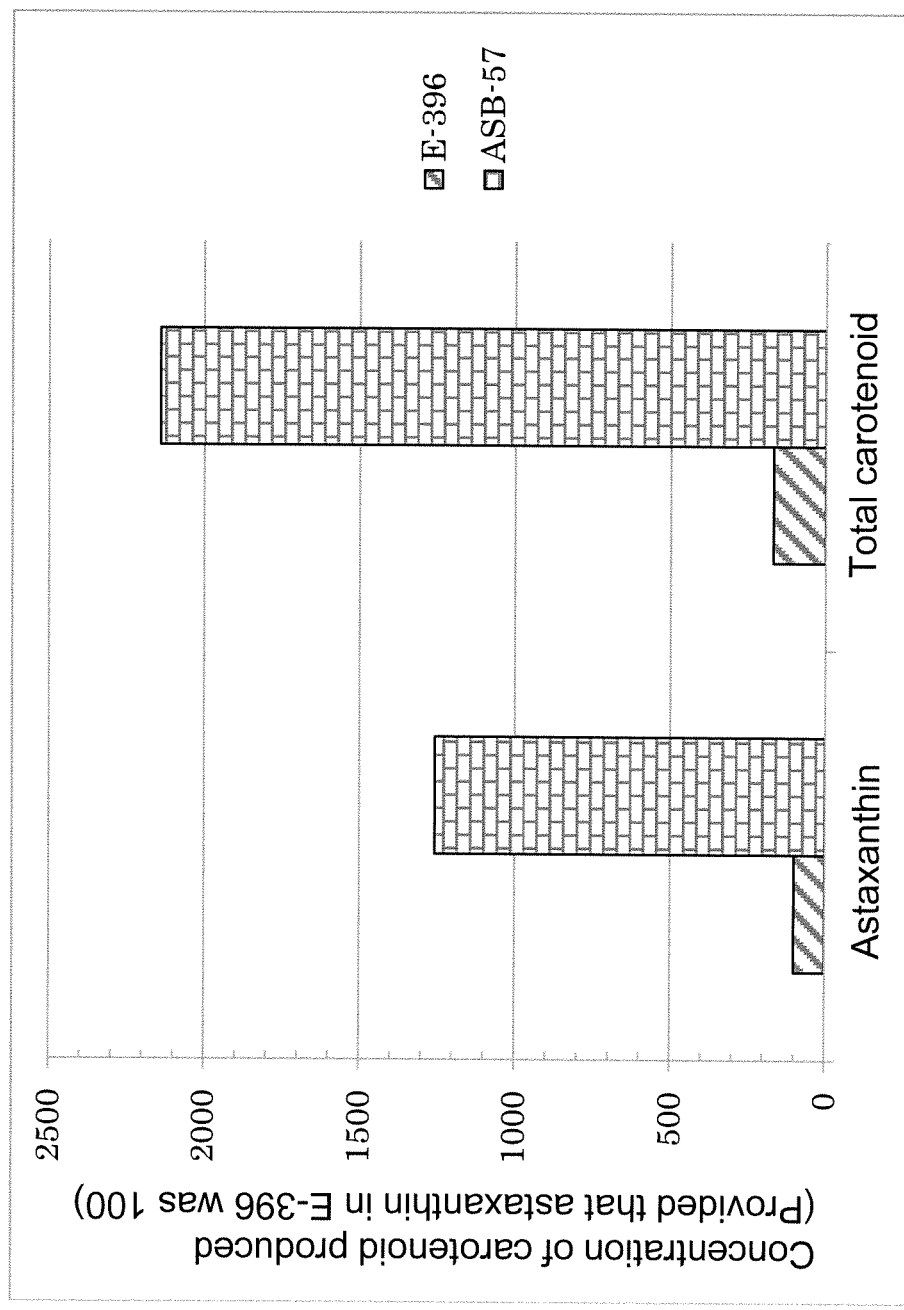
FIG. 1 A diagram showing specific productivities of total carotenoid and astaxanthin in strain E-396 and strain ASB-57.

Hereinafter, the present invention will be described in detail.

1. General

The present invention relates to a high carotenoid producing bacterium, which is a bacterium comprising either or both of genes (a) and (b) below.

(a) a gene encoding a protein comprising a mutant amino acid sequence in which at least the 225th amino acid residue in the amino acid sequence of 1-deoxy-D-xylulose 5-phosphate synthase of a carotenoidogenic bacterium has been substituted with other amino acid residue; and (b) a gene encoding a protein comprising a mutant amino acid sequence in which at least the 305th amino acid residue in the amino acid sequence of decaprenyl diphosphate synthase of a carotenoidogenic bacterium has been substituted with other amino acid residue.

In order to develop a bacterium having high carotenogenic capacity, the present inventors have examined the carotenogenic capacity in strain E-396 and strains thereof that had been subjected to a mutation treatment, and analyzed the mutation of a gene encoding an enzyme involved in the carotenoid synthesis pathway in these strains.

As a result, a strain (referred to as "strain ASB-57") that had higher carotenogenic capacity than the parent strain E-396 was acquired. Genome analysis for strain ASB-57 confirmed mutations in the amino acid sequence of 1-deoxy-D-xylulose 5-phosphate synthase (DXS) and the amino acid sequence of decaprenyl diphosphate synthase (DPS). Thus, a functional analysis was conducted by prediction based on a conformational analysis of the amino acids, by which the mutation of at least the 225th amino acid residue of DXS and/or the 305th amino acid residue of DPS was considered to contribute to the high carotenoid production.

The present invention was accomplished based on the above-described findings.

2. Mutant Carotenoidogenic Bacterium

A carotenoidogenic bacterium of the present invention is a mutant bacterium that can produce a carotenoid with high efficiency, which can be obtained by subjecting a parent strain to a mutation treatment and using the mutations at the 225th amino acid residue of DXS and/or the 305th amino acid residue of DPS as indicators. A carotenoidogenic bacterium of the present invention is herein referred to as a "mutant carotenoidogenic bacterium".

(1) Parent Strain

According to the present invention, a bacterium used as the parent strain for obtaining a mutant carotenoidogenic bacterium is not limited at all as long as it produces a carotenoid, and may be, for example, a bacterium belonging to the genus *Paracoccus*, the genus *Brevundimonas* or the genus *Erythrobacter*.

A bacterium belonging to the genus *Paracoccus*, a bacterium belonging to the genus *Brevundimonas* or a bacterium belonging to the genus *Erythrobacter* can preferably be used, and a bacterium belonging to the genus *Paracoccus* can more preferably be used. Since all of the genus *Paracoccus*, the genus *Erythrobacter* and the genus *Brevundimonas* belong to the class Alphaproteobacteria in the phylum Proteobacteria, and are common in bacterial taxonomy, bacteria belonging to these genera can be used for the present invention.

Among the bacteria belonging to the genus *Paracoccus*, *Paracoccus carotinifaciens*, *Paracoccus marcusii*, *Paracoccus haeundaensis* and *Paracoccus zeaxanthinifaciens* can preferably be used, and *Paracoccus carotinifaciens* can particularly preferably be used. Specific examples of the strains of the bacteria belonging to the genus *Paracoccus* include strain E-396 of *Paracoccus carotinifaciens* (FERM BP-4283) and strain A-581-1 of the bacteria of the genus *Paracoccus* (FERM BP-4671), whose mutants can also preferably be used for the present invention.

Examples of the carotenoidogenic bacteria belonging to the genus *Erythrobacter* include *Erythrobacter* JPCC M sp. (Japanese Patent Application Publication No. 2008-259452) and *Erythrobacter* JPCC O sp. (Japanese Patent Application Publication No. 2008-259449).

Examples of carotenoidogenic bacteria belonging to the genus *Brevundimonas* include *Brevundimonas* sp. strain SD212 (Japanese Patent Application Publication No. 2009-27995), *Brevundimonas* sp. strains FERM P-20515 and 20516 (Japanese Patent Application Publication No. 2006-340676), and *Brevundimonas vesicularis* (Gene, Vol. 379, p. 101-108, 1 Sep. 2006).

In addition, a bacterium whose nucleotide sequence of DNA corresponding to 16S ribosomal RNA is highly homologous with the nucleotide sequence of strain E-396 represented by SEQ ID NO:9 is preferably used as the carotenoidogenic bacterium. Herein, the homology of the nucleotide sequence is preferably 95% or more, more preferably 96% or more, still more preferably 97% or more, particularly preferably 98% or more, and most preferably 99% or more.

The nucleotide sequence of DNA corresponding to 16S ribosomal RNA refers to a nucleotide sequence obtained by substituting U (uracil) of the nucleotide sequence of 16S ribosomal RNA with T (thymine).

Classification of microorganisms based on the homology of this nucleotide sequence of 16S ribosomal RNA has been the recent mainstream. Since conventional classification of microorganisms is based on conventional microbiological characteristics such as motility, auxotrophy, sugar assimilation and the like, a microorganism may be classified incorrectly when morphological change or the like is caused due to naturally occurring mutation. On the other hand, the nucleotide sequence of 16S ribosomal RNA is genetically very stable and thus reliability of the classification technique based on that homology is considerably enhanced compared to that of the conventional classification technique.

Homologies of the nucleotide sequence of 16S ribosomal RNA of *Paracoccus carotinifaciens* strain E-396 with the nucleotide sequences of 16S ribosomal RNA of other carotenoidogenic bacteria, i.e., *Paracoccus marcusii* strain DSM 11574, strain N-81106 of the bacterium of the genus *Paracoccus*, *Paracoccus haeundaensis* strain BC 74171, strain A-581-1 of the bacterium of the genus *Paracoccus*, *Paracoccus zeaxanthinifaciens* strain ATCC 21588, and *Paracoccus* sp. strain PC-1 are 99.7%, 99.7%, 99.6%, 99.4%, 95.7% and 95.4%, respectively, which represent that these strains are closely related taxonomically. Hence, these strains are found to form a group of bacteria that produce carotenoids. Therefore, these strains can preferably be used for the present invention, and are capable of efficiently producing carotenoids.

According to the present invention, known mutants having improved carotenoid productivity can also be used. Examples of such known mutants include a strain having high astaxanthin production capacity (Japanese Patent Application Publication No. 2001-95500), a strain that selectively produce an increased amount of canthaxanthin (Japanese Patent Application Publication No. 2003-304875), a strain that selectively produce increased amounts of zeaxanthin and β-cryptoxanthin (Japanese Patent Application Publication No. 2005-87097), and a strain that selectively produce an increased amount of lycopene (Japanese Patent Application Publication No. 2005-87100).

Strain E-396 as an exemplary carotenoidogenic bacterium used as the parent strain for the present invention has been internationally deposited to the International Patent Organism Depositary (NITE-IPOD), the National Institute of Technology and Evaluation (NITE) as follows.

International depositary authority: International Patent Organism Depositary, National Institute of Technology and Evaluation (NITE)

2-5-8, Kazusakamatari, Kisarazu-shi, Chiba, 292-0818, JAPAN

Identification reference: E-396

Accession number: FERM BP-4283

Date of the original deposit: Apr. 27, 1993

In addition, strain A-581-1 as another exemplary carotenoidogenic bacterium used as the parent strain in the present invention has been internationally deposited to the above-mentioned authority as follows.

Identification reference: A-581-1

Accession number: FLRM BP-4671

Date of the original deposit: May 20, 1994

(2) Mutation Treatment and Screenings

A mutant carotenoidogenic bacterium of the present invention can be obtained by subjecting the above-described parent strain to a mutation treatment and using the mutations at the 225th amino acid residue of DXS and/or the 305th amino acid residue of DPS as indicators.

A method of the mutation treatment is not particularly limited as long as it can induce mutation. For example, a chemical method using a mutation agent such as N-methyl-N'-nitro-N-nitrosoguanidine (NTG) or ethyl methanesulfonate (EMS), a physical method such as ultraviolet irradiation or X-ray irradiation, a biological method using gene recombination or transposon, or the like may be employed. Although the bacterium subjected to the mutation treatment is not particularly limited, it is preferably a carotenoidogenic bacterium.

Moreover, according to the present invention, a protein having the above-described mutation can be prepared by introducing point mutation into a gene (DNA) encoding said protein. For such a mutagenesis method, a mutagenesis kit utilizing a site-directed mutagenesis method such as Kunkel method or Gapped duplex method, for example, QuikChange™ Site-Directed Mutagenesis Kit (from Stratagene), GeneTailor™ Site-Directed Mutagenesis System (from Invitrogen), TaKaRa Site-Directed Mutagenesis System (Mutan-K, Mutan-Super Express Km, etc: from Takara Bio) or the like can be used. In addition, a method such as site-directed mutagenesis described in "Molecular Cloning, A Laboratory Manual (4th edition)" (Cold Spring Harbor Laboratory Press (2012)) or the like can be used.

While a method for screening a mutant is not particularly limited, a known genome analysis tool such as PacBio RS II (from Pacific Biosciences) or MiSeq (from Illumina) can be used for gene analysis to confirm the presence of a mutation of the nucleotide sequence corresponding to the 225th amino acid residue of DXS and/or the 305th amino acid residue of DPS.

Furthermore, along with the above-described genome analysis, the mutant of interest can, for example, be selected by the color tone of the colony on the agar medium, or selected by culturing the mutants in a test tube, a flask, a fermentation tank or the like and using the production amount of the carotenoid as an indicator in an analysis of carotenoid pigment utilizing absorbance, high performance liquid chromatography, thin-layer chromatography or the like.

The mutation and screening steps can be carried out once, or the mutation and screening steps can be repeated twice or more, for example, by obtaining mutants by a mutation treatment and screening and subjecting the resultant to another mutation treatment and screening to acquire a mutant with improved productivity.

The mutant carotenoidogenic bacterium screened as such has a gene encoding an amino acid sequence in which the 225th amino acid residue of DXS is altered to other amino acid and/or the 305th amino acid residue of DPS is altered to other amino acid residue.

Mutation of the 225th amino acid residue of DXS to other amino acid contributes to the increase in the the enzymatic activity of DXS. Thus, synthesis from pyruvic acid to 1-deoxy-D xylulose-5-phosphate is promoted, which leads to the increase in the production of isopentenyl diphosphate (IPP) that serves as a substrate for astaxanthin synthesis.

Mutation of the 305th amino acid residue of DPS to other amino acid residue contributes to the reduction in the enzymatic activity of DPS. This mutation suppresses synthesis from farnesyl diphosphate (FPP) to decaprenyl diphosphate (DPP). Since IPP is used for the synthesis of DPP from FPP, the above-described mutation will reduce the amount of IPP used for the DPP synthesis and said IPP will be utilized as a substrate for the above-described astaxanthin synthesis.

Here, according to the present invention, as long as an amino acid sequence has the 225th amino acid residue of DXS altered to other amino acid and/or the 305th amino acid residue of DPS altered to other amino acid residue, and has a gene coding for a protein comprising an amino acid sequence having such DXS activity and/or a protein comprising an amino acid sequence with reduced (suppressed) DPS activity, one or more amino acid residues in an amino acid sequence of other region of the amino acid sequence of DXS and/or DPS may be altered by substitution, deletion, addition or the like.

Accordingly, a mutant carotenoidogenic bacterium of the present invention may comprise the gene (a) below, the gene (b) below, or both of the genes (a) and (b) below.

(a) A gene encoding a protein comprising a mutant amino acid sequence in which at least the 225th amino acid residue has been substituted with other amino acid residue in the amino acid sequence of DXS of a carotenoidogenic bacterium.

Examples of such mutant DXS genes include the followings.

(i) A gene encoding a protein that comprises a mutant amino acid sequence in which the 225th amino acid residue in the amino acid sequence of DXS (for example, SEQ ID NO:2) has been substituted with other amino acid residue, and that has DXS activity.

An example of such a mutant amino acid sequence includes one represented by SEQ ID NO:6, while an example of the above-mentioned gene includes one represented by SEQ ID NO:5. According to the present invention, it is preferably an amino acid sequence in which glycine as the 225th amino acid residue in the amino acid sequence represented by SEQ ID NO:2 is substituted with aspartic acid.

(ii) A gene encoding a protein that comprises a mutant amino acid sequence in which the 225th amino acid residue in the amino acid sequence of DXS (for example, SEQ ID NO:2) is substituted with other amino acid residue and in which one or more (for example, one to several) amino acid residues other than the 225th amino acid residue have been deleted, substituted or added, and that has DXS activity.

(iii) A gene consisting of DNA comprising the nucleotide sequence represented by SEQ ID NO:5.

(iv) A gene comprising DNA that hybridizes with DNA consisting of a nucleotide sequence complementary to DNA comprising the nucleotide sequence represented by SEQ ID NO:5 under stringent conditions, and that encodes a protein having DXS activity.

Among the DNA encoding the amino acid sequence of DXS (SEQ ID NO:1) of a carotenoidogenic bacterium, the above-described nucleotide sequence represented by SEQ ID NO:5 is one that codes for a protein comprising an amino acid sequence in which the 225th amino acid residue has been substituted with other amino acid residue.

(b) A gene encoding a protein comprising a mutant amino acid sequence in which at least the 305th amino acid residue in the amino acid sequence of DPS of a carotenoidogenic bacterium has been substituted with other amino acid residue.

Examples of such genes include the followings.

(i) A gene encoding a protein that comprises a mutant amino acid sequence in which the 305th amino acid residue in the amino acid sequence of DPS (for example, SEQ ID NO:4) has been substituted with other amino acid residue, and that has reduced DPS activity.

An example of such a mutant amino acid sequence includes one represented by SEQ ID NO:8, while an example of the above-described gene includes one represented by SEQ ID NO:7. According to the present invention, it is preferably an amino acid sequence in which alanine as the 305th amino acid residue in the amino acid sequence represented by SEQ ID NO:4 is substituted with valine.

(ii) A gene encoding a protein that comprises a mutant amino acid sequence in which the 305th amino acid residue in the amino acid sequence of DPS (for example, SEQ ID NO:4) is substituted with other amino acid residue and in which one or more (for example, one to several) amino acid residues other than the 305th amino acid residue have been deleted, substituted or added, and that has reduced DPC activity.

(iii) A gene consisting of DNA comprising the nucleotide sequence represented by SEQ ID NO:7.

(iv) A gene comprising DNA that hybridizes with DNA consisting of a nucleotide sequence complementary to DNA comprising the nucleotide sequence represented by SEQ ID NO:7 under stringent conditions, and that encodes a protein having reduced DPS activity.

Among the DNA encoding the amino acid sequence of DPS (SEQ ID NO:3) of a carotenoidogenic bacterium, the above-described nucleotide sequence represented by SEQ ID NO:7 is one that codes for a protein comprising an amino acid sequence in which the 305th amino acid residue has been substituted with other amino acid residue.

Here, the hybridization can be performed according to a known method (for example, Sambrook J. et al., Molecular Cloning, A Laboratory Manual (4th edition) (Cold Spring Harbor Laboratory Press (2012)). Highly stringent conditions refer to conditions under which so-called specific hybrids, but not non-specific hybrids are formed, which are, for example, a sodium concentration of 10 mM-300 mM, preferably 20 mM-100 mM and a temperature of 25° C.-70° C., preferably 42° C.-55° C.

Examples of such a mutant carotenoidogenic bacterium include strain ASB-57, strain ASK-8 and strain ASH-66.

Strain ASB-57 has a gene encoding a protein comprising an amino acid sequence in which glycine as the 225th amino acid residue of DXS is altered to aspartic acid, and alanine as the 305th amino acid residue of DPS is altered to valine. The amino acid sequence of DXS in strain ASB-57 and the nucleotide sequence of the gene thereof are represented by SEQ ID NOS:6 and 5, respectively. Moreover, the amino acid sequence of DPS in strain ASB-57 and the nucleotide sequence of the gene thereof are represented by SEQ ID NOS:8 and 7, respectively (4) Preparation of Gene Recombinant According to the present invention, the gene encoding the above-described mutant DXS and/or the gene encoding the above-described mutant DPS is introduced into a host for transformation, thereby obtaining a gene recombinant type mutant carotenoidogenic bacterium.

A recombinant vector can be obtained by introducing the mutant DXS gene and/or the mutant DPS gene into a vector, and a transformant can be obtained by introducing said recombinant vector into a host by employing any known method such as Sambrook J. et al., Molecular Cloning, A Laboratory Manual (4th edition) (Cold Spring Harbor Laboratory Press (2012).

When synthesizing the above-described DXS gene and DPS gene by genetic engineering, DNA coding for said enzyme is first designed and synthesized. The design and synthesis of DNA can be conducted, for example, by a PCR method using a vector containing the full-length gene or the like as a template and primers designed to synthesize the DNA region desired. Then, the above-described DNA is linked with a suitable vector to obtain a recombinant vector for protein expression, and this recombinant vector is introduced into a host such that the gene of interest is expressed, thereby obtaining a transformant (Sambrook J. et al., Molecular Cloning, A Laboratory Manual (4th edition) (Cold Spring Harbor Laboratory Press (2012)).

As the vector, a phage or a plasmid that can autonomously grow in a host microorganism is used. Alternatively, an animal virus or an insect virus vector can also be used. A recombinant vector can be prepared by cleaving purified DNA with a suitable restriction enzyme, and inserting the resultant at a restriction enzyme site of suitable vector DNA or the like to link with the vector. The host used for transformation is not particularly limited as long as it is capable of expressing the gene of interest. For example, it may be a bacterium (*Bacillus subtilis*, bacteria of the genus *Paracoccus*, etc.), a yeast, animal cells (COS cells, CHO cells, etc.), plant cells, insect cells or an insect. The method for introducing a recombinant vector into a host is known.

Moreover, the method for introducing a mutation into gene is the same as described above.

(3) Production of Carotenoid

According to the present invention, the above-described carotenoidogenic bacterium or transformant can be cultured in a predetermined medium to stably produce a carotenoid at a high concentration.

While the produced carotenoid is not particularly limited, it may be, for example, astaxanthin, canthaxanthin, zeaxanthin, β-cryptoxanthin, lycopene, β-carotene, adonirubin, adonixanthin, echinenone, asteroidenone or 3-hydroxyechinenone, preferably astaxanthin, canthaxanthin, zeaxanthin or β-cryptoxanthin, and more preferably astaxanthin or zeaxanthin. The carotenoids produced by the present invention may be of a single type or a combination of multiple types.

Hereinafter, a method for culturing the mutant carotenoidogenic bacterium or transformant of the present invention will be described.

A carotenoid-producing medium used for culture of the present invention may be added with any component as long as it allows growth of a carotenoidogenic bacterium or transformant and production of a carotenoid. Although any medium containing such an additive can be used, it is preferably a medium containing a carbon source, a nitrogen source, an inorganic salt and if necessary a vitamin or the like.

Examples of the carbon source include sugars such as glucose, sucrose, lactose, fluctose, trehalose, mannose, mannitol and maltose, organic acids such as acetic acid, fumaric acid, citric acid, propionic acid, malic acid, malonic acid and pyruvic acid, alcohols such as ethanol, propanol, butanol, pentanol, hexanol, isobutanol and glycerol, fats and oils such as soybean oil, rice bran oil, olive oil, corn oil, sesame oil and linseed oil, Among them, glucose or sucrose is preferably used. Among these carbon sources, one or more types can be used. While the amount added to the medium before culture (starting medium) varies according to the type of the carbon source and can appropriately be adjusted, it is usually 1-100 g, preferably 2-50 g per 1 L of the medium. Furthermore, the carbon source may be added not only to the starting medium but also preferably additionally supplied during culture successively or continuously.

As an inorganic salt as the nitrogen source, one or more types among ammonium salts such as ammonium nitrate, ammonium sulfate, ammonium chloride and ammonium phosphate, nitrates such as potassium nitrate, ammonia and urea can be used. While the amount added varies and can appropriately be adjusted according to the type of the nitrogen source, it is usually 0.1 g-20 g and preferably 0.2-10 g per 1 L of the medium.

Furthermore, as an organic nitrogen source, for example, one or more types among corn steep liquor (including filtrated product), Pharmamedia, soybean pulp, soybean powder, peanut meal, soy peptone, Distillers' solubles, dry yeast, yeast extract, casamino acid, glutamic acid and aspartic acid can be used. While the concentration added varies and can appropriately be adjusted according to the type of the nitrogen source, it is usually 0-80 g/L and preferably 1-30 g/L.

The inorganic nitrogen source and the organic nitrogen source are usually added to the starting medium, but they may also preferably be additionally supplied successively or continuously.

As the inorganic salt, for example, one or more types among phosphates such as potassium dihydrogen phosphate, dipotassium hydrogen phosphate and disodium hydrogen phosphate, magnesium salts such as magnesium sulfate and magnesium chloride, iron salts such as iron sulfate and iron chloride, calcium salts such as calcium chloride and calcium carbonate, sodium salts such as sodium carbonate and sodium chloride, manganese salts such as manganese sulfate, copper salts such as copper sulfate, zinc salts such as zinc sulfate, molybdenum salts such as sodium molybdate, nickel salts such as nickel sulfate, selenium salts such as sodium selenate, tungsten salts such as sodium tungstate, aluminum salts such as aluminum chloride, chromium salts such as chromium chloride, and potassium borate and iodide can be used. While the amount added varies and can appropriately be adjusted according to the type of the inorganic salt, it is usually 0.0001-15 g per 1 L of the medium. The concentration is preferably 0.02-15 g/L in a case of a phosphate, a magnesium salt, a calcium salt, a sodium salt or an iron salt, and preferably 0.1-15 mg/L when a manganese salt, a copper salt, a zinc salt, a molybdenum salt, a nickel salt, a selenium salt, a tungsten salt, an aluminum salt, a chromium salt, or a potassium borate or iodide is added. An inorganic salt is usually added to the starting medium, but it may also be additionally supplied successively or continuously.

As a vitamin, for example, cyanocobalamin, riboflavin, pantothenic acid, pyridoxine, thiamine, ascorbic acid, folic acid, niacin, p-aminobenzoic acid, biotin, inositol, choline or the like can be used. While the amount added varies and can appropriately be adjusted according to the type of the vitamin, it is usually 0.001-1000 mg and preferably 0.01-100 mg per 1 L of the medium. A vitamin is usually added to the starting medium, but it may also be additionally supplied successively or continuously.

According to the present invention, an antifoaming agent is preferably used in order to suppress foaming of the culture solution. Any type of antifoaming agent can be used as long as it serves to suppress generation of foam or eliminate generated foam, and has little inhibitory action against the produced bacterium. For example, an alcohol-based antifoaming agent, a polyether-based antifoaming agent, an ester-based antifoaming agent, a fatty acid-based antifoaming agent, a silicon-based antifoaming agent, a sulfonic acid-based antifoaming agent, and the like can be exemplified. While the amount added varies and can appropriately be adjusted according to the type of the antifoaming agent, it is usually 0.01 g-10 g per 1 L of the medium.

The antifoaming agent is usually added to the starting medium prior to sterilization. In addition, it may continuously or intermittently be added during the culture. As a method of adding an antifoaming agent during the culture, a method in which the antifoaming agent is automatically added once a sensor senses foam generation, a method in which the antifoaming agent is added constantly using a programmable timer, a method in which the antifoaming agent is added as a mixture with a feeding carbon source, nitrogen source or pH regulator or the like so as to link with the growth rate, or the like can be exemplified. An antifoaming agent added to the starting medium and an antifoaming agent added during the culture may be of the same type or they may be different according to their actions.

According to the present invention, the early pH of the medium is adjusted to 2-12, preferably 6-9 and more preferably 6.5-8.0. The pH in the above-mentioned range is preferably maintained during the culture as well. As the pH regulator, an aqueous sodium hydroxide solution, an aqueous potassium hydroxide solution, an aqueous sodium carbonate solution, ammonia water, ammonia gas, an aqueous sulfate solution or a mixture thereof can be exemplified.

According to the present invention, the medium is subjected to a sterilization treatment and thereafter used for culturing a bacterium. The sterilization treatment can appropriately be carried out by those skilled in the art. For example, the medium in a suitable vessel may be heat sterilized with an autoclave. Alternatively, it may be sterilized by filtration with a sterilizing filter.

A mutant carotenoidogenic bacterium or transformant of the present invention is inoculated onto a medium prepared as described above and cultured under predetermined conditions. Inoculation is carried out by appropriately growing the bacterial strain by seed culture using a test tube, a flask, a fermentation tank or the like, and adding the resulting culture solution to a carotenoid-producing medium. The medium used for the seed culture is not particularly limited as long as it is a medium that allows the carotenoidogenic bacterium to grow well.

Culture is carried out in a suitable culture vessel. While the culture vessel may appropriately be selected according to the culture volume, it may be, for example, a test tube, a flask and a fermentation tank.

The culture temperature is 15-40° C., preferably 20-35° C. and more preferably 25° C.-32° C. and culture is usually conducted for 1-18 days, preferably 2-12 days and more preferably 3-8 days under an aerobic condition. The aerobic condition, for example, may refer to shaking culture, aeration-agitation culture or the like, where the dissolved oxygen concentration is preferably controlled to lie within a certain range. The dissolved oxygen concentration can be controlled, for example, by varying the rotation speed for agitation, the ventilation volume, the internal pressure or the like. The dissolved oxygen concentration is preferably controlled to 0.3-10 ppm, more preferably 0.5-7 ppm and still more preferably 1-5 ppm.

The number of bacterial cells or the number of transformants of a carotenoidogenic bacterium after culturing the mutant carotenoidogenic bacterium or transformant of the present invention can be measured by OD. In addition, the carotenoid contained in the resulting cultured product or the carotenoid collected from the cultured product after culturing the carotenoidogenic bacterium or transformant can be quantified by high performance liquid chromatography. After culturing the carotenoidogenic bacterium or transformant, the carotenoid can be collected from the resulting cultured product as described above.

Examples of the cultured product include a culture solution, a culture supernatant, a concentrated bacterial cell solution, wet bacterial cells, dry bacterial cells and a bacterial cell lysate. The culture supernatant can be prepared by subjecting the culture solution to a centrifugal treatment or a filtration treatment to remove the bacterial cells from the culture solution. The concentrated bacterial cell solution can be obtained by subjecting the culture solution to centrifugation or membrane filtration concentration. The wet bacterial cells can be obtained by centrifuging or filtrating the culture solution. The dry bacterial cells can be obtained by drying wet bacterial cells or a concentrated bacterial cell solution by a general drying method. The resulting carotenoid-containing dry bacterial cells can directly be used as feed additives.

The yield by fermentation culture is at least 150 mg/L, for example, 150 mg/L, 400 mg/L, 2000 mg/L or 4000 mg/L of carotenoid. While the amount of the carotenoid contained in the culture solution varies depending on the bacterial cells used, it may contain, for example, 400 mg/L-4000 mg/L and still more preferably 500 mg/L-3500 mg/L of carotenoid.

The bacterium of the present invention has production capacity of an amount at least 5 times, preferably 10 times or more the carotenoid production amount of a carotenoidogenic bacterium that does not have the gene encoding the protein comprising the mutant amino acid sequence of DXS and/or DPS.

According to the present invention, the method for collecting the carotenoid from the above-described cultured product is not particularly limited, and any method that allows stable and efficient carotenoid collection can be employed. These methods can appropriately be selected from known extraction and purification techniques and carried out by those skilled in the art. Alternatively, according to the present invention, the above-described cultured product can also be used as a carotenoid-containing composition.

Prior to extraction, the cultured product may be subjected to one or more treatments among a chemical treatment using an alkali reagent or a surfactant, a biochemical treatment using a lytic enzyme, a lipolytic enzyme or a proteolytic enzyme, or a physical treatment like ultrasonic waves or pulverization.

For example, in a case where a carotenoid is extracted from the cultured product, a solvent used for extraction and washing is not particularly limited, and the it may be a lower alcohol such as methanol, ethanol and isopropanol, acetone, tetrahydrofuran, methyl ethyl ketone, methyl isobutyl ketone, dichloromethane, chloroform, dimethyl formamide or dimethyl sulfoxide.

If oxidization of the carotenoid needs to be minimized during the extraction operation, it may be treated in an inert gas atmosphere such as nitrogen gas. Alternatively, an antioxidant used for pharmaceutical products and food can be selected and added to the extraction solvent. Alternatively, these treatments can be combined. Moreover, in order to minimize photolysis of the carotenoid, the treatment can be conducted under a condition without exposure to light.

The thus-resulting extract can directly be used as the carotenoid, or it may be purified before use.

While a method for separating the bacteria or the like remaining in the extract after the extraction operation is not particularly limited, membrane filtration, centrifugation, decantation or the like can be employed.

A method for obtaining the carotenoid precipitate from the extracted liquid generally includes heating and/or concentration under reduced pressure, or crystallization. Alternatively, the carotenoid pigments can be separated without concentration by precipitation of carotenoid pigments at a low temperature, or precipitation with an acidic/alkaline agent or a salt. For an industrial use, crystallization is favorable.

The resulting carotenoid precipitate may be suspended and agitated using a solvent such as a small amount of a lower alcohol for washing if necessary. While the washing procedure is not particularly limited, examples of a practically preferable method include a method employing filtration following the suspension/agitation, and a method in which a liquid is passed from top of the precipitate.

The resulting cultured product, extract or purified product may be used as a carotenoid alone or as a mixture at arbitrary proportions.

2. Conformational Analysis of Enzyme Involved in Astaxanthin Synthesis Pathway Since the mutations of the 225th amino acid residue of DXS and the 305th amino acid residue of DPS are found to play an important role in carotenoid synthesis, conformational analyses of these enzymes can be conducted.

According to the present invention, point mutations in two types of enzymes (referred to as Enzymes A and C) on the astaxanthin synthesis pathway were identified. Since the increase in the astaxanthin production was considered to result from the mutations caused in these enzymes, conformational models were constructed for the two types of enzymes having the identified mutations to predict the effects of the amino acid substitutions due to the mutations.

Enzyme A was deduced to be 1deoxy-D-xylulose 5-phosphate synthase (DXS). The identified amino acid mutation G225D was in the disordered region near the active site. From the conformational model, mutation G225D in Enzyme A was deduced to cause a structural change in Enzyme A that was similar to that caused by the mutation in the disordered region that was known to enhance DXS activity, thereby predicting enhanced enzymatic activity in the mutant G225D enzyme. Considering that DXS is under the control of feedback inhibition of IPP, the amount of IPP produced is suggested to increase because feedback inhibition does not work in the mutant G225D enzyme. The increase in the supply of IPP, i.e., a raw material of astaxanthin, due to mutation G225D in Enzyme A seems to cause the increase in the astaxanthin production amount.

Enzyme C was deduced to be decaprenyl diphosphate synthase. From the conformational model, the identified mutation A305V was deduced to cause steric hindrance with the surrounding amino acid residues and destabilizes the conformation of Enzyme C. FPP and IPP as the raw materials of decaprenyl diphosphate as well as the substrates of Enzyme C are also raw materials for the astaxanthin synthesis. A decrease in the Enzyme C activity due to destabilization is suggested to decrease the amounts of FPP and IPP digested by Enzyme C. As a result, the amounts of FPP and IPP that can be used for the astaxanthin synthesis are increased, which is considered to increase the astaxanthin production amount.

Accordingly, two effects, namely, the increase in the IPP production amount due to the enhancement of the Enzyme A activity and the increase in the IPP supply to the astaxanthin synthesis pathway due to the decrease in the Enzyme C activity, were deduced to be the effects of the mutations identified this time on the astaxanthin synthesis pathway. These effects appear to result in the increase in the astaxanthin production amount.

EXAMPLES

Hereinafter, the present invention will be described more specifically by way of examples. The scope of the present invention, however, should not be limited to these examples.

Example 1

(1) Mutation Treatment of Genome Analysis of Bacteria of Genus *Paracoccus*

Method of Mutation Treatment

Screening was carried out for several times by using UV, NTG (nitrosoguanidine) and the like as mutagens on the parent strain (strain E-396) and adopting various selection pressures. Screening was conducted using the astaxanthin yield as an indicator.

Method of Genome Analysis

Following genome sequencing using PacBio RS II (from Pacific Biosciences) or MiSeq (Illumina) sequencer, a genome analysis was carried out by using an analysis software such as SMART Cell 8 Pac V3 (from Pacific Biosciences), MiSeq Control Software (MCS) v2.4.1.3, Real Time Analysis (RTA) v1.18.54, or bcl2fastq v 1.8.4 (Illumina).

Results from Genome Analysis (Identification of Mutation Site)

The mutation site was identified by sorting out those belonging to the genus *Paracoccus* among the amino acid sequences of enzyme genes recorded in the Kyoto Encyclopedia of Genes and Genomes (KEGG) which have high homology with the amino acid sequence of the region that was considered to be the protein having the mutation point from the genome analysis, and further conducting a conformational analysis of the enzyme based on these information to find out a template having a common sequence, thereby determining the final enzyme name of the amino acid sequence of the protein having the mutation site.

(2) Astaxanthin Yield (i) Culture Conditions

Strokes of test tubes: 330 rpm, 28° C., pH 7.2, amount of medium 8 ml/tube
Culture time: 72 hours
Medium:
8 ml of a medium with the following composition was placed in a test tube provided with a cotton plug and having an inner diameter of 18 mm and sterilized in an autoclave at 121° C. for 15 minutes to prepare a test tube medium for seeding. The raw materials used for the test tube medium for seeding were those from lots that were confirmed to allow sufficient growth of bacterial cells.
Sucrose: 30 g/L
Corn steep liquor: 30 g/L
Potassium dihydrogen phosphate: 1.5 g/L
Disodium hydrogen phosphate dodecahydrate: 3.8 g/L
Calcium chloride dihydrate: 5.0 g/L
Magnesium sulfate heptahydrate: 0.7 g/L
Iron sulfate heptahydrate: 1.0 g/L
pH 7.2
Next, 7.2 ml of a medium with the following composition was placed into each of test tubes provided with a cotton plug and having an inner diameter of 18 mm to prepare five test tube media for production. The raw materials used for the test tube media for production were those from lots that were confirmed to allow insufficient growth of bacterial cells.

Glucose: 30 g/L
Filtrated corn steep liquor product: 30 g/L
Ammonium sulfate: 1.5 g/L
Potassium dihydrogen phosphate: 1.5 g/L
Disodium hydrogen phosphate dodecahydrate: 3.8 g/L
Calcium chloride dihydrate: 5.0 g/L
Magnesium sulfate heptahydrate: 0.7 g/L
Iron sulfate heptahydrate: 1.0 g/L
Silicon-based antifoaming agent: 0.2 g/L (ii) Results The specific productivity of each strain is shown in FIG. 1.

According to this example, strain ASB-57 that had production capacity 10 times or more that of strain E-396 carotenoid was acquired.

Example 2

Conformational Analysis of Enzyme Involved in Astaxanthin Synthesis Pathway

1. Conformational Data and Procedure

The conformational models of Enzymes A and C were constructed by homology modeling. For the modeling, software Swiss-Pdb viewer and SWISS-MODEL were used [1, 2]. Mutant models were prepared with Swiss-Pdb viewer. The command "mutate" was used to substitute the amino acid residues, the command "compute energy" was used to compute intramolecular energy, and the command "energy minimization" was used to calculate for energy minimization. Preparation of a complex model with the substrate or the like, detection of the residues in the vicinity of the substrate, measurement of interatomic distance, and display of the conformation were conducted using software Waals (Altif Labs. Inc.). A conformational model of a low-molecular compound was prepared with MarvinSketch (ChemAxon Ltd.).

The coordinate data of the conformation of the template structure was acquired from the protein conformational database, Protein DataBase (PDB) (http://www.rcsb.org/pdb/). The template structures that had the highest amino acid matching degree with each of Enzymes A and C were used among the data registered with PDB. The conformational data used as the templates for the homology modeling is shown in Table 1.

TABLE 1

Conformational data used for homology modeling

| Enzyme | PDB ID | Protein | Document |
|---|---|---|---|
| Enzyme A | 2O1X | 1-Deoxy-D-xylurose-5-phophate synthase | [3] |
| Enzyme C | 3MZV | Decaprenyl diphosphate synthase | [4] |

2. Construction of Conformational Model of Enzyme A and Analysis of Mutant

Enzyme A is 1-deoxy-D-xylulose 5-phosphate synthase (DXS) that synthesizes 1-deoxy-D xylulose 5-phosphate from pyruvic acid and D-glyceraldehyde 3-phosphate in the deoxyxylulose pathway, i.e., one of isoprenoid biosynthesis pathways that biosynthesize isoprenyl diphosphate (IPP) that serves as a raw material for astaxanthin synthesis.

Mutation G225D identified from the constructed conformational model of Enzyme A by the genome analysis was found to exist in the disordered region in the vicinity of the active site, where the mutation had been reported to enhance the enzymatic activity of DXS in several cases. From the results of the analysis of the mutant model, mutation G225D in Enzyme A was deduced to induce a structural change similar to that caused by the mutation known to enhance the DXS activity, and thus the mutant G225D enzyme was also predicted to have enhanced DXS enzymatic activity similar to the known mutation. Enhancement of the DXS activity increases IPP supply as the raw material of astaxanthin, which is considered to increase the amount of astaxanthin produced.

2.1. Enzymatic Reaction of 1-deoxy-D-xylulose 5-phosphate synthase

Enzyme A, 1-deoxy-D-xylurose-5-phosphate synthase (DXS), synthesizes 1-deoxy-D-xylulose 5-phosphate from pyruvic acid and D-glyceraldehyde 3-phosphate in the presence of a magnesium ion (Mg). The catalytic reaction requires thiamine pyrophosphate (TPP) as a coenzyme. First, TPP coenzyme attaches to the substrate pyruvic acid to give a hydroxyethyl-TPP intermediate. Reaction between this intermediate and glyceraldehyde 3-phosphate generates 1-deoxy-D-xylulose 5-phosphate. The enzymatic reaction of Enzyme A is shown below.

Chemical formula 1

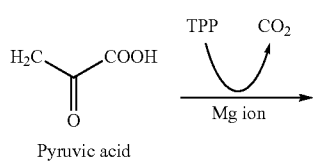

Pyruvic acid

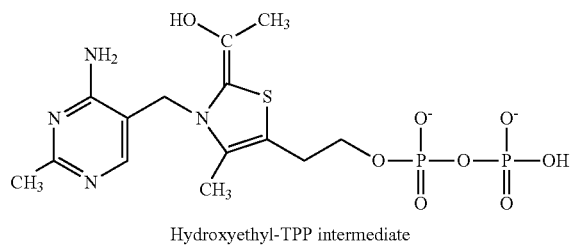

Hydroxyethyl-TPP intermediate

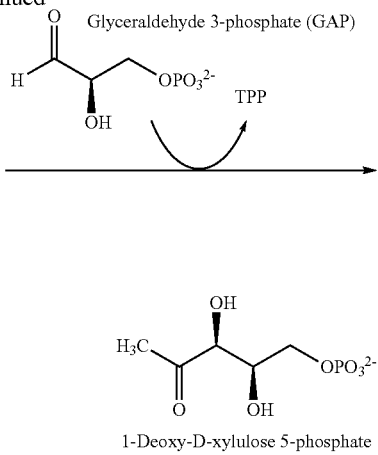

1-Deoxy-D-xylulose 5-phosphate

2.2. Construction of Conformational Model of Enzyme A

(1) Construction of Conformational Model of Enzyme A by Homology Modeling

Figure 2:
FIG. 2 An image showing a template structure of Enzyme A.

The conformational model of Enzyme A was constructed by homology modeling based on the conformation (PDB ID:2O1X) [3] of *Deinococcus radiodurans* (*D. radiodurans*)-derived 1-deoxy-D-xylurose-5-phosphate synthase (DXS, template) (FIG. 2) whose conformation of the complex with TPP coenzyme had been determined by X-ray crystallography.

Figure 3A:
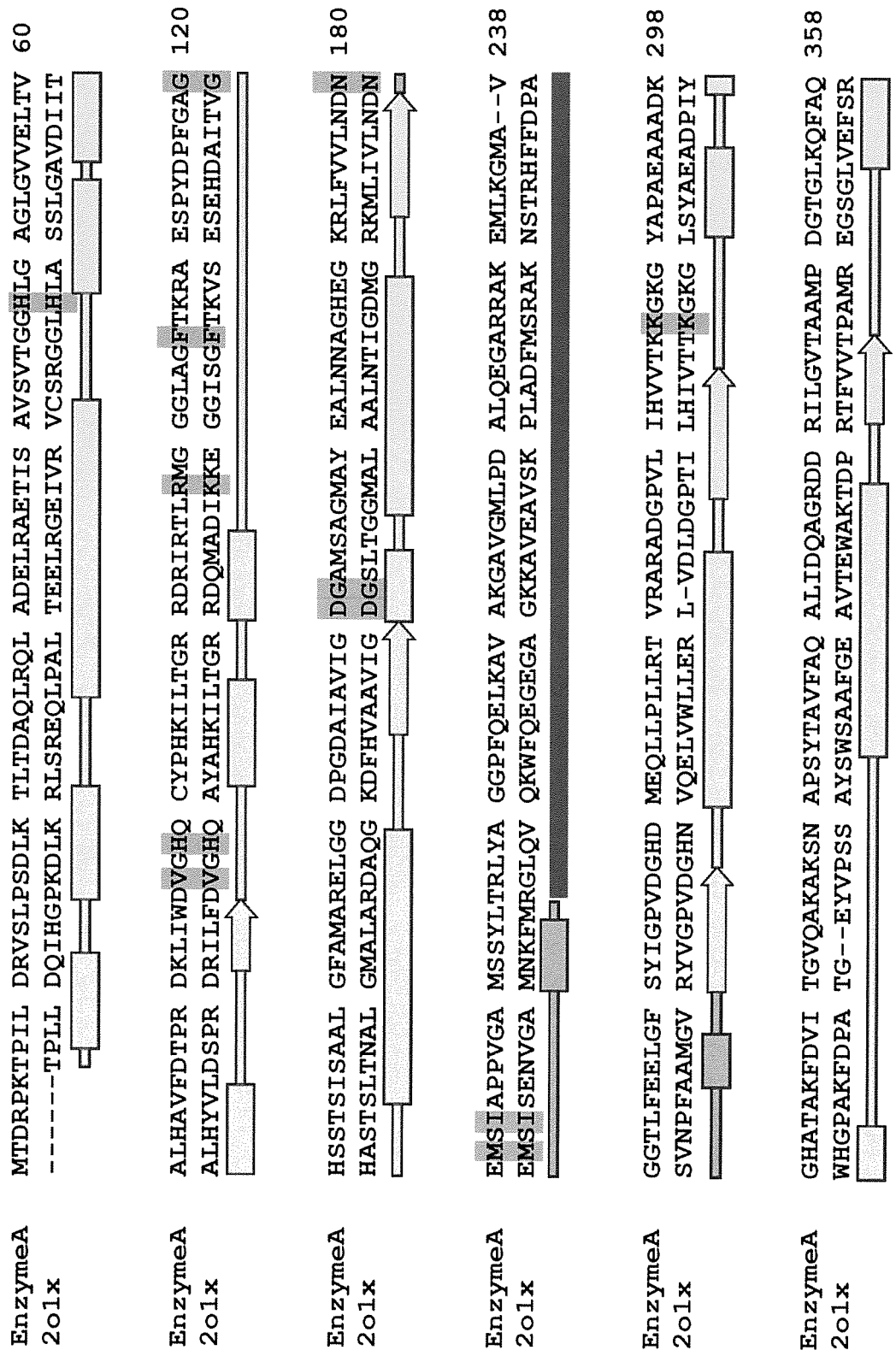
FIG. 3A A depiction showing the alignment between Enzyme A and the template structure (2O1X). The deduced active sites are depicted in green. The disordered region is represented by a blue bar.
Figure 3B:
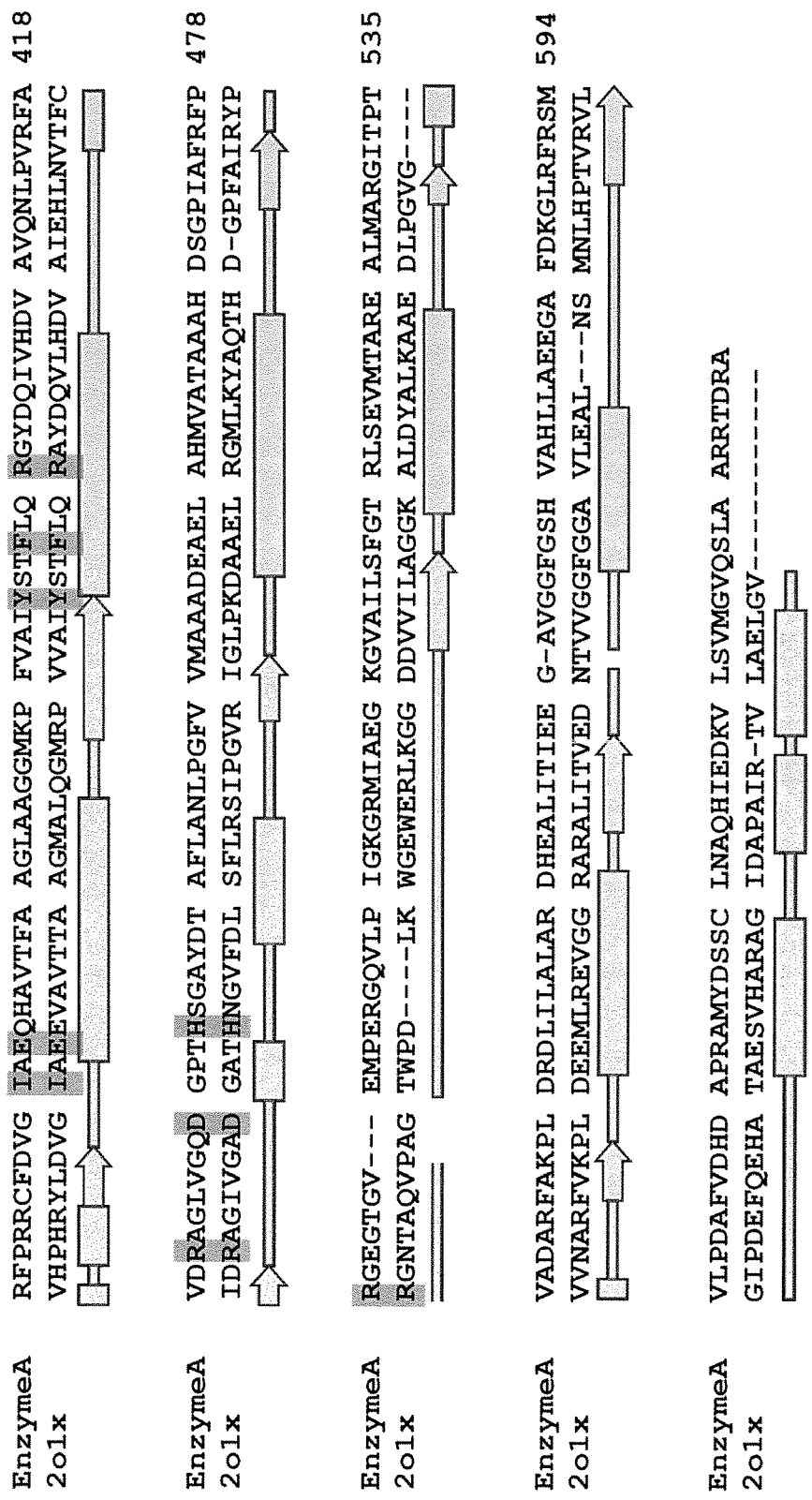
FIG. 3B A depiction showing the alignment between Enzyme A and the template structure (2O1X). The deduced active sites are depicted in green. The disordered region is represented by a blue bar.

Homology modeling was carried out based on the conformation alignment between Enzyme A and the template structure (FIGS. 3A and 3B).

The amino acid matching degree between Enzyme A and *D. radiodurans*-derived DXS was 44.1%. In the conformation of the template DXS, the region of the amino acid residues 199-242 (44 residues) was a disordered region and thus the positions of the atoms were unspecified by X-ray crystallography. Therefore, a conformational model of the amino acid residues 7-630 excluding the residues 196-238 (43 residues) corresponding to the disordered region of Enzyme A was constructed. Then, TPP and Mg were embedded by superimposing the conformational model of Enzyme A and the template structure to prepare a complex model of Enzyme A and TPP. FIG. 4 shows the template structure and the constructed model structure.

Similar to the template structure, Enzyme A formed a homodimer and had a TPP binding site and a substrate binding site in each of the subunits. The monomer of Enzyme A consists of three domains, namely, domain I (residues 1-319), domain II (residues 320-495) and domain III (residues 496-629).

(2) Preparation of Enzyme A-Substrate Complex Models

In order to deduce the amino acid residue responsible for the bond between Enzyme A and the substrates, complex models having the substrates bonded to Enzyme A were constructed. Since the coordinates of pyruvic acid and glyceraldehyde 3-phosphate as the substrates were not determined in the template structure 2O1X, first, a model of a complex with the hydroxyethyl-TPP intermediate that had TPP coenzyme attached to pyruvic acid was prepared by embedding the hydroxyethyl-TPP intermediate by superimposition based on a conformation in which a related *Saccharomyces cerevisiae* (*S. cerevisiae*)-derived transketolase (TK) was bound with the hydroxyethyl-TPP intermediate (PDB ID: 1GPU) [6], to detect the pyruvic acid binding site. Similarly, a model of an Enzyme A-glyceraldehyde 3-phosphate complex was prepared by embedding erythrose-4-phosphate based on a conformation of *S. cerevisiae*-derived TK with erythrose-4-phosphate (PDB ID: 1NGS) [7] and further preparing a glyceraldehyde 3-phosphate model from erythrose-4-phosphate.

FIG. 5 shows the model structure of the Enzyme A-substrate complex.

2.3. Deduction of Active Site of Enzyme A

In order to deduce the amino acid residue binding the coenzyme and the substrate, interactions between the TPP intermediate, GAP and Mg were examined in the complex model of Enzyme A and the coenzyme.

(1) Binding Site of TPP Coenzyme

Similar to the template structure, TPP was located between domain I and domain II in the complex model of Enzyme A and TPP, where the pyrimidine ring of TPP was bound to domain II and the phosphate group was bound to domain I.

Figure 6:
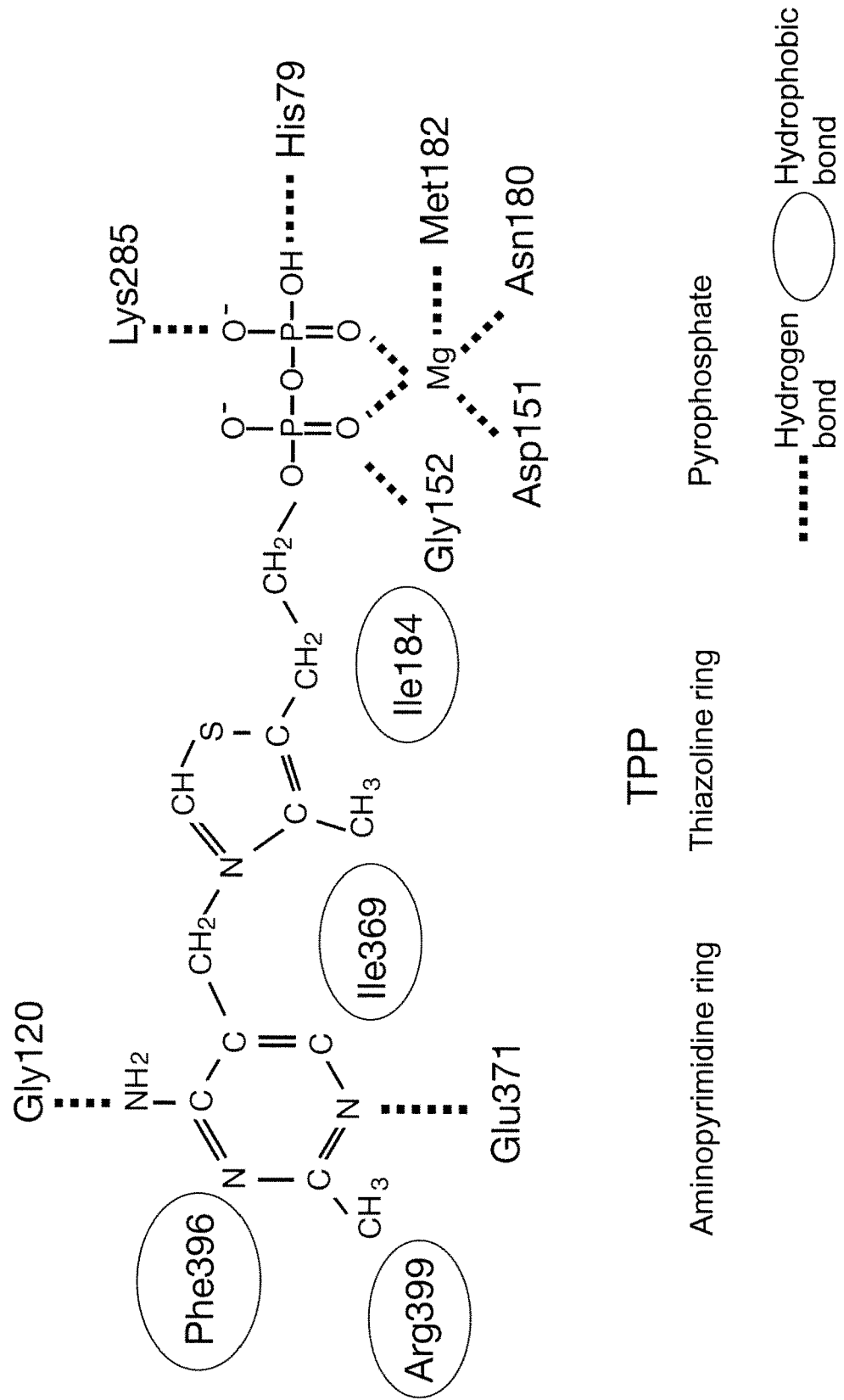
FIG. 6 A depiction showing the interaction between Enzyme A and TPP coenzyme.

TPP consists of an aminopyrimidine ring, a thiazoline ring and pyrophosphate (FIG. 6). The aminopyrimidine ring binds to closely fit inside the binding pocket of Enzyme A. The side chains of Phe396 and Ile369 are bound via hydrophobic interactions to sandwich the aminopyrimidine ring. Especially, a strong bond via π stacking was deduced between the side chain of Phe396, the cyclic phenyl group, and the aminopyrimidine ring. The main-chain oxygen of Gly120 and the side-chain oxygen of Glu371 formed hydrogen bonds with the nitrogen atom at position 1 in the aminopyrimidine ring. The hydrogen bond between the nitrogen atom at position 1 in the pyrimidine ring of TPP and Glu residue is important for the catalytic reaction via TPP, and is known to be conserved in an enzyme that uses TPP as a coenzyme. The side chain of Arg399 is predicted to form the binding pocket not only via the hydrophobic bond but also via hydrogen bonds with the side chains of the peripheral amino acid residues Glu371 and Ser122. As to the interactions with the thiazoline ring, hydrophobic bonds with Ile184 and Ile369 were observed. As to the interactions with pyrophosphate, hydrogen bonds with the main chain of Gly152, the side chain of Lys285 and the side chain of His79 were deduced.

The bond with the TPP coenzyme requires Mg. Mg is located between the two phosphate groups of TPP, and Mg was deduced to bind with the side chains of Asp151 and Asn180 and the main chain of Met182. As to DXS, the sequence of GDGX25-30N is known to be conserved as a TPP binding motif [3]. The amino acid sequence Gly150-Asp151-Gly152-Asn180 including Asp151 and Asn180 that were deduced to form bonds with Mg in Enzyme A matches this motif.

Thus, the carbons in the aminopyrimidine ring and the thiazoline ring of TPP were deduced to have hydrophobic interactions with hydrophobic residues Ile184, Ile369, Phe396 and Arg399 of Enzyme A. Moreover, two nitrogen atoms in the aminopyrimidine ring were deduced to form hydrogen bonds with Gly120 and Glu371. Besides the hydrogen bonds with His79, Gly152 and Lys285, the pyrophosphate was deduced to form hydrogen bonds with Asp151, Asn180 and Met182 via Mg. FIG. 7 shows the amino acid residues that were deduced to be responsible for the bonds with TPP.

(2) Interaction with Pyruvic Acid

Pyruvic acid as the substrate reacts with TPP and forms a hydroxyethyl-TPP intermediate. From the complex model of Enzyme A and the hydroxyethyl-TPP intermediate, a hydrophobic interaction with Val77 and a hydrogen bond with His432 were deduced as interactions with the pyruvic acid-derived hydroxyethyl group. These amino acid residues were considered to be involved in the bond with pyruvic acid. FIG. 8 shows amino acid residues that were predicted to have interactions with the hydroxyethyl groups.

(3) Interaction with glyceraldehyde 3-phosphate

As the amino acid residues that interact with the substrate glyceraldehyde 3-phosphate (GAP), hydrogen bonds with His48, Tyr393, Arg421, Asp428 and Arg479 were deduced (FIG. 9).

His48 and Asp428 form hydrogen bonds with the aldehyde groups of GAP. Tyr393, Arg421 and Arg479 were deduced to form hydrogen bonds with the phosphate groups of GAP.

The above-described deduced active sites are shown in Tables 2-4.

TABLE 2

Amino acid residues predicted to have interaction with hydroxyethyl-TTP intermediate detected in Enzyme A

| hydroxyethyl-TTP | | Enzyme_A | interaction |
|---|---|---|---|
| Amino-Pyrimidine | Gly120 | main-chain | hydrogen bond |
| | Ile369 | side-chain | hydrophobic interaction |
| | Glu371 | side-chain | hydrogen bond |
| | Phe396 | side-chain | hydrophobic interaction |
| | Arg399 | side-chain | hydrophobic interaction |

TABLE 2-continued

Amino acid residues predicted to have interaction with hydroxyethyl-TTP intermediate detected in Enzyme A

| hydroxyethyl-TTP | | Enzyme_A | interaction |
|---|---|---|---|
| Thiazolium | Ile184 | side-chain | hydrophobic interaction |
| | Ile369 | side-chain | hydrophobic interaction |
| PO4 | His79 | side-chain | hydrogen bond |
| | Gly152 | main-chain | hydrogen bond |
| | Lys285 | side-chain | hydrogen bond |
| Mg | Asp151 | side-chain | hydrogen bond |
| | Asn180 | side-chain | hydrogen bond |
| | Met182 | main-chain | hydrogen bond |
| Hydroxyethyl | Val77 | side-chain | hydrophobic interaction |
| | His432 | side-chain | hydrogen bond |

TABLE 3

Amino acid residues predicted to have interaction with glyceraldehyde 3-phosphate detected in Enzyme A

| GAP | | Enzyme_A | interaction |
|---|---|---|---|
| Glyceraldehyde | His48 | side-chain | hydrogen bond |
| | Asp428 | side-chain | hydrogen bond |
| PO4 | Tyr393 | side-chain | hydrogen bond |
| | Arg421 | side-chain | hydrogen bond |
| | Arg479 | side-chain | hydrogen bond |

TABLE 4

Amino acid residues at deduced binding sites in Enzyme A

| binding site | residue |
|---|---|
| TTP | His79 |
| | Gly120 |
| | Gly152 |
| | Ile184 |
| | Lys285 |
| | Ile369 |
| | Glu371 |
| | Phe396 |
| | Arg399 |
| Mg | Asp151 |
| | Asn180 |
| | Met182 |
| Pyrvate | Val77 |
| | His432 |
| GAP | His48 |
| | Asp428 |
| | Tyr393 |
| | Arg421 |
| | Arg479 |

Figure 10:
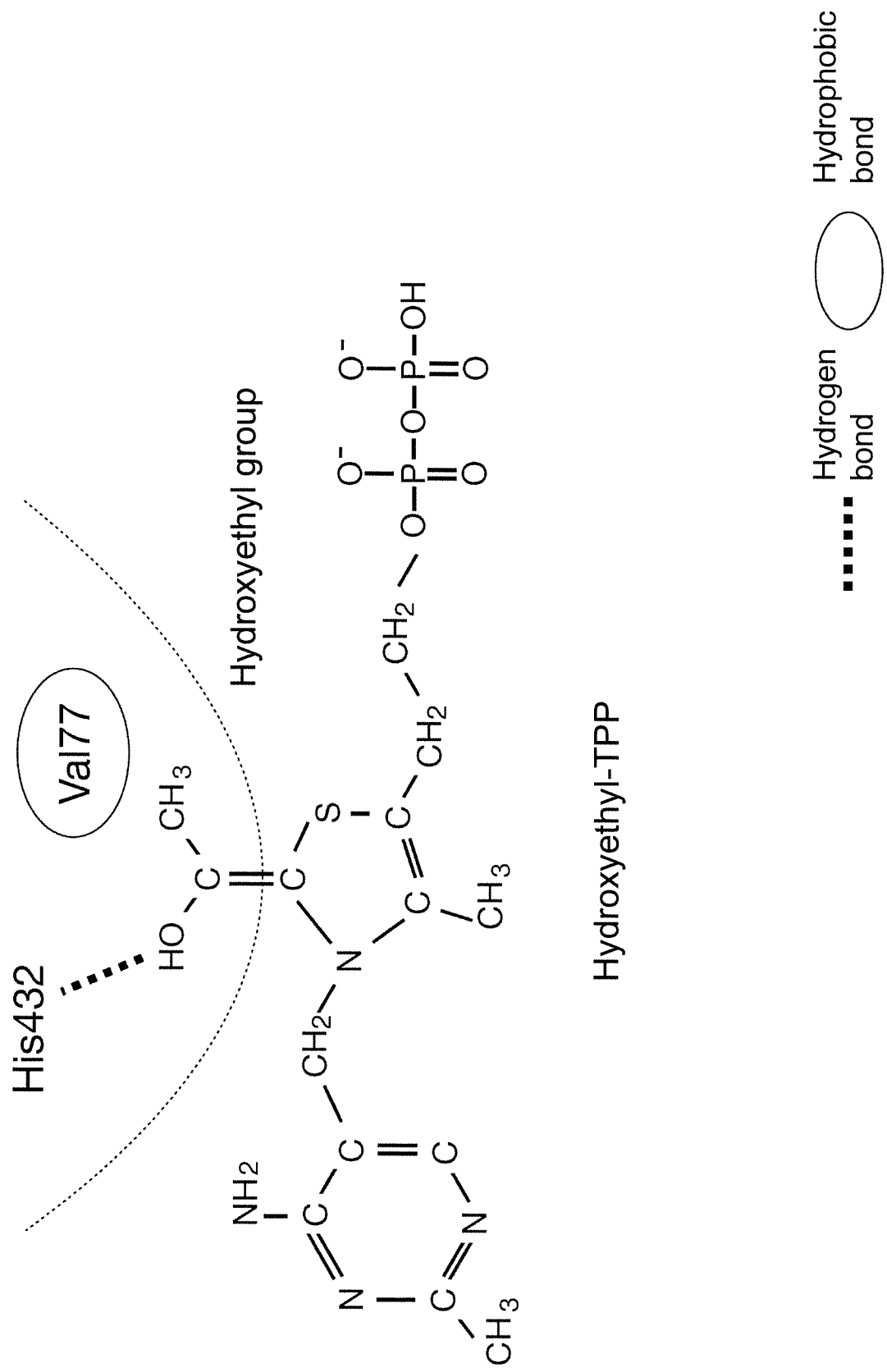
FIG. 10 A depiction showing the interaction between Enzyme A and the substrate pyruvic acid.
Figure 11:
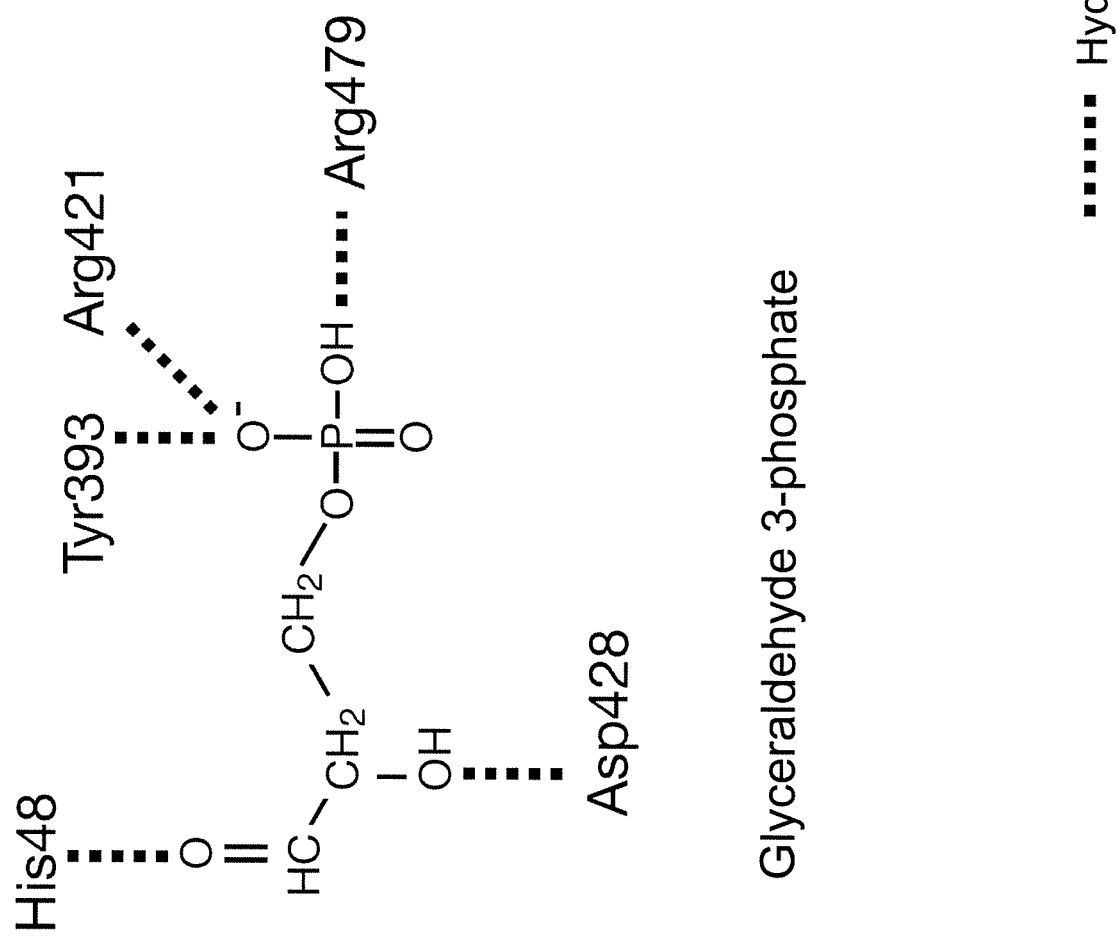
FIG. 11 A depiction showing the interaction between Enzyme A and the substrate glyceraldehyde 3-phosphate.

Furthermore, the binding modes between Enzyme A and TPP coenzyme, the binding modes between Enzyme A and pyruvic acid, the binding modes between Enzyme A and glyceraldehyde 3-phosphate are shown in FIGS. 6, 10 and 11, respectively.

Since Enzyme A retained active sites that bind TPP coenzyme and substrates pyruvic acid and GAP like template *D. radiodurans*-derived DXS, it was predicted to have the enzymatic activity of DXS. Other than *D. radiodurans*-derived DXS, these amino acid residues are also known to be highly conserved in DXS from *E. coli* and the like and *S. cerevisiae*-derived TK [3].

In *E. coli* DXS, substitution of the amino acid residues corresponding to Glu370, Arg399 and Arg479 of Enzyme A to Ala is found to result deactivation [3]. According to Document [8], enzymatic activity was generally deactivated in all of the experiments of mutating amino acid residues of *E. coli* DXS corresponding to His48, Glu371 and Asp428 of Enzyme A. These amino acid residues are predicted to be important for DXS activity in Enzyme A as well.

2.4. Effect of Mutation G225D in Enzyme A

Mutation G225D in Enzyme A was present in the disordered region (residues 196-238) whose conformation was unspecified. In order to deduce the effect of this mutation on the conformation of Enzyme A, the previous findings, the conformational location of the disordered region and the relationship with the active site were examined.

(1) Regarding Mutation in Known Disordered Region

So far, two mutations caused in the disordered region of each of Muscat and *E. coli* DXS, i.e., a total of four mutations, were all reported to increase the enzymatic activity.

In Muscat (*Vitis vinifera*)-derived DXS, mutation K284N was reported to result an increase in the activity that was about twice as high as that of the wild-type in Vmax and Kcat/Km, and overexpression was reported to greatly increase the amount of monoterpene produced [9].

Moreover, inventions related to mutations K284N and R306C in Muscat and mutations K213N and K234C in *E. coli* are known (Japanese Patent Application Publication No. 2014-500710, US20130276166). This invention relates to a method for increasing the amount of terpene produced by enhancement of DXS activity, where the amount of terpene produced increased by the single-residue mutation in all of the four cases.

The positions of mutations in Enzyme A and *E. coli* and Muscat DXS that resulted increase in the enzymatic activity are shown in FIG. 12.

K284N and R306C in Muscat, and K213N and K234C in *E. coli* all existed in the disordered region (blue). Mutation G225D in Enzyme A also existed in the disordered region. Based on the amino acid sequence alignment, the active site (green) of DXS was conserved and Enzyme A was predicted to have a reaction mode similar to the reaction modes of these DXS. The active site existed on the N-terminal side (magenta) of the disordered region.

Thus, multiple mutations in the disordered region of DXS increased the enzymatic activity of DXS, and mutagenesis in this region of interest was predicted to give some effect to the DXS activity.

(2) Conformational Location of Mutation G225D (Disordered Region) in Enzyme A FIG. 13 shows the location of the disordered region (residues 196-238) that has mutation G225D in Enzyme A in a blue dotted line.

The region of interest is located in the vicinity of the binding site of TPP coenzyme essential for DXS activity. Active sites Asn180, Met182 and Ile184 exist in the loop (magenta) on the N-terminal side of the region of interest. The side chain of Asn180 and the main chain of Met182 bind to Mg. The side chain of Ile184 form a hydrophobic bond with TPP. It is considered important that this loop has a suitable structure such that TPP essential for DXS activity can bind with Mg. In document [9], the physiological role of the region of interest was unclear but the region of interest was considered to exist near the active site, and the mutation in the region of interest rationally seemed to have an effect on the activity of the enzyme. Since the region of interest exists in the vicinity of the TPP binding site both in terms of the amino acid sequence and the conformation as shown in FIGS. 12 and 13, it is highly likely that the mutation in the region of interest has an effect on these active sites.

Figure 14:
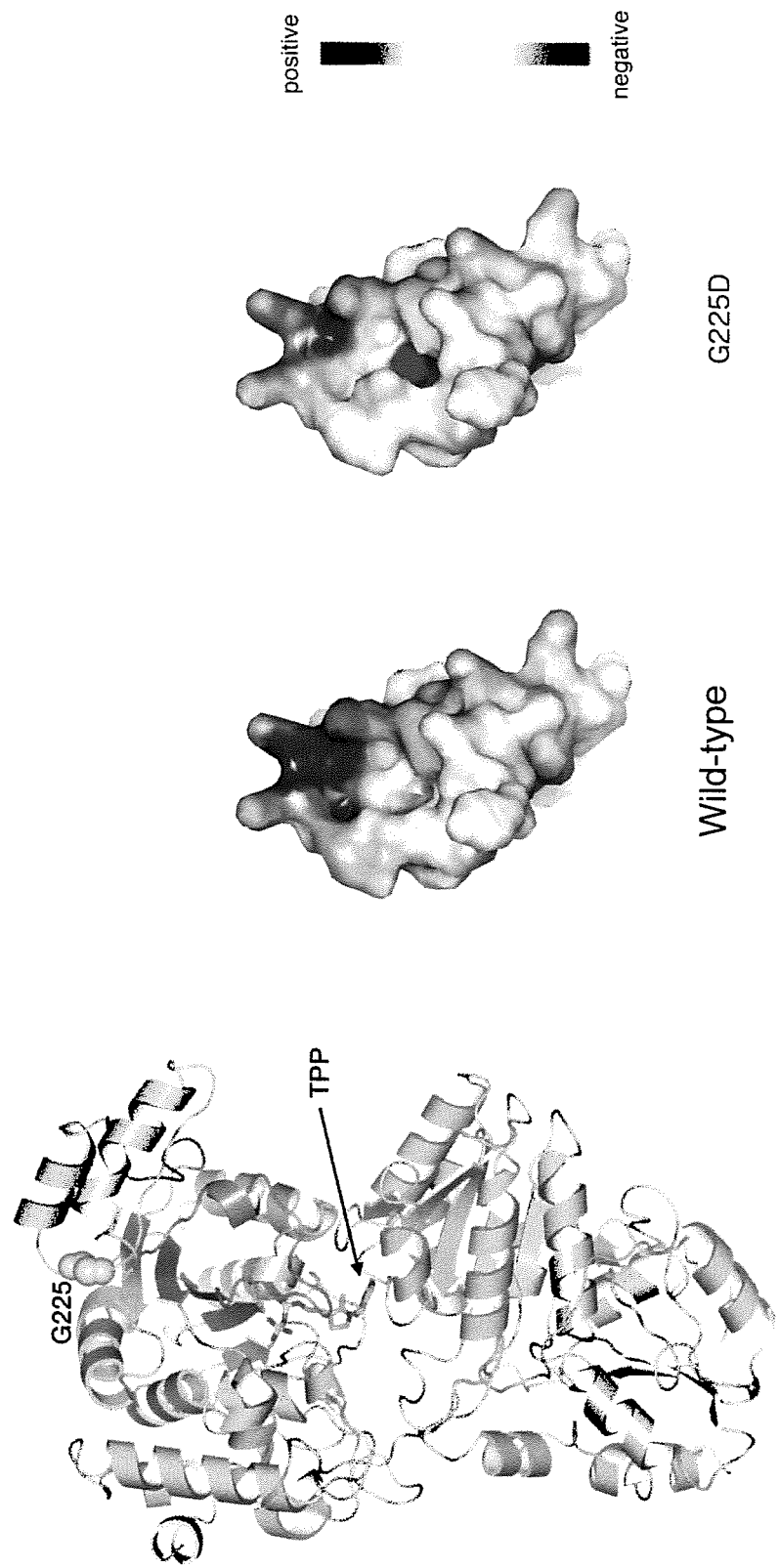
FIG. 14 Images showing a model structure of the disordered region of Enzyme A. The model structure of the disordered region (light blue) in Enzyme A (left) and the electrostatic potential maps of the model structures of the disordered regions (right).

(3) Preparations of Model of Disordered Region of Enzyme A and Mutant G225D Enzyme Next, in order to examine the effect of mutation G225D in Enzyme A on the conformation of the disordered region, a model structure was prepared for the disordered region across residues 196-238 (43 residues) of Enzyme A. In document [9] that reported mutation K284N in Muscat, a model of the disordered region of Muscat DXS was prepared to observe the change in the electrostatic potential by the mutation. For reference, a similar analysis was conducted for Enzyme A as well. A conformational model was prepared by homology modeling based on a fragment structure of an amino acid sequence that was highly homologous with the disordered region of Enzyme A. As a template structure, a fragment 1AL7 having the highest amino acid matching degree (34%) among the conformations registered in PDB was used. Even though the disordered region was predicted to have a fluctuated structure, it was considered to serve as a reference of a folding that is likely to form the region of interest. The prepared model is shown in FIG. 14 (left).

Furthermore, a conformational model of the mutant G225D enzyme was prepared by substituting the mutation site Gly225 with Asp. Since Gly225 is located on the surface, substitution with Asp exposes the side chain of Asp on the surface. The results from mapping electrostatic potential on the surface profile of the prepared conformational model are shown in FIG. 14 (right). Blue represents a positive (positively charged) region while red represents a negative (negatively charged) region.

While there is a strong positively charged region in the wild type, a weakened positive charge and a strengthened negative charge can be confirmed in the mutant G225D enzyme. In the wild type, the side chains of positively charged Arg227, Arg228, Lys230 and K234 aggregate, and form a strong positively charged region. Since the uncharged Gly225 existing in this region was replaced with the negatively charged Asp, the positive charge near Asp225 seemed to have weakened. This result shows similar tendency to document [9], that is, the change in the electrostatic potential due to mutation K284N in Muscat, i.e., the change in the electrostatic potential from a positive charge to a negative charge on the surface of the disordered region. The structural change in the disordered region caused by G225D in Enzyme A was predicted to have an effect similar to the mutation in Muscat on the active site including the TPP binding site, suggesting that the mutant G225D of Enzyme A had an increased enzymatic activity similar to the mutant K284N of Muscat due to this effect.

2.5. Effect of Mutation G225D in Enzyme A on Astaxanthin Synthesis Pathway

Accordingly, mutation G225D in Enzyme A was confirmed to occur in the disordered region of Enzyme A, and this region was confirmed to exist in the vicinity of the TPP binding site that was essential for the activity. So far, multiple mutations in this region have been found to enhance the enzymatic activity of DXS, suggesting that G225D mutation causes a structural change similar to that caused by the mutations that are known to enhance the DXS activity.

From the location of the disordered region confirmed with the conformational model, mutation in the disordered region seems to have some effect on the TPP binding region to enhance the enzymatic activity at least as described in the document. In the case of Muscat, Kcat/Km of the mutant was shown to be about twice as high as that of the wild type by an enzymonological experiment in vitro, and thus the mutation in the disordered region was predicted to result a structural change that was more suitable for the binding of TPP.

In order to greatly increase a monoterpene in a cell, isopentenyl diphosphate (IPP) as a raw material of the monoterpene needs to be increased. Feedback inhibition of DXS by IPP as a product of the deoxyxylulose pathway and competitive inhibition of IPP with TPP have been reported [10]. Moreover, it is known that once IPP reaches a certain amount, DXS, i.e., the first enzyme of the deoxyxylulose pathway, is inhibited so that IPP can no longer increase.

Figure 15:
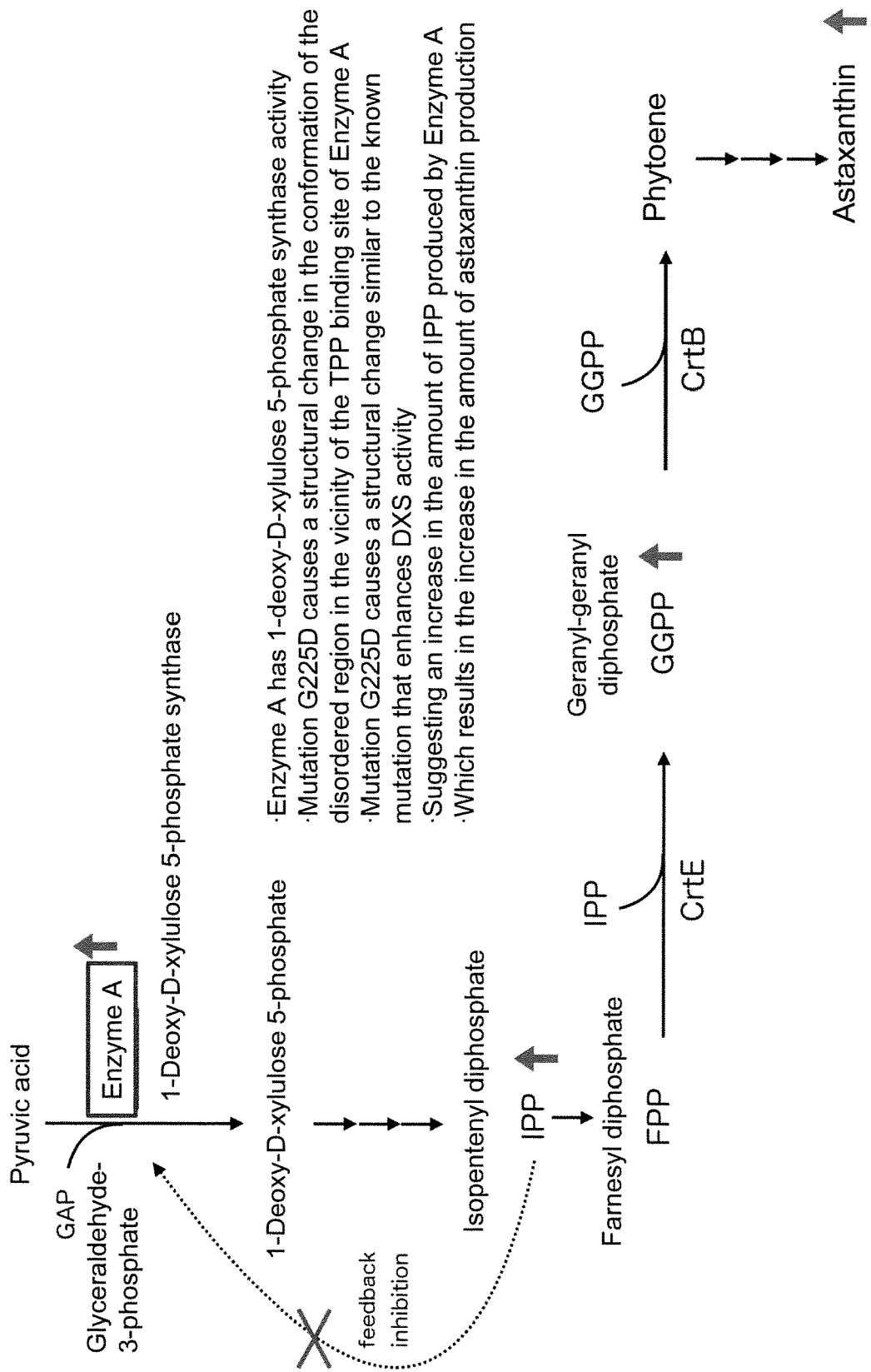
FIG. 15 A diagram showing the deduced effects of mutant enzyme A in the astaxanthin synthesis pathway.

Since the amount of the IPP supplied is regulated to stay at a certain level by DXS due to this feedback inhibition, an increase in the enzymatic activity Kcat/Km of DXS would not simply increase the IPP supply to significantly increase terpene. In a known example, the mutation in the disordered region increased the amount of the synthesized terpene and material of astaxanthin synthesis increased, by which the amount of synthesized astaxanthin was increased (FIG. 15).

3. Construction of Conformational Model of Enzyme C and Analysis of Mutant

From the homology of the amino acid sequences and a comparative conformational analysis, Enzyme C was found to be one kind of polyprenyl diphosphate synthases, namely, decaprenyl diphosphate synthase that synthesizes decaprenyl diphosphate from farnesyl diphosphate (FPP) and seven isopentenyl diphosphates (IPP).

Mutation A305V identified by a genome analysis based on the constructed conformational model of Enzyme C caused steric hindrance due to repulsion of the atoms with the peripheral amino acid residue, and was deduced to destabilize the conformation of Enzyme C. A decrease in Enzyme C activity due to the destabilized conformation decreases the amounts of FPP and IPP digested by Enzyme C. As a result, the increase in the amounts of FPP and IPP that can be used for astaxanthin synthesis seemed to increase the amount of astaxanthin produced.

3.1. Enzymatic Reaction of decaprenyl diphosphate synthase

Decaprenyl diphosphate synthase is an enzyme that has an activity of catalyzing condensation of FPP with IPP and repeats condensation with IPP to synthesize decaprenyl diphosphate (DPP) from FPP and seven IPPs. The enzymatic reaction of decaprenyl diphosphate synthase is shown below.

Chemical formula 2

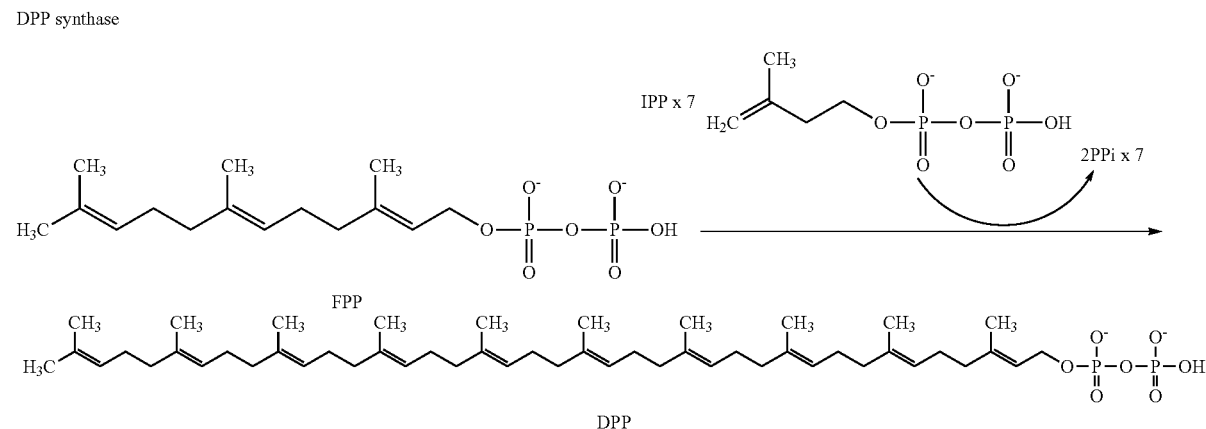

this mutation was predicted to increase the IPP supply, suggesting that feedback inhibition of DXS by IPP was no longer effective.

IPP and TPP competitively bind to DXS in vitro, and are found to inhibit DXS [10]. The mutation in the disordered region that caused a structural change in the TPP binding region suggests not only that it gives a structure suitable for TPP binding but also that feedback inhibition by IPP no longer works because of the effect on IPP binding.

Mutation G225D in Enzyme A was also predicted to result a structural change of the TPP binding region and increase the amount of IPP produced because feedback inhibition by IPP no longer works. As a result, the supply of IPP as a raw

Figure 16:
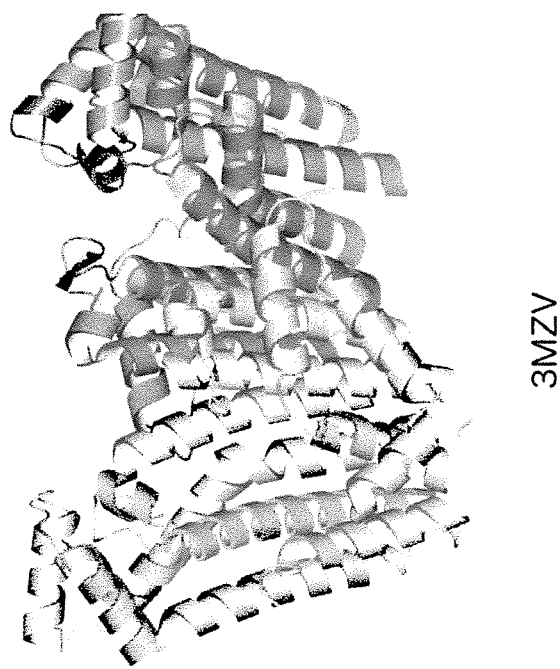
FIG. 16 An image showing a template structure of Enzyme C. *Rhodobacter capsulatus*-derived decaprenyl diphosphate synthase (PDB ID: 3MZV) is shown.

3.2. Construction of Conformational Model of Enzyme C (1) Construction of Conformational Model of Enzyme C by Homology Modeling In order to examine the effects of the active site and the mutations in Enzyme C, a conformational model (FIG. 16) was constructed by homology modeling using, as a template structure, the conformation of *Rhodobacter capsulatus* (*R. capsulatus*)-derived decaprenyl diphosphate synthase (PDB ID: 3MZV) that had the highest amino acid matching degree (amino acid matching degree of 76.2%) among the conformations registered in PDB, and whose conformation had been determined by X-ray crystallography [4].

The homology modeling was conducted based on the conformation alignment between Enzyme C and the template structure (FIG. 17).

(2) Preparation of Enzyme C-Substrate Complex Model

Since the template structure 3MZV is not bonded with a substrate, the conformational data of *Escherichia coli*-derived octaprenyl pyrophosphate synthase (octaprenyl diphosphate synthase) (PDB ID: 3WJN, 3WJO) [11] was used to superimpose 3WJN on the conformational model of Enzyme C and embed FPP as the substrate into the conformational model of Enzyme C, thereby preparing a complex model of Enzyme C and FPP. Next, in the same manner, 3WJO was superimposed and IPP was embedded to prepare a complex model of Enzyme C and FPP and IPP.

FIG. 18 shows the template structure and the constructed model structure. Similar to the template structure, Enzyme C forms a homodimer.

3.3. Regarding Enzyme C (1) Conformational Comparison

The decaprenyl diphosphate synthase as Enzyme C belongs to the polyprenyl diphosphate synthase family (Pfam PF00348 Polyprenyl synthetase). FIG. 19 shows the state of the substrate binding with Enzyme C.

Polyprenyl diphosphate synthase condensates FPP and IPP in the head-to-tail direction (following document [4], the phosphate group side is referred to as the head while the isoprenyl group side is referred to as the tail), thereby synthesizing various polyprenyl diphosphates. By continuing condensation reaction of FPP and IPP, decaprenyl diphosphate synthase extends the prenyl chain deep into the substrate binding site (as represented by an arrow in the right view of FIG. 19) to synthesize C50-decaprenyl diphosphate.

Enzyme C and *R. capsulatus*-derived decaprenyl diphosphate synthase as the template have an amino acid matching degree as high as 76.3% with a conserved active site (FIG. 17). RMSD of the conformation by Ca superimposition was 0.063 Å, where the two enzymes were very similar. When the matching of the amino acid residues was distinguished by colors, a region having different types of amino acid residues was limited to the molecular surface, the active site and the region binding the substrate entirely consisted of matching amino acid residues (FIG. 20).

(2) Comparison by Amino Acid Sequences

Next, the amino acid sequence of Enzyme C was compared with *Paracoccus*-derived decaprenyl diphosphate synthase. *Paracoccus zeaxanthinifaciens* (Q8L1I6)- and *Paracoccus denitrificans* (A1B3M9)-derived amino acid sequences have been submitted to UniProt (http://www.uniprot.org) as already known amino acid sequences of *Paracoccus*-derived decaprenyl diphosphate synthases. When they were compared with the amino acid sequence of Enzyme C, the amino acid matching degree was 75.1% (degree of similarity 89.2%), showing high homology (Table 5).

The amino acid sequence also suggested that Enzyme C was decaprenyl diphosphate synthase. FIG. 21 shows the alignments.

TABLE 5

Comparison of amino acid sequences between Enzyme C and decaprenyl diphosphate synthases

| Protein | Organism | UniProt | Identity (similar) |
|---|---|---|---|
| Decaprenyl diphosphate synthase | *Paracoccus zeaxanthinifaciens* | Q8L1I6 | 86.2% (95.2%) |
| | *Paracoccus denitrificans* | A1B3M9 | 75.1% (89.2%) |

3.4. Deduction of Active Site of Enzyme C

In a complex model of Enzyme C and the substrates, the FPP binding site and the IPP binding site as the substrates and the Mg binding site required for catalysis were deduced. The active sites deduced from these results, and the active center and the substrate binding sites of other polyprenyl diphosphate synthases were highly conserved, and thus Enzyme C was deduced to have a reaction mode similar to that of polyprenyl diphosphate synthase.

The complex model of Enzyme C and the substrates is shown in FIG. 22.

Similar to decaprenyl diphosphate synthase as the template structure, Enzyme C was expected to form a homodimer. FIG. 22 shows the binding sites of FPP and IPP in chain A (light red). FPP binds to the tunnel region of chain A while FPP and IPP bind to each other in a head-to-tail form with the phosphate group of FPP directing toward the isopentenyl group of IPP. A catalytic reaction occurs between the phosphate group of FPP and the isopentenyl group of IPP in the presence of Mg.

In order to deduce the active site of Enzyme C, amino acid residues present in the vicinity of FPP and IPP were detected in the Enzyme C-substrate complex model to deduce the interaction between the substrate and the amino acid residues. For PPP, hydrogen bonds between phosphate groups and Arg102, Lys179 and Lys244, and hydrophobic interactions between polyprenyl groups and Ala88, Thr89, His92 and Phe125 were deduced (FIG. 23, top image).

Figure 23:
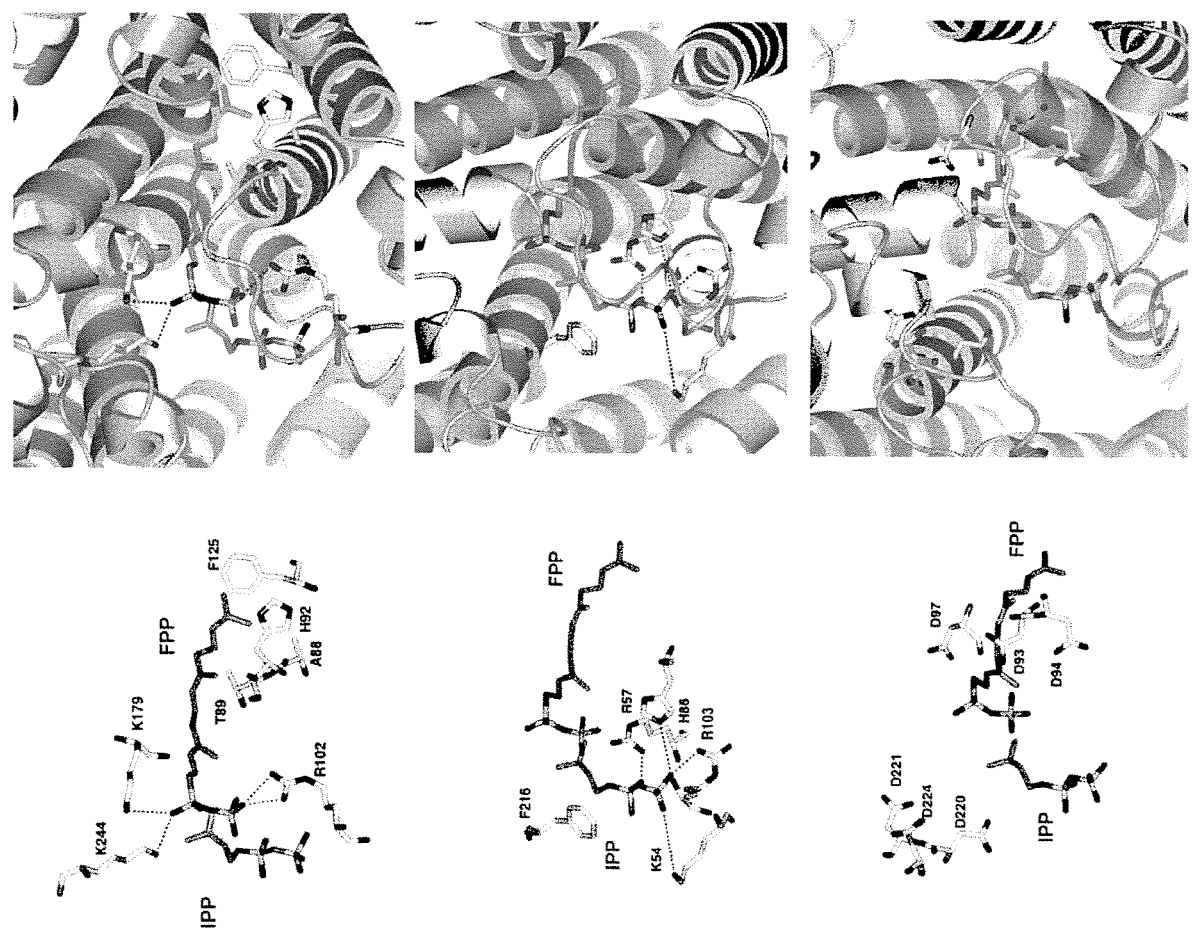
FIG. 23 Images showing the amino acid residues of Enzyme C predicted to be responsible for the interactions with FPP (top), IPP (center) and Mg (bottom).

For IPP, hydrogen bonds between phosphate groups and Lys54, Arg57, His86 and Arg103, and a hydrophobic interaction between an isopentenyl group and Phe216 were deduced (FIG. 23, center image).

This catalytic reaction requires Mg. As Mg binding sites, two DDXXD motifs are known in a known polyprenyl diphosphate synthase [11]. Although the coordinates of Mg are not determined in the template structure, Asp93, Asp94, Asp97 and Asp220, and Asp221 and Asp224 corresponding to the DDXXD motifs exist near phosphate groups in Enzyme C similar to the known Mg binding sites, and thus these amino acid residues were deduced to bind Mg (FIG. 23, bottom image).

Figure 24:
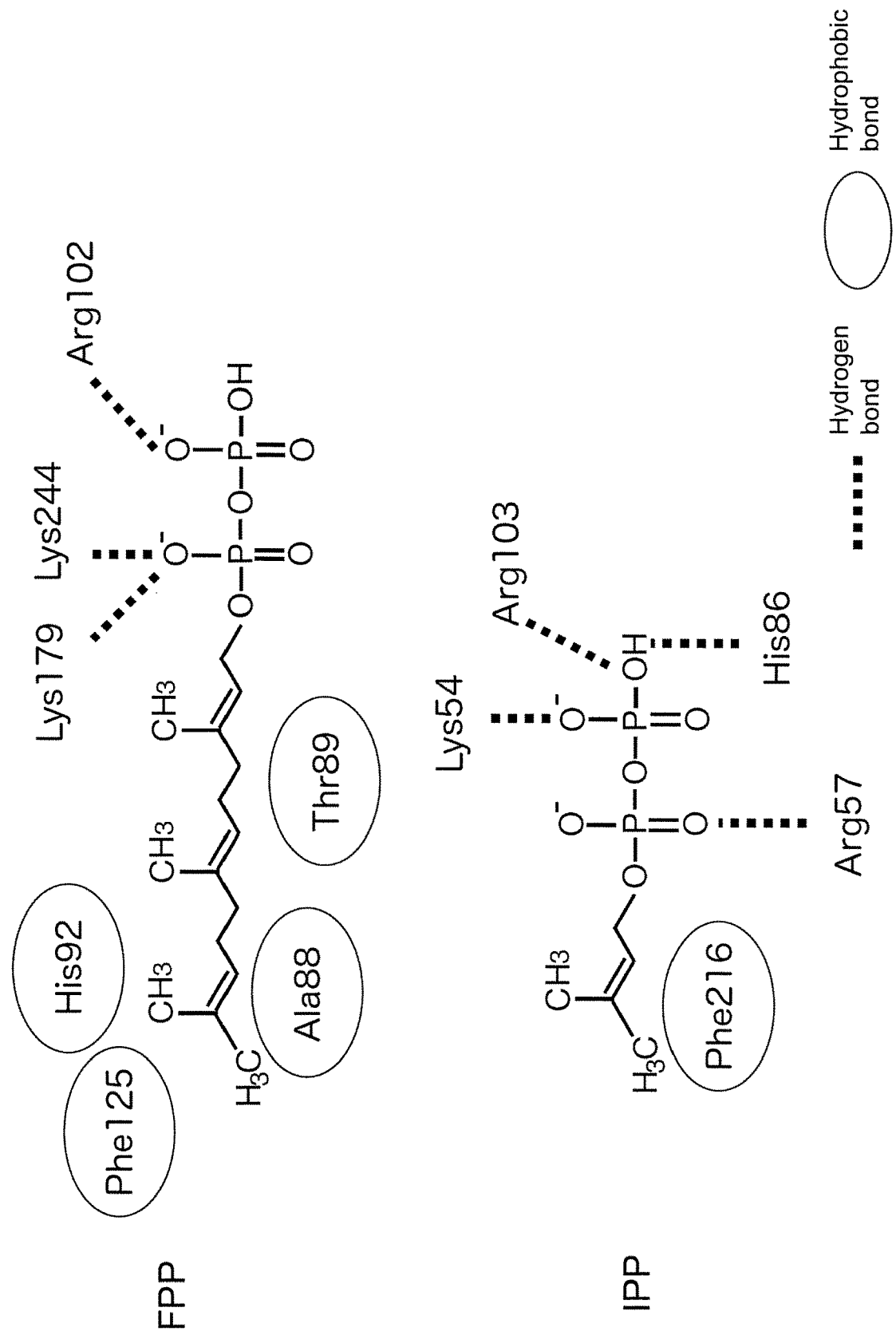
FIG. 24 A depiction showing the interaction of Enzyme A with substrates FPP and IPP.
Figure 25:
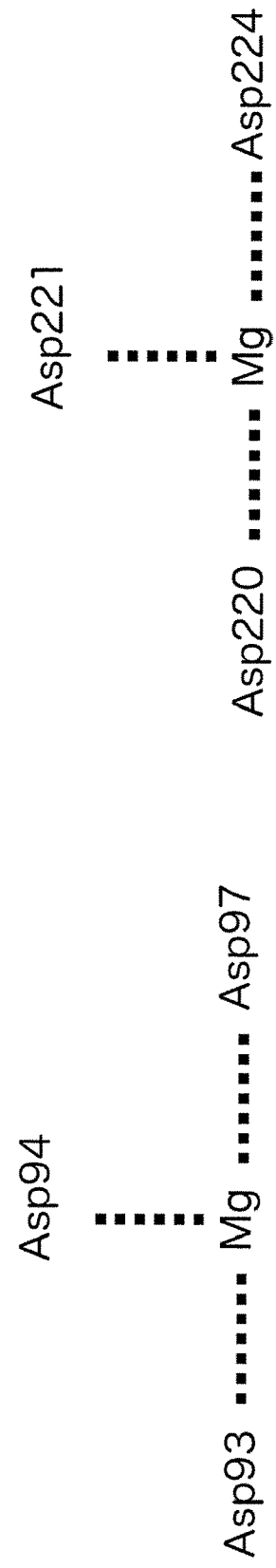
FIG. 25 A depiction showing the interaction of Enzyme A with Mg.

The deduced active sites are shown in Tables 6-8. In addition, the binding modes between Enzyme C and FPP and IPP as well as the binding modes between Enzyme C and Mg are shown in FIGS. 24 and 25, respectively.

TABLE 6

Amino acid residues predicted to have interactions
with FPP and IPP detected in Enzyme C

| Substrate | | Enzyme_C | | interaction |
|---|---|---|---|---|
| FPP | Polyprenyl | Ala88 | side-chain | hydrophobic interaction |
| | | Thr89 | side-chain | hydrophobic interaction |
| | | His92 | side-chain | hydrophobic interaction |
| | | Phe125 | side-chain | hydrophobic interaction |
| | PO4 | Arg102 | side-chain | hydrogen bond |
| | | Lys179 | side-chain | hydrogen bond |
| | | Lys244 | side-chain | hydrogen bond |
| IPP | Isopentenyl | Phe216 | side-chain | hydrophobic interaction |
| | PO4 | Lys54 | side-chain | hydrogen bond |
| | | Arg57 | side-chain | hydrogen bond |
| | | His86 | side-chain | hydrogen bond |
| | | Arg103 | side-chain | hydrogen bond |

TABLE 7

Amino acid residues predicted to have interaction
with Mg detected in Enzyme C

| Mg | Enzyme_C | | Interaction |
|---|---|---|---|
| Mg 1 | Asp93 | side-chain | hydrogen bond |
| | Asp94 | side-chain | hydrogen bond |
| | Asp97 | side-chain | hydrogen bond |
| Mg 2 | Asp220 | side-chain | hydrogen bond |
| | Asp221 | side-chain | hydrogen bond |
| | Asp224 | side-chain | hydrogen bond |

TABLE 8

Amino acid residues of deduced active sites in Enzyme C

| binding site | residue |
|---|---|
| FPP | Ala88 |
| | Thr89 |
| | His92 |
| | Arg102 |
| | Phe125 |
| | Lys179 |
| | Lys244 |
| IPP | Lys54 |
| | Arg57 |
| | His86 |
| | Arg103 |
| | Phe216 |
| Mg | Asp93 |
| | Asp94 |
| | Asp97 |
| | Asp220 |
| | Asp221 |
| | Asp224 |

Each of the amino acid residues at the deduced bonds matches that of *R. capsulatus*-derived decaprenyl diphosphate synthase as the template structure (FIG. 17). In addition, since the FPP binding site, the IPP binding site and the Mg binding site of Enzyme C retain the binding site of *E. coli*-derived octaprenyl diphosphate synthase used for making the substrate complex model, Enzyme C is considered to take a reaction mode similar to octaprenyl diphosphate synthase.

In particular, Arg102, Lys179 and Lys244 that bind to the phosphate group of FPP, and Asp93, Asp94, Asp97, Asp220, Asp221 and Asp224 that bind to Mg seem to be important residues that are directly responsible for the activity of catalyzing transfer of the phosphate groups. Experiments of preparing rat and yeast FPP synthase mutants reported that amino acid residues corresponding to Arg102 and Arg103 as phosphate binding sites and Asp94, Asp97, Asp220, Asp224 and Asp224 as Mg binding sites of Enzyme C were important for enzymatic activity, and that these amino acid residues were highly conserved among polyprenyl diphosphate synthases [14, 15].

In addition, in FPP synthase, side chains of Phe and Gln were found to be important for substrate binding through preparation of mutants of the amino acid residues corresponding to Phe216 and Gln217 of Enzyme C [16]. Phe216 and Gln217 also existed in the region of the active site in the complex model of Enzyme C and thus were predicted to be important for the activity.

3.5. Effect of Mutation A305V in Enzyme C

In order to deduce the effect of mutation from Ala305 to Val identified in Enzyme C on the conformation, a conformational model of mutant A305V enzyme of Enzyme C was prepared.

(1) Preparation of Mutant Model by A305V Single Residue Substitution

In order to observe the effect of substitution from Ala to Val, a model was first prepared by fixing the conformation of the rest of the amino acid residues (assuming it to be a rigid body) and allowing a single residue substitution from Ala305 to Val, to compare the model with the wild type.

FIG. 26 shows conformational models of the wild-type and mutant A305V enzymes. Ala305 in the wild type was present in the α-helix (pink), where the side chain provided packing with the amino acid residue of the adjacent α-helix (cyan) via a hydrophobic interaction.

Figure 27:
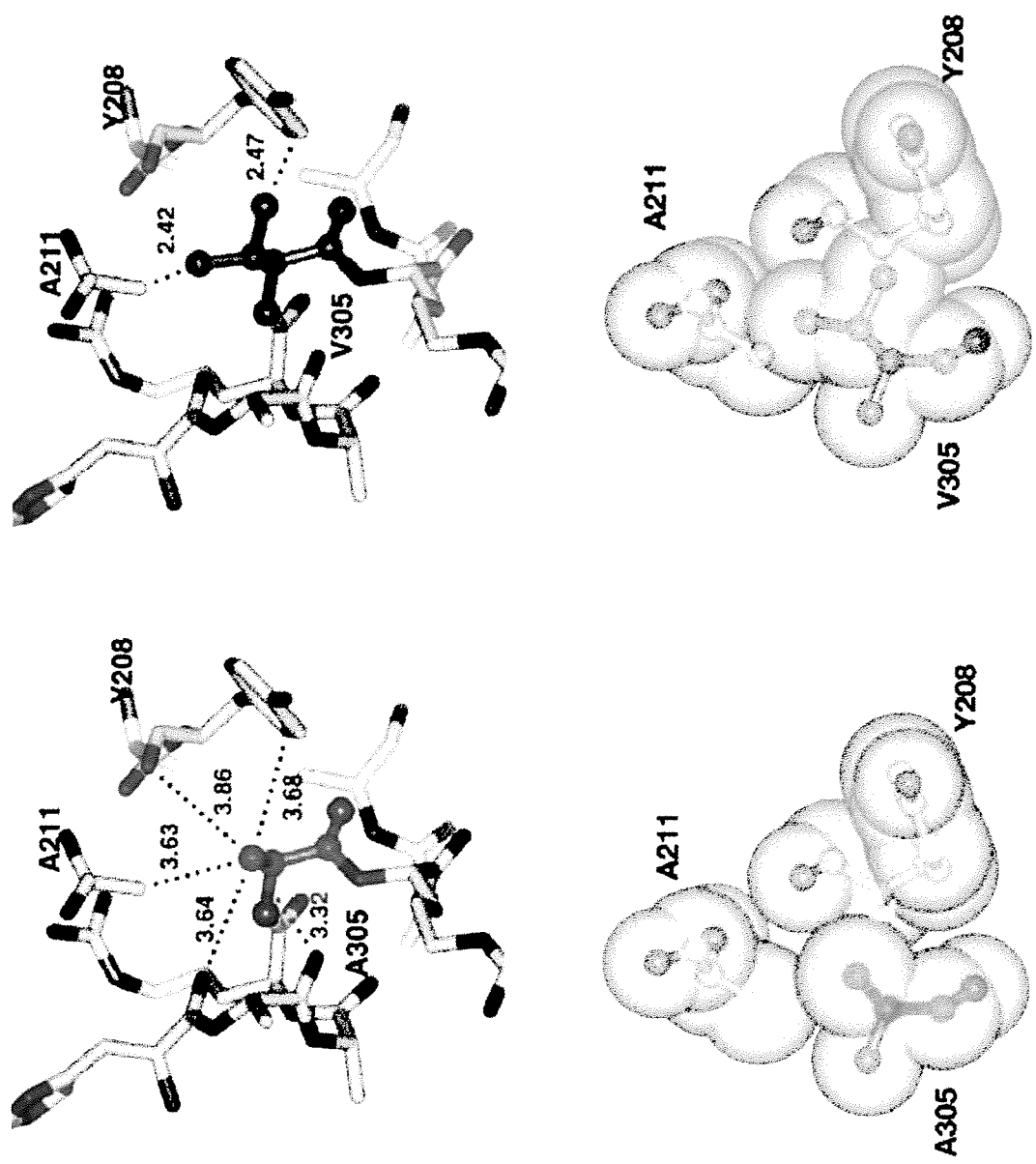
FIG. 27 Images showing the surrounding structures of Ala305 of the wild type (left) and Val305 of the mutant (right). Ala305 makes contact with the peripheral amino acid residues. Mutation Val305 causes steric hindrance with the peripheral structure. Ala305 is depicted in green while Val305 is depicted in magenta.

FIG. 27 shows the structure of the amino acid residue adjacent to Ala305.

The carbon atom of the methyl group as the side chain of Ala305 makes contact with the peripheral amino acid residues Tyr208, Ala211, His301 and Ala302, where the interatomic distances between the carbons were all less than 4.0 Å. The substitution from Ala305 to Val results in an addition of two methyl groups to the side chain. In the conformational model including the substitution from Ala305 to Val, the interatomic distances between the carbon of the methyl group of the side chain of Val and the carbons of Tyr208 and Ala211 were 2.42 Å and 2.47 Å, respectively.

The lower limit of the contact distance between carbons via a noncovalent bond is 2.9 Å. Since the interatomic distances of the carbons measured with respect to Val305 was lower than this value, these carbon atoms would repel and cause steric hindrance with the peripheral amino acid residues. In a space-filling representation, the interatomic distances were shorter than the van der Waals radii, confirming repulsion between the atoms. Accordingly, A305V mutation was predicted to induce steric hindrance in Enzyme C due to repulsion of the atoms, which leads to destabilization of the conformation.

(2) Change in Intramolecular Energy Due to Mutation A305V

In order to examine the destabilization of the structure caused by A305V, the intramolecular energies of the wild-type and mutant A305V Enzyme C were computed in terms of unit kilojoules/mol (KJ/mol) from a set of the interatomic bond length, the bond angle, the torsion, the bond energy and the like.

Figure 28:
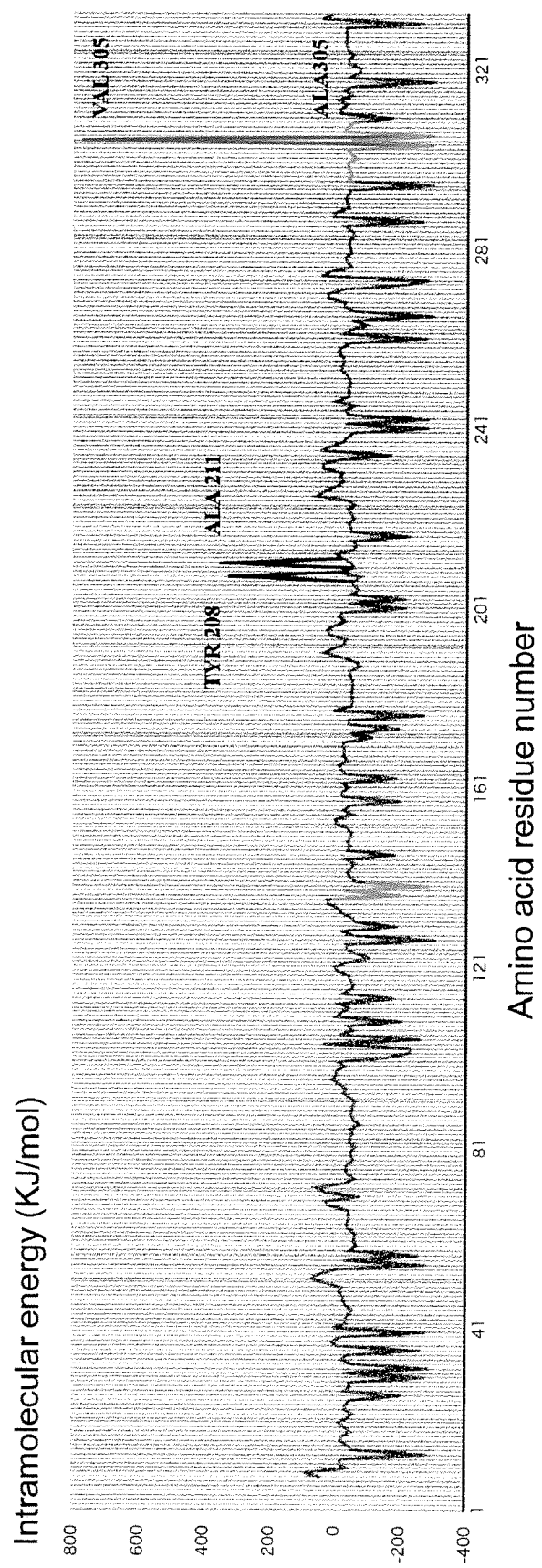
FIG. 28 A diagram showing comparison of intramolecular energies between the wild type (blue) and mutant A305V (red).

As a result, mutant A305V enzyme gave an intramolecular energy of −16,295 (KJ/mol) while the wild type gave −17,912 (KJ/mol), showing an increase of 9.02% and confirming destabilization of the structure. This increase in the intramolecular energy were particularly observed at the amino acid residues of Tyr208, Ala211 and Val305, and thus repulsion caused by these amino acid residues seemed to result the increase in the intramolecular energy. Comparison of the intramolecular energies between the wild-type and mutant A305V Enzyme C is shown in FIG. 28.

(3) Structural Change Caused by Mutation A305V

Next, an energy minimization calculation was performed on the mutant model so as to examine if repulsion due to A305V can be avoided by moving the conformation of the peripheral amino acid residues. As a result, it was found that the conformation of the amino acid residues of the α-helix adjacent to the α-helix in which Val305 exists needs to be moved in order to avoid repulsion of the side chain of Val305 while accepting the side chain. Specifically, it was predicted that this structural change not only affects the side chain but also the main chain, and thus the original packing between the α-helices does not occur in the mutant A305V enzyme and the structure surrounding the two helices was destabilized. Furthermore, the active sites that bond substrate IPP and Mg (Phe216, Gln217, Asp220) are present in the α-helix adjacent to mutation A305V. The structural change in the main-chain structure of the α-helix as the basis of the active sites dislocates the amino acid residues of the active sites, and this would have an effect on the substrate bonds and activity themselves (FIG. 29, right).

Figure 30:
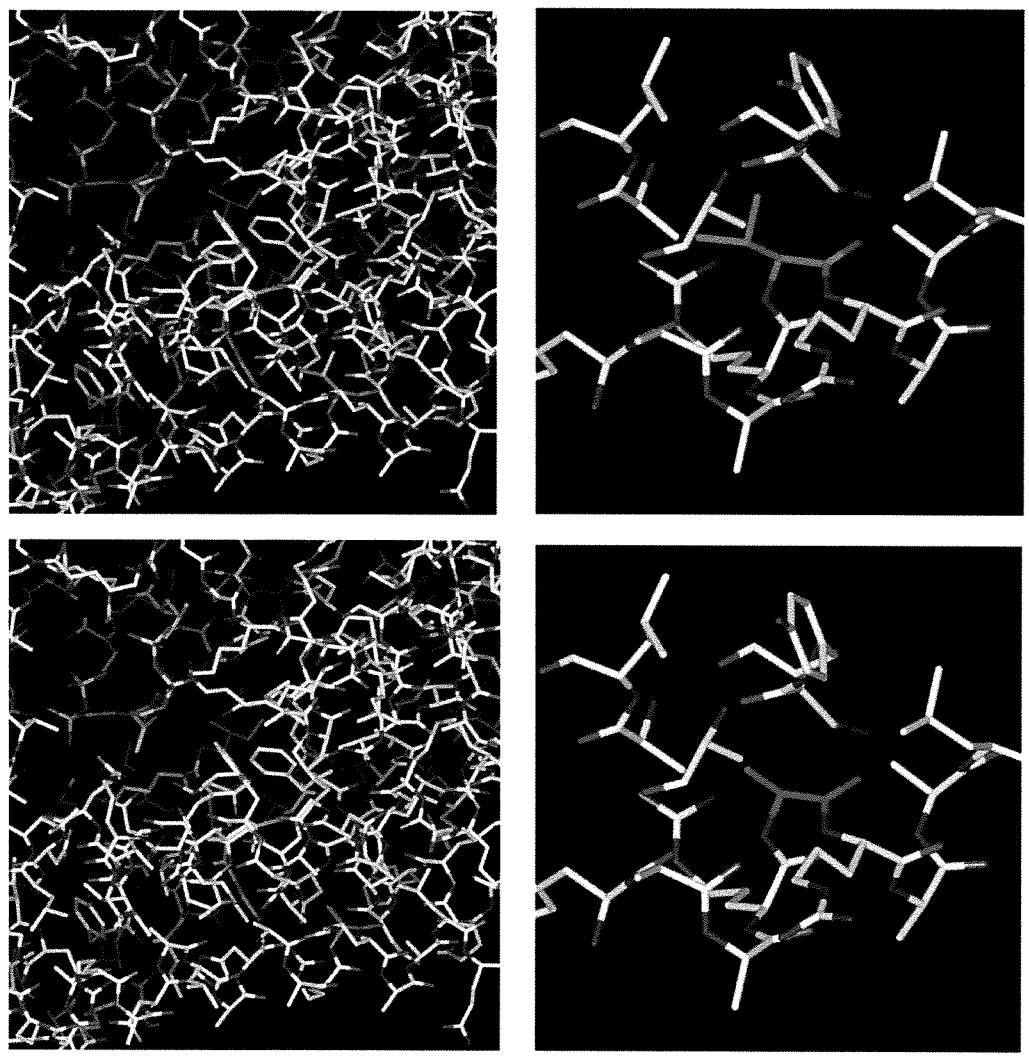
FIG. 30 Images showing the effect of A305V in Enzyme C.
Figure 31:
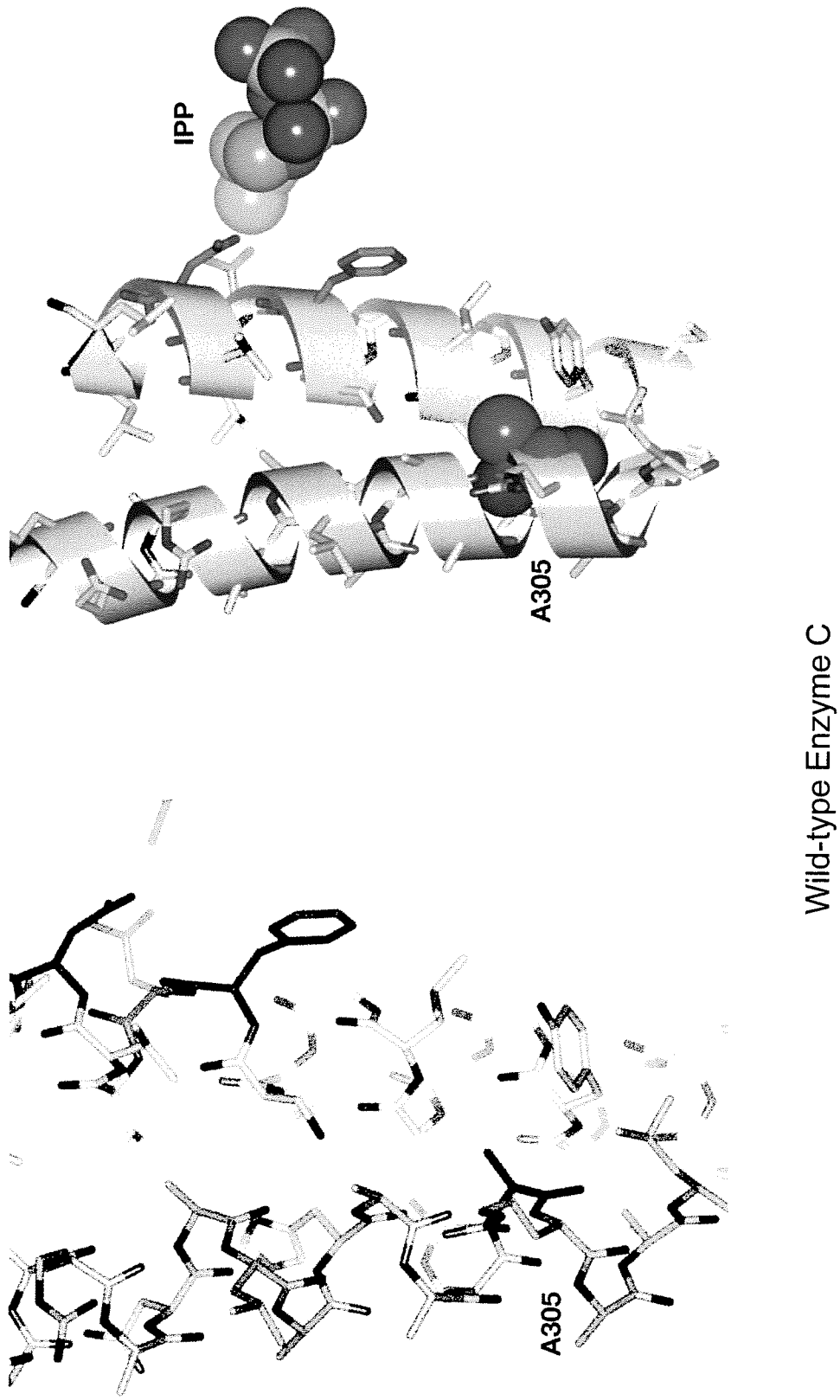
FIG. 31 Images showing the effect of A305V in Enzyme C.

FIG. 29 shows the structures around Ala305 and Val305 in the wild type and the mutant A305V following energy minimization calculation, while FIGS. 30, 31 and 32 show the structural changes in mutant A305V.

(4) Decrease in Enzyme C Activity Due to Structural Destabilization

Thus, from the conformational model of A305V, occurrence of the steric hindrance with the peripheral amino acid residues, the increase in the intramolecular energy and the structural change in the adjacent two α-helices were deduced, suggesting that mutation A305V destabilizes the conformation of Enzyme C. Conformational destabilization caused by point mutation has also been reported frequently in genetic disorders and the like. For example, a protein that has a destabilization-inducing mutation may be deactivated in shorter time than usual for being unable to maintain the original conformation in a solvent, and the mutant protein that cannot give original packing in the cell is eliminated by the function of the cell itself. Accordingly, the mutant A305V enzyme that does not have the original activity and that has an unstable structure may be eliminated in the bacterium, which is deduced to consequently decrease the Enzyme C activity in the bacterium.

3.6. Effect of Mutation A305V in Enzyme C on Astaxanthin Synthesis Pathway

Decaprenyl diphosphate synthase is one of the enzymes in the coenzyme C10 (CoQ10) synthesis pathway. *Paracoccus zeaxanthinifaciens-* or *Paracoccus denitrificans-*derived decaprenyl diphosphate synthase that was confirmed to be highly homologous with Enzyme C this time is found to be an enzyme required for CoQ10 production [Japanese Patent Application Publication No. 2005-211020, Japanese Patent Application Publication No. 2006-517794]. FPP and IPP as the substrates of decaprenyl diphosphate synthase also serve as substrates of geranyl-geranyl diphosphate (GGPP) synthase CrtE in the astaxanthin synthesis pathway. Therefore, in a usual *Paracoccus* cell, decaprenyl diphosphate synthase and CrtE are considered to compete for substrates FPP and IPP.

Mutation A305V identified in Enzyme C was deduced to decrease the Enzyme C activity by destabilizing the molecular conformation. The decreased Enzyme C activity means decreased amounts of the substrates FPP and IPP used, which would increase the amounts of FPP and IPP that can be used in the astaxanthin synthesis pathway.

CrtE synthesizes one molecule of GGPP from one molecule of FPP and one molecule of IPP. Meanwhile, Enzyme C requires one molecule of FPP and seven molecules of IPP to synthesize one molecule of decaprenyl diphosphate. In terms of IPP, Enzyme C digests IPP seven times as much as CrtE in a single reaction. Thus, the decrease in the Enzyme C activity seems very effective for increasing the IPP supplied to the astaxanthin synthesis pathway.

Figure 33:
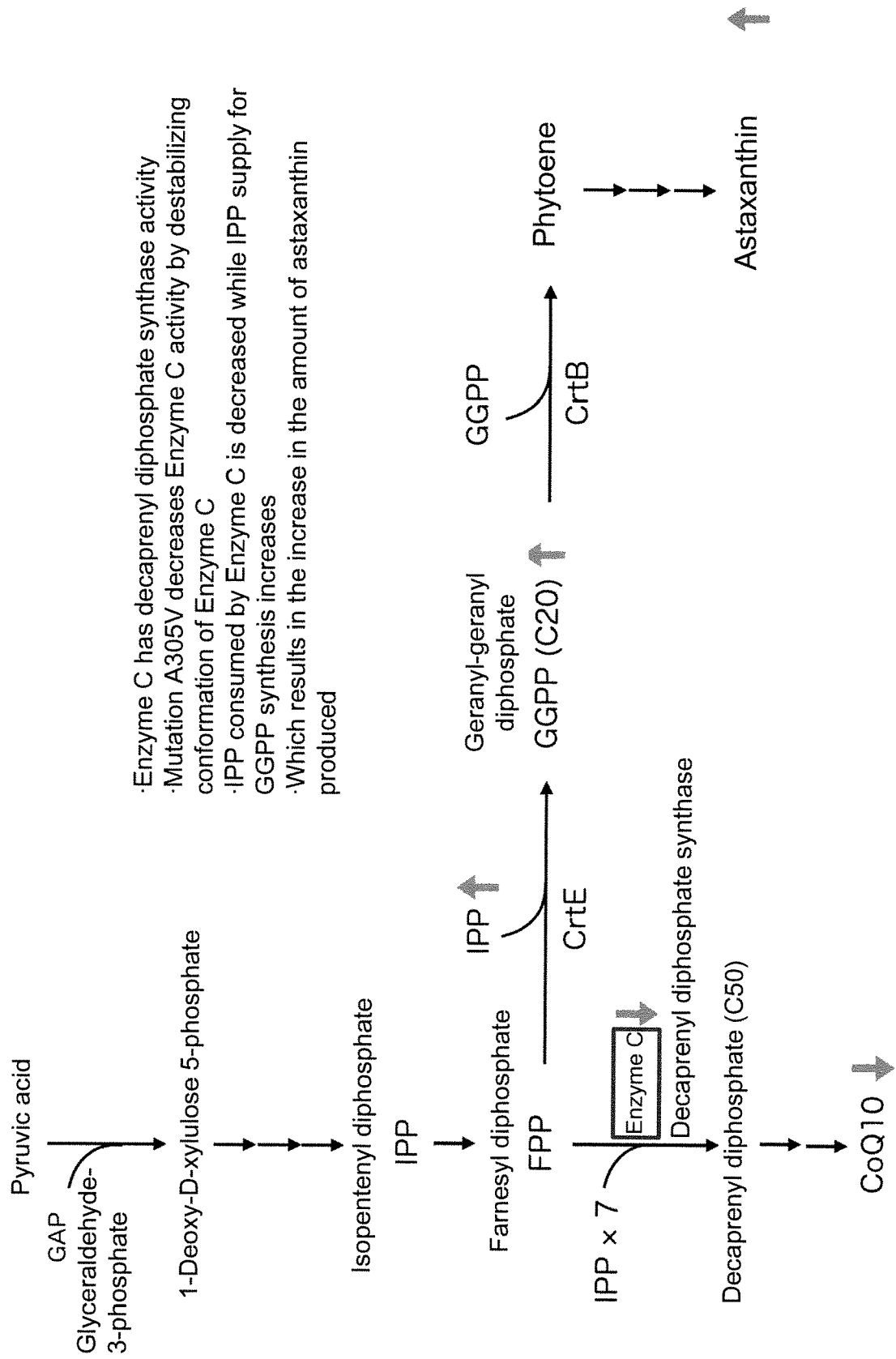
FIG. 33 A diagram showing the deduced effect of mutant Enzyme C in the astaxanthin synthesis pathway.

As a result, the amount of the synthesized astaxanthin is deduced to increase significantly (FIG. 33).

REFERENCES

1. SWISS-MODEL: modelling protein tertiary and quaternary structure using evolutionary information. Biasini M, Bienert S, Waterhouse A, Arnold K, Studer G, Schmidt T, Kiefer F, Cassarino T G, Bertoni M, Bordoli L, Schwede T. Nucleic Acids Res. 2014; 42:W252-8.
2. Automated comparative protein structure modeling with SWISS-MODEL and Swiss-PdbViewer: A historical perspective. Guex, N., Peitsch, M. C., Schwede, T. Electrophoresis, (2009). 30(S1), S162-S173.
3. Crystal structure of 1-deoxy-D-xylulose 5-phosphate synthase, a crucial enzyme for isoprenoids biosynthesis. Xiang S, Usunow G, Lange G, Busch M, Tong L. J Biol Chem. 2007 26; 282(4): 2676-82.
4. Prediction of function for the polyprenyl transferase subgroup in the isoprenoid synthase superfamily. Wallrapp F H, Pan J J, Ramamoorthy G, Almonacid D E, Hillerich B S, Seidel R, Patskovsky Y, Babbitt P C, Almo S C, Jacobson M P, Poulter C D. Proc Natl Acad Sci USA. 2013 26; 110(13):E1196-202.14; 107(50):21337-42.
6. Snapshot of a key intermediate in enzymatic thiamin catalysis: crystal structure of the alpha-carbanion of (alpha,beta-dihydroxyethyl)-thiamin diphosphate in the active site of transketolase from *Saccharomyces cerevisiae*. Fiedler E, Thorell S, S andalova T, Golbik R, König S, Schneider G. Proc Natl Acad Sci USA. 2002 22; 99(2):591-5.
7. Examination of substrate binding in thiamin diphosphate-dependent transketolase by protein crystallography and site-directed mutagenesis. Nilsson U1, Meshalkina L, Lindqvist Y, Schneider G. J Biol Chem. 1997 17; 272(3): 1864-9.
8. Catalytically Important Residues in *E. coli* 1-Deoxy-D-Xylulose 5-Phosphate Synthase. Jordi Querol-Audí, Albert Boronat, Josep J. Centelles, Santiago Imperial Journal of Biosciences and Medicines, 2014, 2, 30-35

9. Functional effect of grapevine 1-deoxy-D-xylulose 5-phosphate synthase substitution K284N on Muscat flavour formation. Battilana J1, Emanuelli F, Gambino G, Gribaudo I, Gasperi F, Boss P K, Grando M S. J Exp Bot. 2011; 62(15):5497-508.
10. Feedback Inhibition of Deoxy-D-xylulose-5-phosphate Synthase Regulates the Methylerythritol 4-Phosphate Pathway. Banerjee A1, Wu Y, Banerjee R, Li Y, Yan H, Sharkey T D. J Biol Chem. 2013 7; 288(23):16926-36.
11. Crystal structures of ligand-bound octaprenyl pyrophosphate synthase from *Escherichia coli* reveal the catalytic and chain-length determining mechanisms. Han X, Chen C C, Kuo C J, Huang C H, Zheng Y, Ko T P, Zhu Z, Feng X, Wang K, Oldfield E, Wang A H, Liang P H, Guo R T, Ma Y. Proteins. 2015; 83(1):37-45.
14. Effect of site-directed mutagenesis of conserved aspartate and arginine residues upon farnesyl diphosphate synthase activity. Joly A, Edwards P A. J Biol Chem. 1993 25; 268(36):26983-9.
15. Yeast farnesyl-diphosphate synthase: site-directed mutagenesis of residues in highly conserved prenyltransferase domains I and II. Song L1, Poulter C D. Proc Natl Acad Sci USA. 1994 12; 91(8): 3044-8.
16. Significance of Phe-220 and Gln-221 in the catalytic mechanism of farnesyl diphosphate synthase of *Bacillus stearothermophilus*. Koyama T1, Tajima M, Nishino T, Ogura K. Biochem Biophys Res Commun. 1995 7; 212 (2):681-6.

The invention claimed is:

1. A mutant carotenoidogenic bacterium that produces a carotenoid, comprising a combination of
   (i) a gene selected from (a)-(c), and
   (ii) a gene selected from (d)-(f); which are:
   (a) a gene encoding a protein comprising a mutant amino acid sequence in which at least glycine of the 225th amino acid residue in the amino acid sequence of SEQ ID NO:2 of 1-deoxy-D-xylulose 5-phosphate synthase (DXS) of a carotenoidogenic bacterium belonging to the genus *Paracoccus* has been substituted with aspartic acid;
   (b) a gene encoding a protein comprising a mutant amino acid sequence in which glycine of the 225th amino acid residue in the amino acid sequence of SEQ ID NO:2 of DXS is substituted with aspartic acid and in which one to several amino acid residues other than the 225th amino acid residue have been deleted, substituted or added, and that has DXS activity;
   (c) a gene consisting of DNA comprising the nucleotide sequence of SEQ ID NO:5;
   (d) a gene encoding a protein comprising a mutant amino acid sequence in which at least alanine of the 305th amino acid residue in the amino acid sequence of SEQ ID NO:4 of decaprenyl diphosphate synthase (DPS) of a carotenoidogenic bacterium belonging to the genus *Paracoccus* has been substituted with valine;
   (e) a gene encoding a protein comprising a mutant amino acid sequence in which alanine of the 305th amino acid residue in the amino acid sequence of SEQ ID NO:4 of DPS is substituted with valine and in which one to several amino acid residues other than the 305th amino acid residue have been deleted, substituted or added, and that has reduced DPS activity; and
   (f) a gene consisting of DNA comprising the nucleotide sequence of SEQ ID NO:7.

2. The bacterium according to claim 1, which has acquired carotenogenic capacity that is higher than the carotenogenic capacity of a carotenoidogenic bacterium without the gene encoding the protein comprising the mutant amino acid sequence.

3. The bacterium according to claim 2, which has acquired carotenogenic capacity that is at least 5 times or more the carotenoid production amount of a carotenoidogenic bacterium without the gene encoding the protein comprising the mutant amino acid sequence.

4. The bacterium according to claim 1, wherein the bacterium belonging to the genus *Paracoccus* is strain E-396.

5. The bacterium according to claim 1, wherein the carotenoid is astaxanthin.

6. A method for producing a carotenoid, comprising culturing the bacterium according to claim 1, and collecting the carotenoid from the resulting cultured product.

7. The method according to claim 6, wherein the carotenoid production amount is at least 5 times or more the carotenoid production amount of a carotenoidogenic bacterium without the gene encoding the protein comprising the mutant amino acid sequence.

8. The method according to claim 1, wherein the carotenoid is astaxanthin.

9. A recombinant vector comprising a combination of
   (i) a gene selected from (a)-(c), and
   (ii) a gene selected from (d)-(f); which are:
   (a) a gene encoding a protein comprising a mutant amino acid sequence in which at least glycine of the 225th amino acid residue in the amino acid sequence of SEQ ID NO:2 of 1-deoxy-D-xylulose 5-phosphate synthase (DXS) of a carotenoidogenic bacterium belonging to the genus *Paracoccus* has been substituted with aspartic acid;
   (b) a gene encoding a protein comprising a mutant amino acid sequence in which glycine of the 225th amino acid residue in the amino acid sequence of SEQ ID NO:2 of DXS is substituted with aspartic acid and in which one to several amino acid residues other than the 225th amino acid residue have been deleted, substituted or added, and that has DXS activity;
   (c) a gene consisting of DNA comprising the nucleotide sequence of SEQ ID NO:5;
   (d) a gene encoding a protein comprising a mutant amino acid sequence in which at least alanine of the 305th amino acid residue in the amino acid sequence of SEQ ID NO:4 of decaprenyl diphosphate synthase (DPS) of a carotenoidogenic bacterium belonging to the genus *Paracoccus* has been substituted with valine;
   (e) a gene encoding a protein comprising a mutant amino acid sequence in which alanine of the 305th amino acid residue in the amino acid sequence of SEQ ID NO:4 of DPS is substituted with valine and in which one to several amino acid residues other than the 305th amino acid residue have been deleted, substituted or added, and that has reduced DPS activity; and
   (f) a gene consisting of DNA comprising the nucleotide sequence of SEQ ID NO:7.

10. A transformant comprising the recombinant vector according to claim 9.

11. A method for producing a carotenoid, comprising culturing the transformant according to claim 10, and collecting a carotenoid from the resulting cultured product.

* * * * *